(12) United States Patent
Rokhsaz et al.

(10) Patent No.: US 10,734,727 B2
(45) Date of Patent: Aug. 4, 2020

(54) RADIO FREQUENCY IDENTIFICATION (RFID) MOISTURE TAG(S) AND SENSORS WITH EXTENDED SENSING VIA CAPILLARIES

(71) Applicant: RFMicron, Inc., Austin, TX (US)

(72) Inventors: Shahriar Rokhsaz, Austin, TX (US); Brian David Young, Austin, TX (US); Marwan Hassoun, Austin, TX (US)

(73) Assignee: RFMicron, Inc., Austin, TX (US)

( * ) Notice: Subject to any disclaimer, the term of this patent is extended or adjusted under 35 U.S.C. 154(b) by 0 days.

(21) Appl. No.: 16/119,365

(22) Filed: Aug. 31, 2018

(65) Prior Publication Data

US 2019/0097323 A1    Mar. 28, 2019

Related U.S. Application Data

(63) Continuation of application No. 15/443,050, filed on Feb. 27, 2017, now Pat. No. 10,069,205, which is a
(Continued)

(51) Int. Cl.
*H01Q 9/04* (2006.01)
*G06K 19/07* (2006.01)
*G08B 21/20* (2006.01)

(52) U.S. Cl.
CPC ............. *H01Q 9/0442* (2013.01); *H01Q 9/04* (2013.01); *G06K 19/0717* (2013.01); *G08B 21/20* (2013.01)

(58) Field of Classification Search
CPC ........ G08B 21/20; G08B 21/22; G60K 19/07; G60K 19/0716; G60K 19/0717;
(Continued)

(56) References Cited

U.S. PATENT DOCUMENTS 8,242,908 B2 * 8/2012 Butler ................ G06K 19/0723
340/10.1
8,279,065 B2 * 10/2012 Butler ................ G06K 19/0723
340/10.1
(Continued)

FOREIGN PATENT DOCUMENTS

WO        2012054474 A1     4/2012

OTHER PUBLICATIONS

International Search Authority; Written Opinion of the International Searching Authority; International Application No. PCT/US15/54793; dated Apr. 12, 2016; 14 pgs.

*Primary Examiner* — Van T Trieu
(74) *Attorney, Agent, or Firm* — Garlick & Markison; Timothy W. Markison

(57) ABSTRACT

A radio frequency identification (RFID) tag includes a power harvesting circuit, an RF front-end, and a processing module. The power harvesting circuit generates power for the RFID tag from a continuous wave of an inbound radio frequency (RF) signal. The RF front-end receives the inbound RF signal and transmits an outbound RF signal. The RF front-end includes a tuning circuit that is tuned based on a capacitance setting. The tuning of the tuning circuit effects a characteristic of the RF front-end. The processing module generate the capacitance setting to adjust the characteristic of the RF front-end to a desired characteristic.

8 Claims, 45 Drawing Sheets

Related U.S. Application Data continuation of application No. 14/879,088, filed on Oct. 8, 2015, now Pat. No. 9,582,981.

(60) Provisional application No. 62/061,257, filed on Oct. 8, 2014, provisional application No. 62/079,369, filed on Nov. 13, 2014, provisional application No. 62/147,890, filed on Apr. 15, 2015, provisional application No. 62/195,038, filed on Jul. 21, 2015.

(58) Field of Classification Search
CPC ........... G60K 19/0723; G60K 19/0726; G60K 19/0727; H01Q 1/22; H01Q 1/2208; H01Q 1/2216; H01Q 1/2283; H01Q 9/04; H01Q 9/0442

See application file for complete search history.

(56) References Cited

U.S. PATENT DOCUMENTS

| | | | |
|---|---|---|---|
| 8,744,418 | B2 | 6/2014 | Novet |
| 8,988,223 | B2* | 3/2015 | Puleston ................. H04L 67/04 340/10.1 |
| 9,424,447 | B2* | 8/2016 | Puleston ................. H04L 67/04 |
| 9,786,145 | B2 | 10/2017 | Oppenheimer |
| 2002/0145526 | A1 | 10/2002 | Friedman |
| 2004/0070510 | A1 | 4/2004 | Zhang et al. |
| 2006/0109124 | A1 | 5/2006 | Dixon |
| 2009/0045961 | A1 | 2/2009 | Chamarti et al. |
| 2009/0102663 | A1* | 4/2009 | Hillegass ............. G06K 7/0008 340/572.5 |
| 2010/0022548 | A1 | 9/2010 | Kasai et al. |
| 2012/0126911 | A1 | 5/2012 | Romanko |
| 2013/0123726 | A1 | 5/2013 | Yu et al. |
| 2014/0089243 | A1 | 3/2014 | Oppenheimer |
| 2015/0080819 | A1 | 3/2015 | Charna |
| 2015/0135078 | A1 | 5/2015 | Erkkila |
| 2016/0337789 | A1 | 11/2016 | Rokhsaz |
| 2017/0324860 | A1 | 11/2017 | Novet |

* cited by examiner

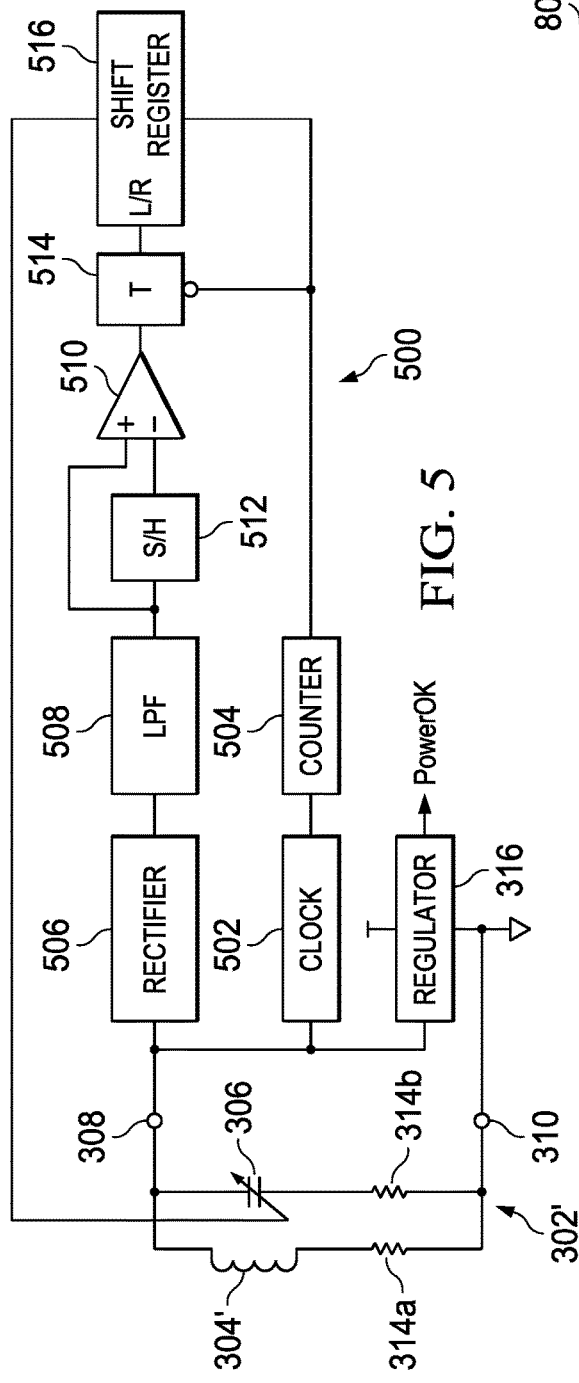
FIG. 5
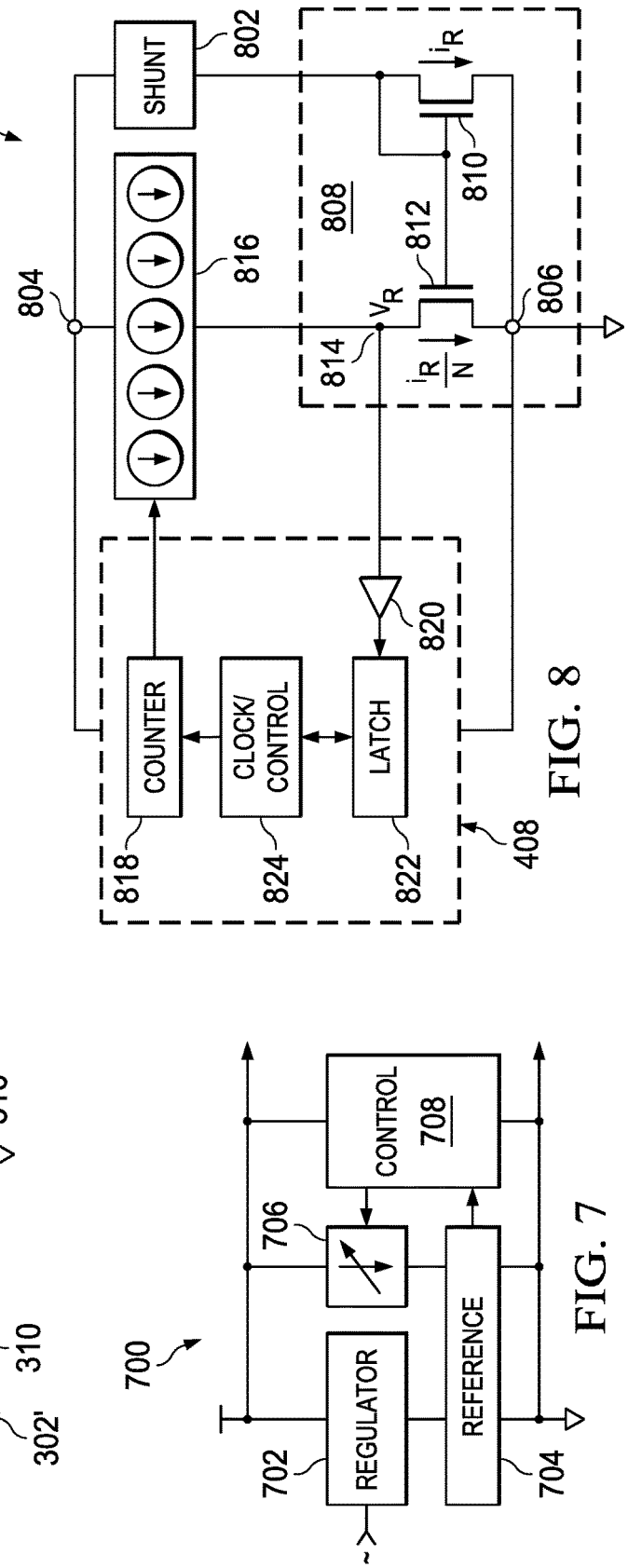
FIG. 8
FIG. 7

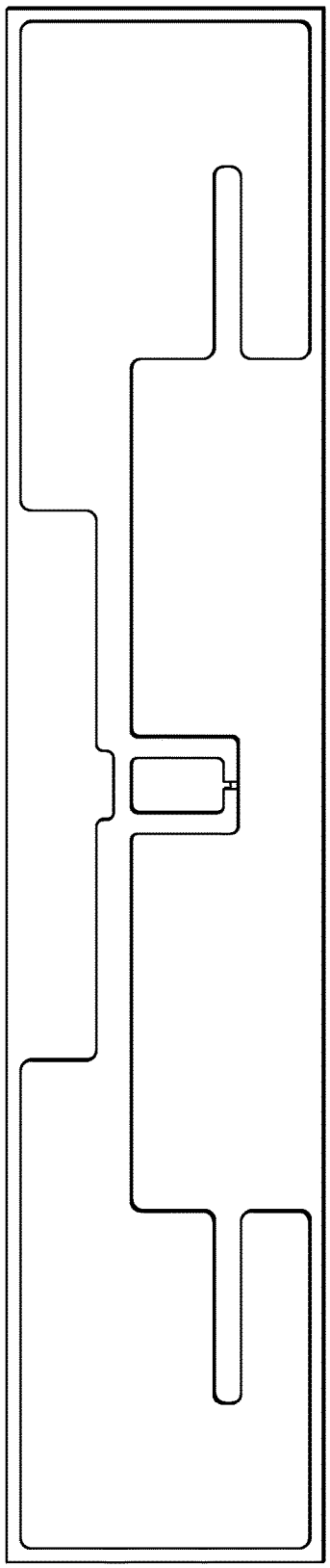
FIG. 59
| TAG | DRY | 1-SPRAY | 2-SPRAY |
|---|---|---|---|
| UNIVERSAL MOISTURE | 16.95 | 16.95 | 16.93 |
| DogBone | 18.26 | 18.10 | 17.76 |
FIG. 60
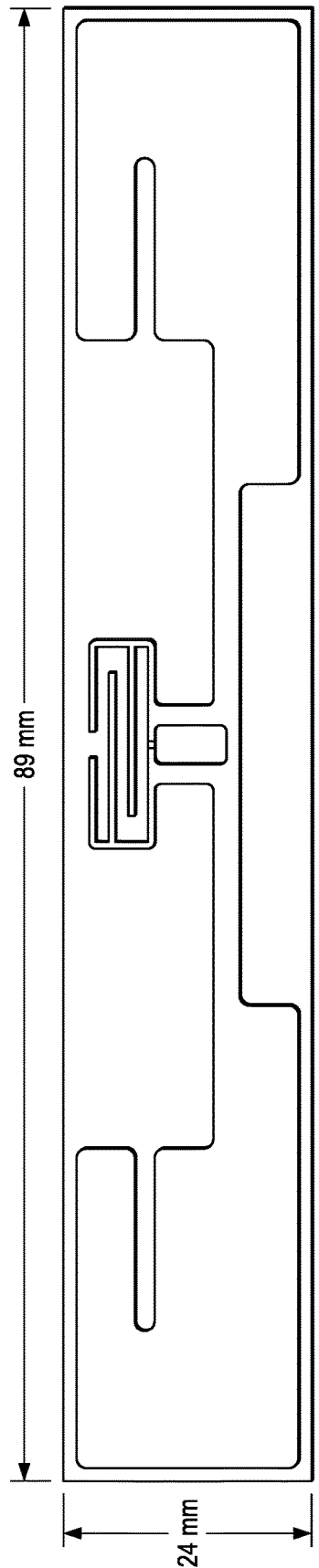
FIG. 61

RADIO FREQUENCY IDENTIFICATION (RFID) MOISTURE TAG(S) AND SENSORS WITH EXTENDED SENSING VIA CAPILLARIES

CROSS REFERENCE TO RELATED PATENTS

The present U.S. Utility patent application claims priority pursuant to 35 U.S.C. § 120 as a continuation of U.S. Utility application Ser. No. 15/443,050, entitled "Radio Frequency Identification (RFID) Moisture Tag(S) And Sensors With Extended Sensing Via Capillaries," filed Feb. 27, 2017, issuing as U.S. Pat. No. 10,069,205 on Sep. 4, 2018, which claims priority pursuant to 35 U.S.C. § 120 as a continuation of U.S. Utility application Ser. No. 14/879,088, entitled "Radio Frequency Identification (RFID) Moisture Tag(s) And Sensors With Extended Sensing Via Capillaries," filed Oct. 8, 2015, issued as U.S. Pat. No. 9,582,981 on Feb. 28, 2017, which claims priority pursuant to 35 U.S.C. § 119(e) to U.S. Provisional Application No. 62/061,257, entitled "Radio Frequency Identification (RFID) Moisture Tags and Sensors," filed Oct. 8, 2014, U.S. Provisional Application No. 62/079,369, entitled "Radio Frequency Identification (RFID) Moisture Tags and Sensors," filed Nov. 13, 2014, U.S. Provisional Application No. 62/147,890, entitled "Radio Frequency Identification (RFID) Moisture Tags and Sensors with Extended Sensing," filed Apr. 15, 2015, and U.S. Provisional Application No. 62/195,038, entitled "RFID Moisture Tags and Sensors with Extended Sensing via Capillaries," filed Jul. 21, 2015.

Additionally, the above identified applications and their subject matter are expressly incorporated herein by reference in their entirety and made part of the present U.S. Utility patent application for all purposes.

BACKGROUND OF THE INVENTION

1. Field of the Invention

The present invention relates generally to sensing a detectable environmental condition, and, in particular, to sensing moisture using an RFID system.

2. Description of the Related Art

In general, in an RF communication system, a single antenna structure is adapted to receive signals, the carrier frequencies ("$f_C$") of these signals can vary significantly from the resonant frequency ("$f_R$") of the antenna. The mismatch between $f_C$ and $f_R$ results in loss of transmitted power. In some applications, this may not be of particular concern, but, in others, such as in RF identification ("RFID") applications, such losses are of critical concern. For example, in a passive RFID tag, a significant portion of received power is used to develop all of the operating power required by the RFID tag's electrical circuits. In such an application, a variable impedance circuit can be employed to shift the $f_R$ of the RFID tag's receiver so as to better match the $f_C$ of the transmitter of the system's RFID reader. A single design that is useful in all systems is precluded by the lack of standards as to appropriate RFID system frequencies, and, the breadth of the available frequency spectrum is quite broad: Low Frequency ("LF"), including 125-134.2 kHz and 140-148.f kHz; High-Frequency ("HF") at 13.56 MHz; and Ultra-High-Frequency ("UHF") at 868-928 MHz. Compounding this problem is the fact that system manufacturers cannot agree on which specific $f_C$ is the best for specific uses, and, indeed, to prevent cross-talk, it is desirable to allow each system to distinguish itself from nearby systems by selecting different $f_C$ within a defined range.

Attempts have been made to improve the ability of the RFID tag's antenna to compensate for system variables, such as the materials used to manufacture the RFID tag. However, such structural improvements, while valuable, do not solve the basic need for a variable impedance circuit having a relatively broad tuning range.

Shown in FIG. 1 is an ideal variable impedance circuit 100. Circuit 100 comprised of a variable inductor 102, a variable capacitor 104 and a variable resistor. When used as a tank in a resonant system, the circuit 100 exhibits a quality factor ("Q") of:

$$Q = \frac{f_R}{\Delta f} = \frac{1}{R}\sqrt{\frac{L}{C}} \qquad [1]$$

where: Q=the quality factor of circuit 100;
$f_R$=the resonant frequency of circuit 100, measured in hertz;
$\Delta f$=the bandwidth of circuit 100, measured in hertz at −3 db
R=the resistance of resistor, measured in ohms;
L=the inductance of variable inductor 102, measured in henries; and
C=the capacitance of capacitor, measured in farads.

In such a system, the resonant frequency, $f_R$, of circuit 100 is:

$$f_R = \frac{1}{2\pi\sqrt{LC}} \qquad [2]$$

As is well known, the total impedance of circuit 100 is:

$$Z = \frac{Z_L Z_C}{Z_L + Z_C} \qquad [3]$$

where:
Z=the total impedance of circuit 100, measured in ohms;
$Z_L$=the impedance of variable inductor 102, measured in ohms; and
$Z_C$=the impedance of capacitor, measured in ohms.

As is known, the relationship between impedance, resistance and reactance is:

$$Z = R + jX \qquad [4]$$

where:
Z=impedance, measured in ohms;
R=resistance, measured in ohms;
j=the imaginary unit $\sqrt{-1}$; and
X=reactance, measured in ohms.

In general, it is sufficient to consider just the magnitude of the impedance:

$$|Z| = \sqrt{R^2 + X^2} \qquad [5]$$

For a purely inductive or capacitive element, the magnitude of the impedance simplifies to just the respective reactance's. Thus, for variable inductor 102, the reactance can be expressed as:

$$X_L = 2\pi f L \qquad [6]$$

Similarly, for capacitor, the reactance can be expressed as:

$$X_C = \frac{1}{2\pi f C} \quad [7]$$

Because the reactance of variable inductor 102 is in phase while the reactance of capacitor is in quadrature, the reactance of variable inductor 102 is positive while the reactance of capacitor is negative. Accordingly, a desired total impedance can be maintained if a change in inductive reactance is offset by an appropriate change in capacitive reactance.

Within known limits, changes can be made in the relative values of variable inductor 102, capacitor, and resistor to adjust the resonant frequency, $f_R$, of circuit 100 to better match the carrier frequency, $f_C$, of a received signal, while, at the same, maximizing Q.

In many applications, such as RFID tags, it may be economically desirable to substitute for variable inductor 102 a fixed inductor 202, as in the variable tank circuit 200 shown in FIG. 2. In general, in order to maximize Q in circuit 200.

The amplitude modulated ("AM") signal broadcast by the reader in an RFID system will be electromagnetically coupled to a conventional antenna, and a portion of the current induced in a tank circuit is extracted by a regulator to provide operating power for all other circuits. Once sufficient stable power is available, the regulator will produce, e.g., a power-on-reset signal to initiate system operation.

Tags based on conventional chips can be detuned by a variety of external factors, most commonly by proximity to liquids or metals. Such factors can change the impedance characteristics of a tag's antenna. When the tag chip has a fixed impedance, a mismatch between the chip and the antenna results, reducing the tag's performance.

BRIEF SUMMARY OF THE INVENTION

Embodiments of the present disclosure are directed to systems and methods that are further described in the following description and claims. Advantages and features of embodiments of the present disclosure may become apparent from the description, accompanying the drawings and claims.

Accordingly, the above problems and difficulties are obviated by embodiments of the present disclosure which provide an RF-based environmental moisture sensing system comprising one or more special antenna arrangements, and an RF transceiver.

The passive radio frequency identification (RFID) moisture sensor includes one or more antenna structures having a tail. The tail is operable to transport a disturbance such as, but not limited to fluid or moisture from a monitored location wherein the antenna has an impedance and varies with proximity to the disturbance. An integrated circuit couples to the antenna structure. This IC includes a power harvesting module operable to energize the integrated circuit, an impedance-matching engine coupled to the antenna, a memory module, and a wireless communication module. The impedance-matching engine may vary a reactive component to reduce a mismatch between the antenna impedance and the IC and produce an impedance value (sensor code) representative of the reactive component impedance. The memory module stores the impedance value (sensor code) until the wireless communication module communicates with an RFID reader and sends the impedance value/sensor code to the RFID reader. The RFID reader may then determine an environmental condition such as the presence of moisture or fluids at the tail of the RFID sensor and/or the magnitude (e.g. amount) of the environmental condition (e.g. moisture) and/or the change in such magnitude. This sensor may deploy several antenna and/or tails sensitive to unique disturbances. These tails may be used to monitor different locations as well as different types of fluids. In one particular embodiment, the disturbance is a fluid or moisture within the gutter of a vehicle body.

In another embodiment, the antenna arrangement includes an antenna coupled to a tail, the combination of the antenna and tail having an impedance. Further, the RF transceiver includes a number of tank circuit(s) operatively coupled to the antenna and having a selectively variable impedance. A tuning circuit is adapted to dynamically vary the impedance of the tank circuit, and to develop a first quantized value representative of the impedance of the tank circuit, wherein the first quantized value is a function of the modified antenna impedance.

Further embodiments provide a method for operating the first embodiment comprising the steps of first exposing the antenna/tail to a selected environmental condition such as but not limited to moisture or wetness. Next, the impedance of the tank circuit is dynamically varied to substantially match the modified antenna impedance. Processing the value of the dynamically varied antenna/tail impedance is then used to sense the environmental condition.

Another embodiment of the present disclosure provides an environmental sensing method for use in an RF system comprising the steps of: calibrating an RF sensor by developing a first calibration value indicative of an absence of a detectable quantity of a substance (or a known quantity or environmental parameter) and a second calibration value indicative of a presence of the detectable quantity of the substance (or a known quantity or environmental parameter); installing the sensor in a structure; exposing the structure to the substance; interrogating the sensor to retrieve a sensed value; and detecting the presence of the substance in the structure as a function of the sensed value relative to the first and second calibration values.

Yet another embodiment comprises multiple sensing engines that are located within a single integrated circuit (IC) or die that functions as a passive RFID tag. A generic sensing interface on the passive RFID tag provides additional flexibility and expanded general sensor applications. The present disclosure encompasses the ability for the passive RFID tag to (or based on the data supplied by the RFID tag) to make decisions based on multiple sensory inputs.

In yet another embodiment, the passive RFID tag/sensor includes one or more inductive loops, wherein the inductive loop(s) have a unique impedance; the unique impedance may be permanently altered in response to an environmental parameter proximate to the inductive loop(s). The quantized values generated in response to such an impedance change are used to indicate the occurrence of a physical event and/or the magnitude of such an occurrence. Such events include but are not limited to temperature changes, impacts, physical damage, exposure to moisture, humidity, or contaminates.

These embodiments and additional embodiments are described in more details in the detailed description.

BRIEF DESCRIPTION OF THE SEVERAL VIEWS OF THE DRAWINGS

Embodiments of the present disclosure may be more fully understood by a description of certain preferred embodiments in conjunction with the attached drawings in which:

FIG. 5 illustrates in block schematic form, another embodiment of a self-tuning engine;

FIG. 7 illustrates, in block diagram form, a field strength detector circuit constructed in accordance with an embodiment of the present disclosure;

FIG. 8 illustrates, in block schematic form, a more detailed embodiment of the field strength detector circuit shown in FIG. 7;

FIG. 17, comprising

FIG. 59 is a schematic of yet another embodiment a moisture tag antenna design in accordance with embodiments of the present disclosure;

FIG. 60 is a table comparing an embodiment a moisture tag antenna design with a prior art design in accordance with embodiments of the present disclosure;

FIG. 61 is a schematic of yet another embodiment a moisture tag antenna design in accordance with embodiments of the present disclosure;

Figure 1:
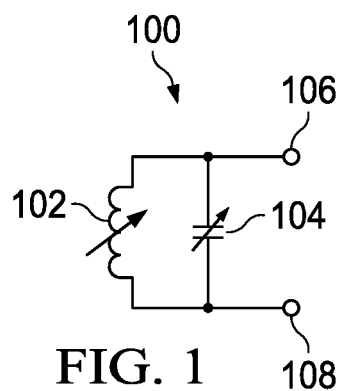
FIG. 1 is an ideal variable impedance circuit.
Figure 2:
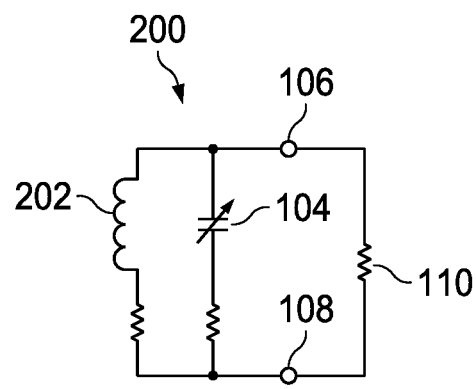
FIG. 2 is a second variable impedance circuit.

In the drawings, similar elements will be similarly numbered whenever possible. However, this practice is simply for convenience of reference and to avoid unnecessary proliferation of numbers, and is not intended to imply or suggest that the present disclosure requires identity in either function or structure in the several embodiments.

DETAILED DESCRIPTION OF THE INVENTION

Preferred embodiments of the present invention are illustrated in the FIGs., like numerals being used to refer to like and corresponding parts of the various drawings.

Throughout this description, the terms assert and negate may be used when referring to the rendering of a signal, signal flag, status bit, or similar apparatus into its logically true or logically false state, respectively, and the term toggle to indicate the logical inversion of a signal from one logical state to the other. Alternatively, reference may be made to the mutually exclusive Boolean states as logic_0 and logic_1. Of course, as is well known, consistent system operation can be obtained by reversing the logic sense of all such signals, such that signals described herein as logically true become logically false and vice versa. Furthermore, it is of no relevance in such systems which specific voltage levels are selected to represent each of the logic states.

Embodiments of the present disclosure provide various passive radio frequency identification (RFID) sensors. These passive RFID moisture sensors include an antenna coupled to a tail, a processing module, and a wireless communication module. The antenna and coupled tail have an impedance that may vary with an environment in which the antenna/tail is placed. The processing module couples to the antenna and has one or more self-tuning module(s) that may vary a reactive component impedance coupled to the antenna in order to change a system impedance. The system impedance including both the antenna impedance, tail impedance and the reactive component impedance. The self-tuning module(s) then produces an impedance value representative of the reactive component impedance. A memory module may store the impedance value which may then later is communicated to an RFID reader via the wireless communication module. The RFID reader then exchanges the impedance value representative of the reactive components of impedance with the RFID reader such that the RFID reader or another external processing unit may process the impedance value in order to determine environmental conditions at the antenna. These environmental conditions may include but are not limited to temperature, humidity, wetness, or proximity of the RFID reader to the passive RFID sensor.

In this disclosure, there will be references to several commonly used material types that RFID tags are affixed to for the purposes of detection and sensing. Some of the acronyms used are:

a. PTFE: Polytetrafluoroethylene (e.g. Teflon by DuPont)
b. PMMA: Poly(methyl methacrylate) (lightweight or shatter-resistant alternative to glass)
c. PET: Polyethylene terephthalate (a thermoplastic polymer resin of the polyester family and is used in bottles; synthetic fibers; beverage, food and other liquid containers; thermoforming applications; and engineering resins often in combination with glass fiber, e.g. Dacron, Terylene Laysan).

In this disclosure, the terms sensitivity or tag sensitivity, is used. Tag sensitivity is specified as the minimum power arriving at the tag necessary to communicate with the tag. The setup to measure the sensitivity consists of a reader, antenna, and the tag under test. The measurement proceeds by starting with a high power output from the reader and communicating with the tag. The power is then reduced until the tag stops communicating, so the minimum reader power to communicate is then known. This can generally be done with a binary search to speed things up. The process is repeated for each RFID channel.

The minimum reader power to communicate is not the tag sensitivity. If the reader's antenna is placed farther away, then more reader power is needed. Or, if a higher gain antenna is substituted, then lower reader power is needed. To get the tag sensitivity, the minimum reader power is adjusted to find the power arriving at the tag, and this power is the tag sensitivity:

tag sensitivity=minimum reader power+cable losses+ antenna gain+space loss where space loss takes into account the fact that the power density decreases as $1/r^2$. This is a relatively simple spreadsheet calculation that is well known in the art, and tools that support tag sensitivity measurements just have boxes where you fill in the cables losses, antenna gain, and distance from the antenna to the tag. The software then does the binary search for the minimum reader power, and it knows the frequency it is using, then it makes the needed adjustments and plots tag sensitivity vs. frequency.

Figure 3:
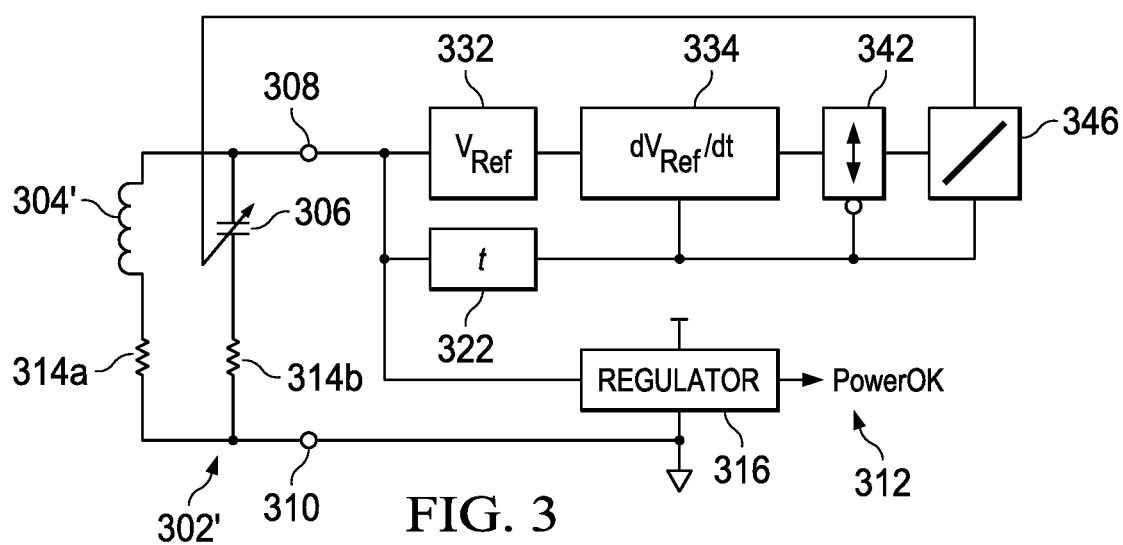
FIG. 3 illustrates in block schematic form, an embodiment of a self-tuning engine.

FIG. 3 illustrates in block schematic form, an embodiment of a self-tuning engine. In FIG. 3 the amplitude modulated ("AM") signal broadcast by the reader in an RFID system will be magnetically coupled to a conventional coil antenna comprising inductor 304', and a portion of the induced current is extracted via nodes 308 and 310 by a regulator 316 to produce operating power for all other circuits. Once sufficient stable power is available, regulator 316 will produce a PowerOK signal to initiate system operation (see, 402 and 404 in FIG. 4). If desired, a variable resistor (not shown) can be provided in parallel with inductor 304', generally between nodes 308 and 310, and regulator 316 can be constructed so as to automatically vary this resistance to control the gain of the tank circuit 302'.

Figure 4:
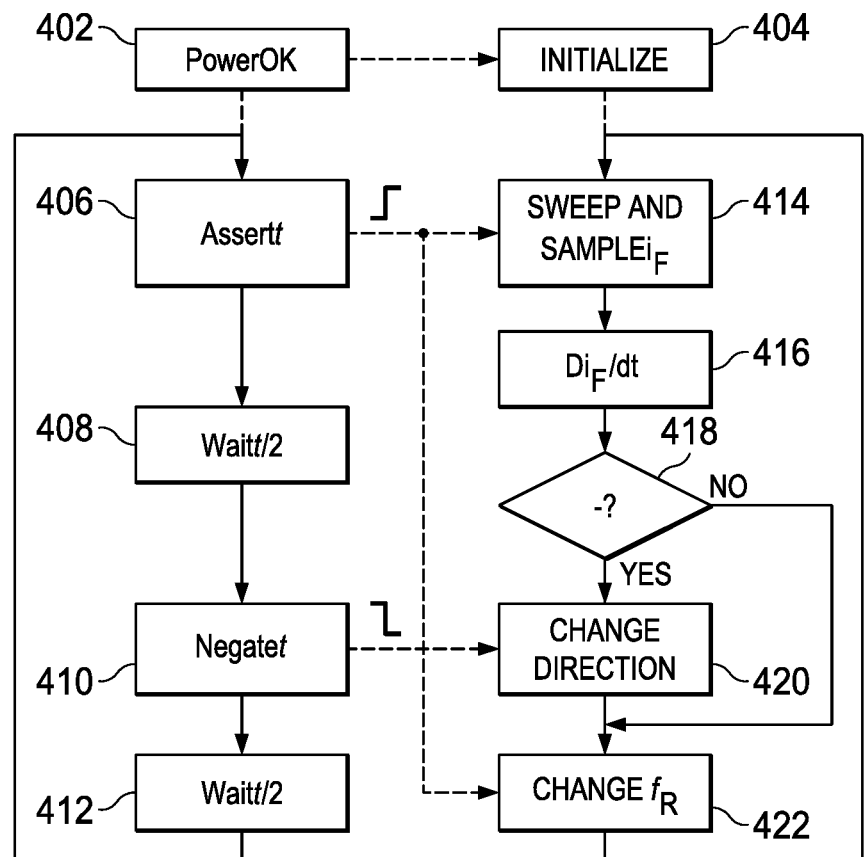
FIG. 4 illustrates in flow diagram form the sequencing of operations in the self-tuning engine shown in FIG. 3.

In response to the PowerOK signal, a timer 322 will periodically generate a timing pulse t (see, generally, 406, 408, 410, and 412 in FIG. 4). Preferably, the frequency of t pulses is a selected sub-multiple of the received signal, and the duty cycle is on the order of fifty percent (50%). However, as will be explained below, other duty cycles may be appropriate depending on the specific circuit elements selected to implement my invention.

In response to the PowerOK signal, a reference voltage generator 332 will continuously produce a reference voltage signal $V_{Ref}$ proportional to the voltage induced by the received signal between nodes 308 and 310. In response to the assertion of each t pulse, a differentiator 334 will save the then-current value of the $V_{Ref}$ signal (see, 414 in FIG. 4). Thereafter, differentiator 334 will continuously determine the polarity of the change of the previously saved value with respect to the then-current value of the $V_{Ref}$ signal (see, 416 in FIG. 4). If the polarity is negative, indicating that the current $V_{Ref}$ signal is lower than the previously-saved $V_{Ref}$ signal, differentiator 334 will assert a change direction signal; otherwise, differentiator 334 will negate the change direction signal (see, 418 in FIG. 4).

In response to each negation of t, a direction selector 342 will toggle between an up state and a down state if and only if differentiator 334 is then asserting the change direction signal; otherwise, selector 342 continues to maintain its current state (see, 420 in FIG. 4).

In response to the PowerOK signal, a ramp generator 346 will reset to a predetermined initial value (see, 404 in FIG. 4). Thereafter, in response to each assertion of t, generator 346 will selectively change the value of capacitor 306, thereby changing the resonant frequency $f_R$ of circuit 302' (see, 422 in FIG. 4). Preferably, the initial value for generator 346 is selected such that the initial resonant frequency $f_R$ of circuit 302' will approximate the anticipated carrier frequency $f_C$ of the received signal, thereby assuring convergence with a minimal number of re-tuning cycles. Although the initial value can be established using any of several known non-volatile techniques, including hard wiring or any of a variety of read-only-memory (ROM) structures, re-writable mechanisms, such as a flash or other electrically-programmable ROM structure are preferable. Using the latter, it would be a simple matter to construct regulator 316 so as to provide a PowerLoss signal when the level of available power drops to a predetermined minimum, and then, in response to the PowerLoss signal, to copy the current value in generator 346 into the memory. Upon next receiving the PowerOK signal, the generator 346 will resume operation at the stored value, potentially reducing convergence time.

After each change in the resonant frequency $f_R$ of circuit 302', circuit 312 again determines the polarity of change of $V_{Ref}$. If the polarity is found to be positive, the resonant frequency $f_R$ is converging toward the carrier frequency $f_C$, so the direction of change is correct. However, if the polarity is found to be negative, the resonant frequency $f_R$ is diverging from the carrier frequency, and the direction of change must be reversed. During operation, circuit 312 will selectively vary the value of capacitor 306 so that the resonant frequency $f_R$ of tank circuit 302' converges toward the carrier frequency $f_C$ of the received signal. Thus, if the polarity is found to be positive, circuit 312 will continue to vary the value of capacitor 306 in the currently-selected direction, say, for example, "up"; but, if the polarity is found to be negative, circuit 312 will switch the direction in which the value of capacitor 306 is varied, i.e., from "up" to "down", and begin varying the value of capacitor 6 in the newly-selected direction, now "down". In this manner, circuit 312 is able to converge the resonant frequency $f_R$ toward the carrier frequency $f_C$ regardless of whether or not the resonant frequency is initially higher or lower than the carrier frequency.

In the current embodiment, it is irrelevant which direction is initially selected by selector 342, as circuit 312 will quickly detect divergence and reverse the state of selector 342. However, if desired, a predetermined initial direction can be selected during initialization using conventional means.

It is to be expected that, as difference between the resonant frequency $f_R$ of tank circuit 302' and the carrier frequency $f_C$ of the received signal becomes relatively small, the ability of differentiator 334 to detect polarity changes will be significantly diminished. At such time, circuit 312 will tend to seek, i.e., changing tuning direction on each t. Additional circuitry could be easily added to detect this condition and to, for example, significantly decrease the operating frequency of timer 322 or, if desired, cease operation.

Another embodiment of a self-tuned engine that is digitally based is shown in FIG. 5. Thus, for example, in the digital circuit 500 shown in FIG. 5, timer 322 could comprise a clock 502 and an up/down-counter 504 adapted to continuously negate the t signal while down-counting to predetermined minimum value and then to continuously assert the t signal while up-counting to a predetermined maximum value, the counter 504 automatically reversing count direction upon reaching the predetermined minimum/maximum values. $V_{Ref}$ generator 332 could be implemented using a full-wave rectifier 506 and a low-pass filter 508, while differentiator 334 could comprise a comparator 510 with its positive input adapted to receive the current value of $V_{Ref}$ and its negative input adapted to receive the previous value of $V_{Ref}$ captured and saved by a sample-and-hold 512. Finally, selector 342 can be a simple toggle latch 514, while generator 346 could be an n-bit, bidirectional edge-triggered shift register 516. In response to the assertion of the PowerOK signal, shift register 516 will preferably initialize the high-order half of the n-bits to logic_0, and the low-order half to logic_1; in response to the leading-edge of the t signal (i.e., upon each assertion of t), shift register 516 will shift either left or right, depending on the state of toggle latch 514. Thus, to increase frequency, register 516 would perform a right-shift with a left fill of logic_0; whereas to decrease frequency, register 516 would perform a left-shift with a right-fill of logic_1.

When comparator 510 negates the change direction signal, the resonant frequency of circuit 302" is converging on the carrier frequency of the received signal; whereas, when comparator 510 asserts the change direction signal, the resonant frequency of circuit 302" is diverging from the carrier frequency of the received signal. Thus, for example, if the old value held in sample-and-hold 512 is less than the new value provided by the filter 508, comparator 510 will negate the change direction signal, indicating that register 516 is shifting in the correct direction to achieve convergence; under this condition, toggle 514 will not toggle. On the other hand, if the old value held in sample-and-hold 512 is greater than the new value provided by the filter 508, comparator 510 will assert the change direction signal, indicating that register 516 is not shifting in the correct direction to achieve convergence; under this condition, toggle 514 will toggle.

In the embodiment shown in FIG. 5, it is preferable but not necessary to select the minimum anticipated settling time of the sample-and-hold 512 as the minimum duration of the negated portion of each t pulse. For the period of t, it is preferable but not necessary to select the minimum anticipated settling time of the tank circuit 302' to each variation in tank capacitance. In such an arrangement, the negated portion of each t pulse will be relatively small with respect to the asserted portion. In general, this arrangement should enable circuit 500 to "re-tune" the tank circuit 302' as quickly as the various circuit components are able to detect, and then respond to, the resulting changes in $V_{Ref}$.

Conventional dipole design for RFID tags use a small inductive loop to tune out the input capacitance of the RFID IC. By altering a conductive material near this inductive tuning loop, the inductance depends on the properties of the conductive material. The self-tuning engine detects the change in inductance and adjusts its input capacitance to maintain peak power to the die. The change in capacitance can be read from the die as a sensor code using the standard EPC read command. The sensor code reflects the change in the conductive material proximate to the inductive loop.

In general, prior disclosures have focused primarily on quantizing the voltage developed by the tank circuit as the primary means of matching the JR of the tank circuit to the transmission frequency, $f_C$, of the received signal. However, this voltage quantization is, at best, indirectly related to received signal strength. Other effective and efficient methods may quantize the received field strength as a function of induced current. In particular, a method and apparatus adapted to develop this field quantization in a form and manner that is suitable for selectively varying the input impedance of the receiver circuit to maximize received power, especially during normal system operation. Additionally, in light of the power sensitive nature of RFID systems, disclosed methods and apparatus of the present disclosure vary the input impedance with a minimum power loss.

Figure 6:
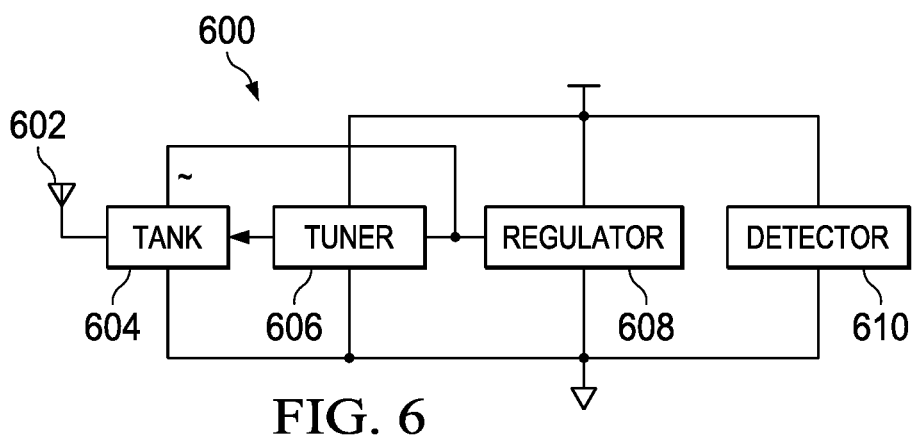
FIG. 6 illustrates, in block diagram form, an RF receiver circuit having a field strength detector constructed in accordance with an embodiment of the present disclosure.

While prior disclosures use methods to sense environmental changes to which the RFID tag is exposed, the present disclosure, illustrated through various embodiments, provides for new sensing methods adapted to operate in a variety of environments that are more efficient, compact, adaptable and self-tuning Shown in FIG. 6 is an RF receiver circuit 600 suitable for use in an RFID application. Note that the Tank 604, Tuner 606 and Regulator 608 can be embodied by the structures shown in FIG. 3 or FIG. 5. An RF signal electromagnetically coupled to an antenna 602 is received via a tank circuit 604, the response frequency, $f_R$, of which is dynamically varied by a tuner 606 to better match the transmission frequency, $f_C$, of the received RF signal, thus obtaining a maximum power transfer. In particular, the RMS voltage induced across the tank circuit 604 by the received RF signal is quantized by tuner 606 and the developed quantization employed to control the impedance of the tank circuit 604 as explained above. Also, the unregulated, AC current induced in the tank circuit by the received RF signal is conditioned by a regulator 608 to provide regulated DC operating power to the receiver circuit 600. This allows the tank circuit 604 to function as a power harvesting circuit wherein the power may be stored in a capacitor, charge pump or other like circuit. In accordance with our present disclosure, we now provide a field strength detector 610, also known as a power detector, adapted to develop a field-strength value as a function of the field strength of the received RF signal. As indicated in FIG. 6, field strength detector 610 is adapted to cooperate with the regulator 608 in the development of the field-strength value. Field strength detector 610 can be adapted to cooperate with the tuner 606 in controlling the operating characteristics of the tank circuit 604.

In general, in an RF communication system, an antenna structure is used to receive signals, the carrier frequencies ("$f_C$") of which may vary significantly from the natural resonant frequency ("$f_R$") of the antenna. It is well known that mismatch between $f_C$ and $f_R$ results in loss of transmitted power. In some applications, this may not be of particular concern, but, in others, such as in RF identification ("RFID") applications, such losses are of critical concern. For example, in a passive RFID tag, a significant portion of received power is used to develop all of the operating power required by the RFID tag's electrical circuits. In such an application, a variable impedance circuit may be employed to shift the $f_R$ of the RFID tag's receiver so as to better match the $f_C$ of the transmitter of the system's RFID reader.

In accordance with one embodiment of the present disclosure, the amplitude modulated ("AM") signal broadcast by the reader in an RFID system (or other CW source) are magnetically coupled to a conventional coil antenna comprising inductor, and a portion of the induced current is extracted via nodes by a regulator to produce operating power for all other circuits. Such a regulator may include a charge pump.

Shown by way of example in FIG. 7 is one possible embodiment of a field strength or power detector 700 (field strength detector 610 of FIG. 6) that is integrated into the sensor. This embodiment employs a shunt-type regulator 702 so that, during normal operation, the shunted 'excess' current can be used as a reference against which we develop the field-strength value. In this regard, reference module 704 produces a shunt current reference value proportional to the shunted current, and then develops a mirrored current reference value as a function of both the shunted current and a field strength reference current provided by a digitally-controlled current source 706. Preferably, once the tuner 606 has completed its initial operating sequence, whereby the $f_R$ of the tank circuit 604 has been substantially matched to the $f_C$ of the received signal, a digital control 708 initiates operation of the current source 706 at a predetermined, digitally-established minimum field strength reference current. After a predetermined period of time, control 708 captures the mirrored current reference value provided by the current reference module 704, compares the captured signal against a predetermined threshold value, and, if the comparison indicates that the field strength reference current is insufficient, changes, in accordance with a predetermined sequence of digital-controlled increments, the field strength reference current; upon the comparison indicating that the field strength reference current is sufficient, control 708 will, at least temporarily, cease operation.

In accordance with embodiments of the present disclosure, the digital field-strength value developed by control 708 to control the field strength current source 706 is a function of the current induced in the tank circuit 604 by the received RF signal. Once developed, this digital field-strength value can be employed in various ways. For example, it can be selectively transmitted by the RFID device (using conventional means) back to the reader (not shown) for reference purposes. Such a transaction can be either on-demand or periodic depending on system requirements. One embodiment distributes a plurality of RFID tag devices, perhaps randomly, throughout a restricted, 3-dimensional space, e.g., a loaded pallet. The reader is programmed to query, at an initial field strength, all tags "in bulk" and to command all tags that have developed a field-strength value greater than a respective field-strength value to remain 'silent'. By performing a sequence of such operations, each at an increasing field strength, the reader will, ultimately, be able to isolate and distinguish those tags most deeply embedded within the space; once these 'core' tags have been read, a reverse sequence can be performed to isolate and distinguish all tags within respective, concentric 'shells' comprising the space of interest. Although, in all likelihood, these shells will not be regular in either shape or relative volume, the analogy should still be applicable.

FIG. 8 illustrates one embodiment of a field strength detector 800. In general, shunt circuit 802 develops a substantially constant operating voltage level across supply node 804 and ground node 806. Shunt regulators of this type are well known in the art, and typically use zener diodes, avalanche breakdown diodes, diode-connected MOS devices, and the like.

As can be seen, current reference 704 of FIG. 7 may be implemented in the form of a current mirror circuit 808, connected in series with shunt circuit 802 between nodes 804 and 806. As is typical, current mirror circuit 808 comprises a diode-connected reference transistor 810 and a mirror transistor 812. If desired, a more sophisticated circuit such as a Widlar current source may be used rather than this basic two-transistor configuration. For convenience of reference, the current shunted by shunt circuit 802 via reference transistor 810 is designated as $i_R$; similarly, the current flowing through mirror transistor 812 is designated as $i_R/N$, wherein, as is known, N is the ratio of the widths of reference transistor 810 and mirror transistor 812.

Here, the field strength current source 816 is implemented as a set of n individual current sources, each connected in parallel between the supply node 804 and the mirror transistor 812. In general, field strength current source 816 is adapted to source current at a level corresponding to an n-bit digital control value developed by a counter 818. In the illustrated embodiment, wherein n=5, field strength current source 816 is potentially capable of sourcing thirty-two distinct reference current levels. We propose that the initial, minimum reference current level be selected so as to be less than the current carrying capacity of the mirror transistor 812 when the shunt circuit 802 first begins to shunt excess induced current through reference transistor 812; that the maximum reference current level be selected so as to be greater than the current carrying capacity of the mirror transistor 812 when the shunt circuit 802 is shunting a maximum anticipated amount of excess induced current; and that the intermediate reference current levels be distributed relatively evenly between the minimum and maximum levels. Of course, alternate schemes may be practicable, and, perhaps, desirable depending on system requirements.

Within control 818, a conventional analog-to-digital converter ("ADC") 820, having its input connected to a sensing node 814, provides a digital output indicative of the field strength reference voltage, $v_R$, developed on sensing node 814. In one embodiment, ADC 820 may comprise a comparator circuit adapted to switch from a logic_0 state to a logic_1 when sufficient current is sourced by field strength current source 816 to raise the voltage on sensing node 814 above a predetermined reference voltage threshold, $v_{th}$. Alternatively, ADC 820 may be implemented as a multi-bit ADC capable of providing higher precision regarding the specific voltage developed on sensing node 814, depending on the requirements of the system. Sufficient current may be characterized as that current sourced by the field strength current source 816 or sunk by mirror transistor 812 such that the voltage on sensing node 814 is altered substantially above or below a predetermined reference voltage threshold, $v_{th}$. In the exemplary case of a simple CMOS inverter, $v_{th}$ is, in its simplest form, one-half of the supply voltage (VDD/2).

Those skilled in the art will appreciate that $v_{th}$ may by appropriately modified by altering the widths and lengths of the devices of which the inverter is comprised. In the exemplary case a multi-bit ADC, $v_{th}$ may be established by design depending on the system requirements and furthermore, may be programmable by the system.

In the illustrated embodiment, a latch 822 captures the output state of ADC 820 in response to control signals provided by a clock/control circuit 824. If the captured state is logic_0, the clock/control circuit 824 will change counter 818 to change the reference current being sourced by field strength current source 816; otherwise clock/control circuit 824 will, at least temporarily, cease operation. However, notwithstanding, the digital field-strength value developed by counter 818 is available for any appropriate use, as discussed above.

The present disclosure also provides a method and apparatus for a self-tuning engine with, optionally, the ability to detect RF field strength for use generally in RFID tags and sensors. A field strength reference generator develops a field strength reference current as a function of a field strength of a received RF signal; and a field strength quantizer develops a digital field strength value indicative of the field strength reference current. In one embodiment, detected field strength is used to dynamically vary the impedance of a tank circuit via an optimization loop that includes a search process whereby, over time, induced current is maximized. A similar process, as explained above is used for the self-tuning engine. Incorporating dithering into the process will be further discussed with reference to FIGS. 26 and 31A-31D.

Figure 9:
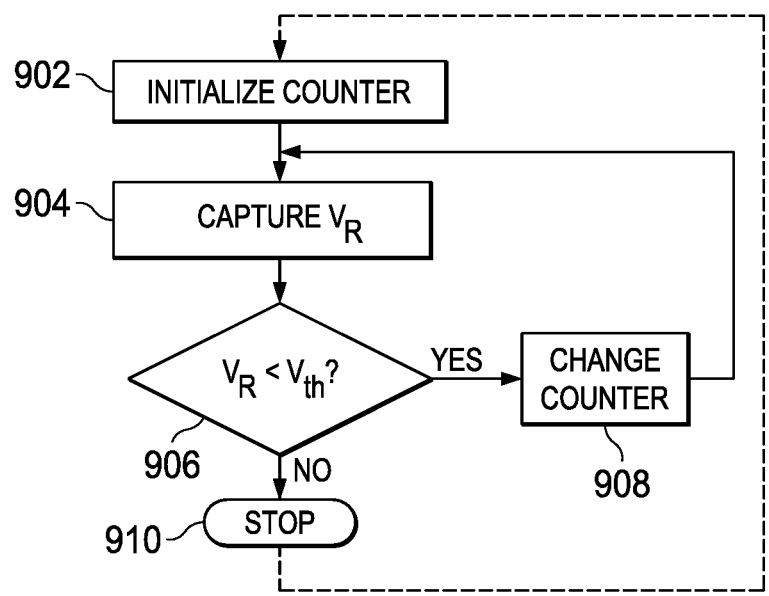
FIG. 9 illustrates, in flow diagram form, the sequencing of operations in the field strength detector circuit shown in FIG. 5.

By way of example, FIG. 9 illustrates one possible general operational flow of a field strength detector in accordance with embodiments of the present disclosure. Upon activation, counter 818 is set to its initial digital field-strength value (step 902), thereby enabling field strength current source 816 to initiate reference current sourcing at the selected level. After an appropriate settling time, the field strength reference voltage, $v_R$, developed on sensing node 814 and digitized by ADC 820 is captured in latch 822 (step 904). If the captured field strength reference voltage, $v_R$, is less than (or equal to) the predetermined reference threshold voltage, $v_{th}$, clock/control 824 will change counter 818 (step 906). This process will repeat, changing the reference current sourced by field strength current source 816 until the captured field strength reference voltage, $v_R$, is greater than the predetermined reference threshold voltage, $v_{th}$, (at step 908), at which time the process will stop (step 910). As illustrated, this sweep process can be selectively reactivated as required, beginning each time at either the initial field-strength value or some other selected value within the possible range of values as desired.

Figure 10:
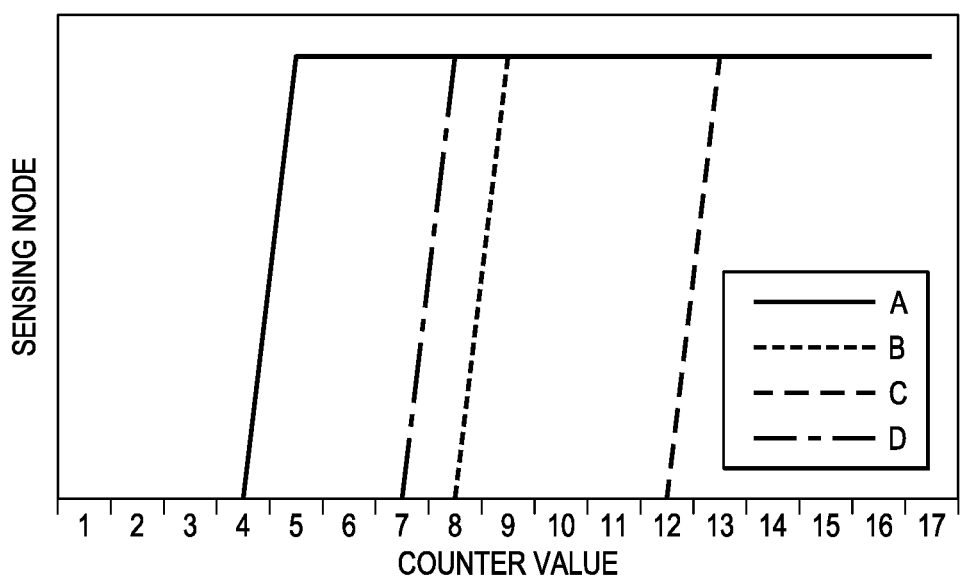
FIG. 10 illustrates, in graph form, the response of the field strength detector circuit shown in FIG. 6 to various conditions.

The graph provided in FIG. 10 depicts several plots of the voltage developed on sensing node 814 as the field strength detector circuit 700 sweeps the value of counter 818 according to the flow illustrated in FIG. 9. As an example, note that the curve labeled "A" in FIG. 10 begins at a logic_0 value when the value of counter 818 is at a minimum value such as "1" as an exemplary value. Subsequent loops though the sweep loop gradually increase the field strength reference voltage on sensing node 814 until counter 818 reaches a value of "4" as an example. At this point, the "A" plot in FIG. 10 switches from a logic_0 value to a logic_1 value, indicating that the field strength reference voltage, $v_R$, on sensing node 814 has exceeded the predetermined reference threshold voltage, $v_{th}$. Other curves labeled "B" through "D"

depict incremental increases of reference currents, ix, flowing through reference device, resulting in correspondingly higher mirrored currents flowing through the mirror device. This incrementally higher mirror current requires field strength current source to source a higher current level which in turn corresponds to higher values in counter 818. Thus, it is clear that embodiments of the present disclosure are adapted to effectively and efficiently develop a digital representation of the current flowing through sensing node 814 that is suitable for any appropriate use.

Figure 11:
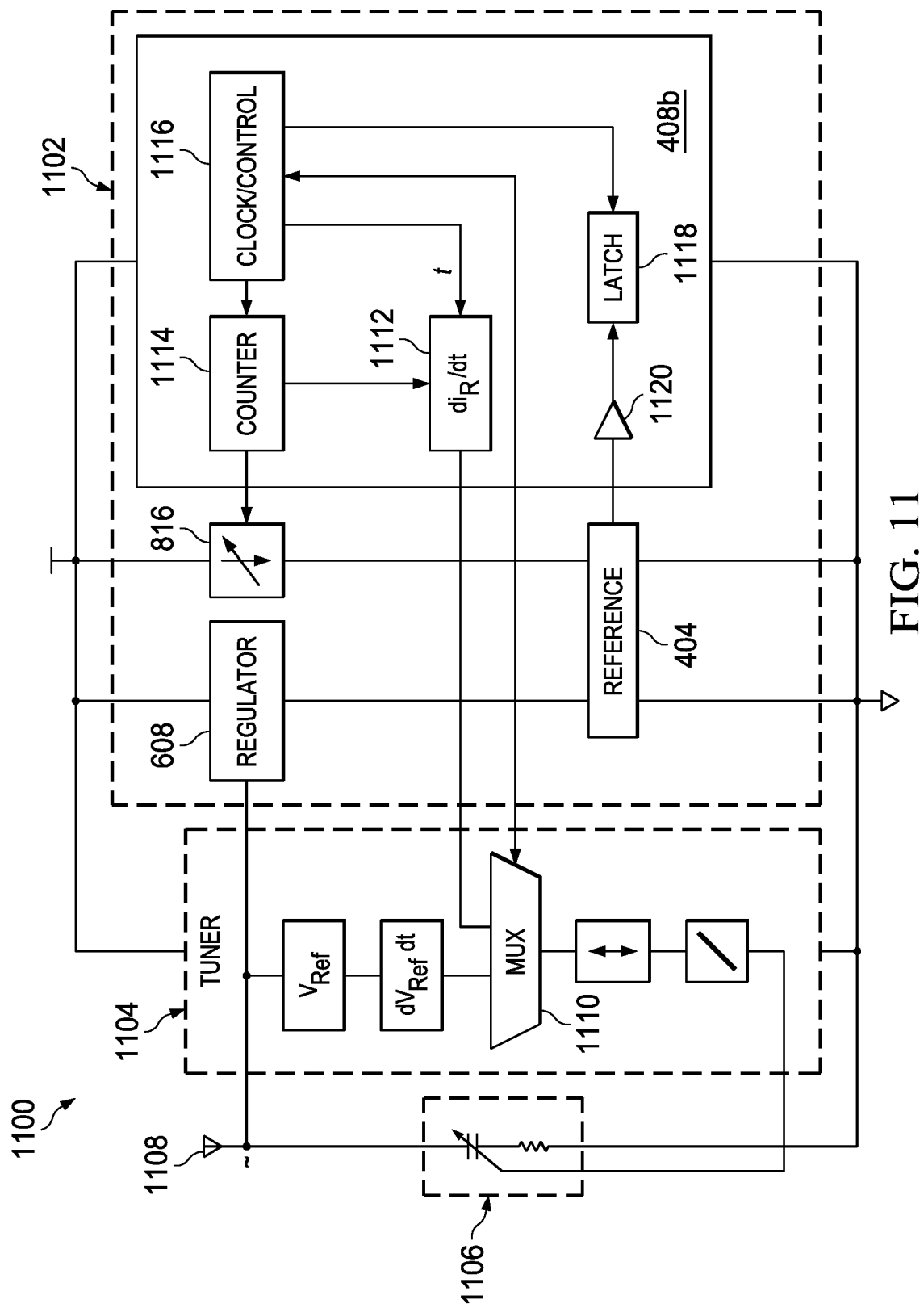
FIG. 11 illustrates, in block schematic form, an RF receiver circuit constructed in accordance with another embodiment of the present disclosure.

One such use, as discussed earlier, of field strength detector 610 is to cooperate with tuner 606 in controlling the operating characteristics of the tank circuit 604. FIG. 11 illustrates one possible embodiment where receiver circuit 1100 uses a field strength detector 1102 specially adapted to share with tuner 1104 the control of the tank circuit 1106. Dynamically tuning, via tuner 1104, the tank circuit 1106 allows one to dynamically shift the $f_R$ of the tank circuit 1106 to better match the $f_C$ of the received RF signal at antenna 1108. FIG. 11 adds a multiplexer 1110 to tuner 1104 to facilitate shared access to the tuner control apparatus. Shown in FIG. 4 is the operational flow of field strength detector 1100 upon assuming control of tank circuit 1106.

Figure 12:
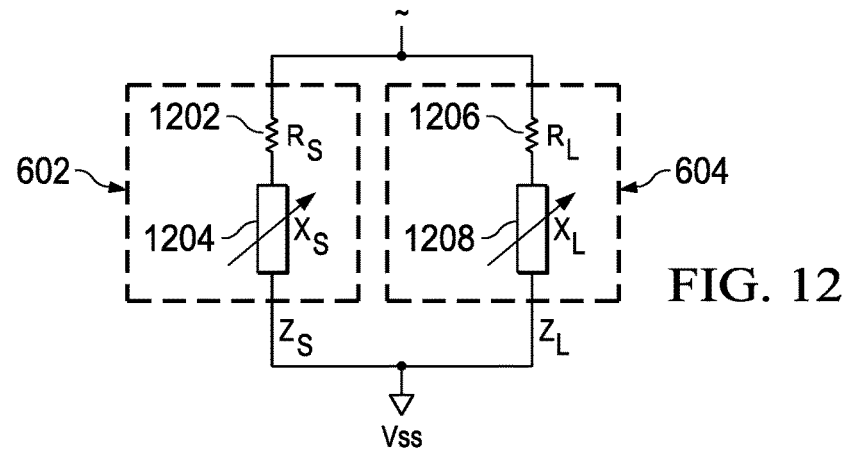
FIG. 12 illustrates, in block schematic form, an alternative representation of the impedance represented by the antenna and the tank circuit of the exemplary RFID receiver circuit.
Figure 13:
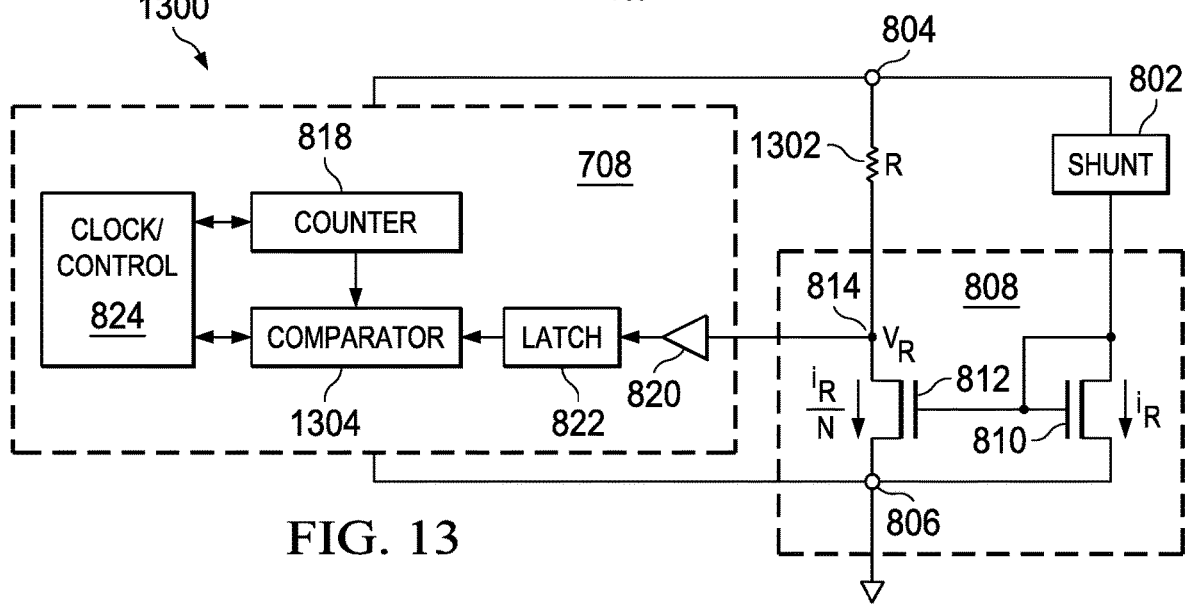
FIG. 13 illustrates, in block schematic form, an alternative exemplary embodiment of the field strength detector circuit shown in FIG. 8.
Figure 14:
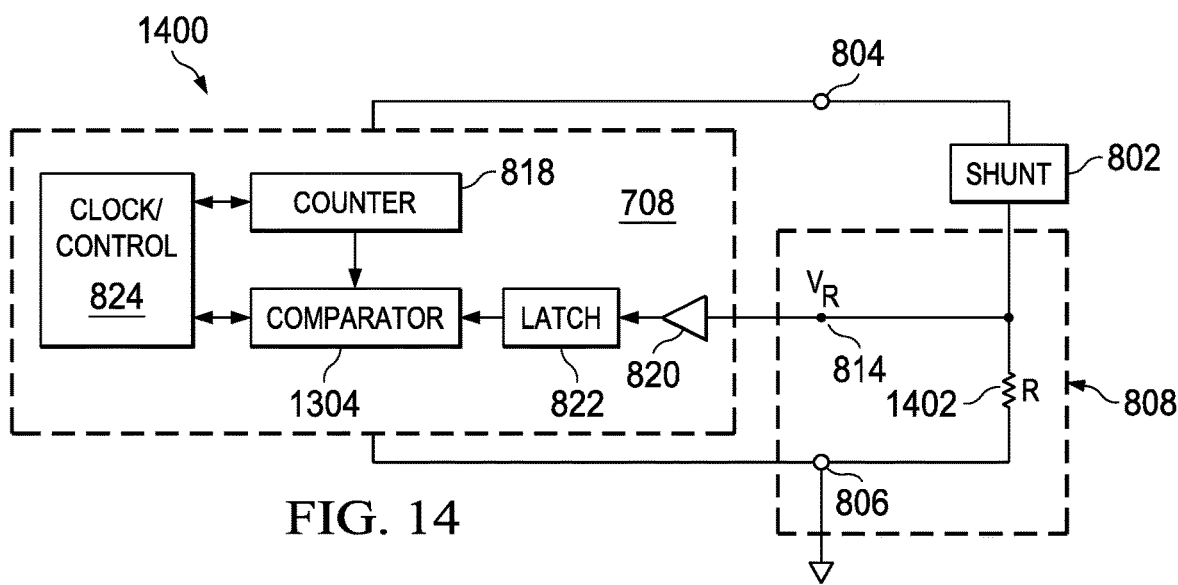
FIG. 14 illustrates, in block schematic form, an alternative exemplary embodiment of the field strength detector circuit shown in FIG. 8

In context of this particular use, once tuner 1104 has completed its initial operating sequences, and field strength detector 1100 has performed an initial sweep (as described above and illustrated in FIG. 4) and saved in a differentiator 1112 a base-line field-strength value developed in counter 1114, clock/control 1116 commands multiplexer 1110 to transfer control of the tank circuit 1106 to field strength detector 1102 (all comprising step 404 in FIG. 4). Upon completing a second current sweep, differentiator 1112 will save the then-current field-strength value developed in the counter 1114 (step 414). Thereafter, differentiator 1112 will determine the polarity of the change of the previously saved field-strength value with respect to the then-current field-strength value developed in counter 1114 (step 416). If the polarity is negative (step 418), indicating that the current field-strength value is lower than the previously-saved field-strength value, differentiator 1112 will assert a change direction signal; otherwise, differentiator 1112 will negate the change direction signal (step 420). In response, the shared components in tuner 1104 downstream of the multiplexer 1110 will change the tuning characteristics of tank circuit 1106 (step 422). Now, looping back (to step 414), the resulting change of field strength, as quantized is the digital field-strength value developed in counter 1114 during the next sweep (step 414), will be detected and, if higher, will result in a further shift in the $f_R$ of the tank circuit 1106 in the selected direction or, if lower, will result in a change of direction (step 420). Accordingly, over a number of such 'seek' cycles, embodiments of the present disclosure will selectively allow the receiver 1100 to maximize received field strength even if, as a result of unusual factors, the $f_R$ of the tank circuit 1106 may not be precisely matched to the $f_C$ of the received RF signal, i.e., the reactance of the antenna is closely matched with the reactance of the tank circuit, thus achieving maximum power transfer. In an alternative embodiment, it would be unnecessary for tuner 1104 to perform an initial operating sequence. Rather, field strength detector 1102 may be used exclusively to perform both the initial tuning of the receiver circuit 1100 as well as the subsequent field strength detection. Note that the source impedance of antenna 1108 and load impedance of tank circuit 1106 may be represented alternatively in schematic form as in FIG. 12, wherein antenna 1108 is represented as equivalent source resistance $R_S$ 1202 and equivalent source reactance $X_S$ 1204, and tank circuit 1106 is represented as equivalent load resistance $R_L$ 1206 and equivalent, variable load reactance $X_L$ 1208.

In another embodiment, embodiments of the present disclosure may be adapted to sense the environment to which a tag is exposed, as well as sensing changes to that same environment. The auto-tuning capability of tuner 606 acting in conjunction with tank circuit 604 detects antenna impedance changes (in addition to the embodiments illustrated in FIG. 3, FIG. 4, and FIG. 5). These impedance changes may be a function of environmental factors such as proximity to interfering substances, e.g., metals or liquids, as well as a function of a reader or receiver antenna orientation. Likewise, as disclosed herein, field strength (i.e., received power) detector may be used to detect changes in received power (i.e., field strength) as a function of, for example, power emitted by the reader, distance between tag and reader, physical characteristics of materials or elements in the immediate vicinity of the RFID tag and reader, or the like. Sensing the environment or, at least, changes to the environment is accomplished using one or both of these capabilities.

Figure 15:
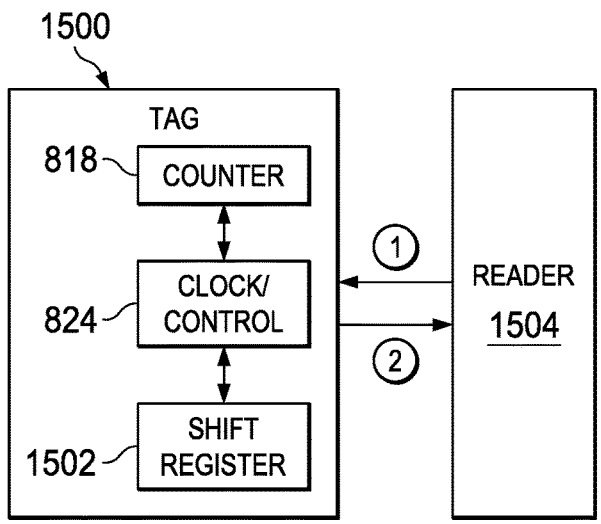
FIG. 15 illustrates, in block schematic form, an exemplary RFID sub-system containing tag and reader.

As an example, the RFID tag 1500 of FIG. 15, contains both a source tag antenna (not shown, but see, e.g., FIG. 8) and a corresponding load chip tank circuit 604 (not shown, but see, e.g., FIG. 8). Each contains both resistive and reactive elements as discussed previously (see, e.g., FIG. 12). Tag 1500 containing such a tank circuit 604 mounted on a metallic surface will exhibit antenna impedance that is dramatically different than the same tag 1500 in free space or mounted on a container of liquid. Shown in Table 1 are exemplary values for impedance variations in both antenna source resistance 1202 as well as antenna source reactance 1204 as a function of frequency as well as environmental effects at an exemplary frequency.

TABLE 1

| Antenna Impedance Variations | | | | | | | | |
|---|---|---|---|---|---|---|---|---|
| | 860 MHz | | 870 MHz | | 880 MHz | | 890 MHz | |
| | Rs, ☐ | Xs, ☐ | Rs, ☐ | Xs, ☐ | Rs, ☐ | Xs, ☐ | Rs, ☐ | Xs, ☐ |
| In Air | 1.3 | 10.7 | 1.4 | 10.9 | 1.5 | 11.2 | 1.6 | 11.5 |
| On Metal | 1.4 | 10.0 | 1.5 | 10.3 | 1.6 | 10.6 | 1.7 | 10.9 |
| On Water | 4.9 | 11.3 | 1.8 | 11.1 | 2.4 | 11.7 | 2.9 | 11.5 |
| On Glass | 1.8 | 11.1 | 2.0 | 11.4 | 2.2 | 11.7 | 2.5 | 12.0 |
| On Acrylic | 1.4 | 10.6 | 1.6 | 11.1 | 1.7 | 11.4 | 1.9 | 11.7 |

TABLE 1-continued

| | Antenna Impedance Variations | | | | | | | |
|---|---|---|---|---|---|---|---|---|
| | 900 MHz | | 910 MHz | | 920 MHz | | 930 MHz | |
| | Rs, □ | Xs, □ | Rs, □ | Xs, □ | Rs, □ | Xs, □ | Rs, □ | Xs, □ |
| In Air | 1.8 | 11.8 | 2.0 | 12.1 | 2.2 | 12.4 | 2.4 | 12.8 |
| On Metal | 1.9 | 11.2 | 2.1 | 11.6 | 2.3 | 12.0 | 2.6 | 12.4 |
| On Water | 2.5 | 12.3 | 3.0 | 12.7 | 5.8 | 14.1 | 9.1 | 13.2 |
| On Glass | 2.8 | 12.4 | 3.2 | 12.8 | 3.7 | 13.2 | 4.2 | 13.6 |
| On Acrylic | 2.0 | 12.1 | 2.3 | 12.4 | 2.5 | 12.8 | 2.8 | 13.2 |

The tuner circuit 606 of embodiments of the present disclosure automatically adjusts the load impendence by adjusting load reactance 1208 to match source antenna impedance represented by source resistance 1202 and source reactance 1204. As previously disclosed, matching of the chip load impedance and antenna source impedance can be performed automatically in order to achieve maximum power transfer between the antenna and the chip. A digital shift register 1502 allows selectively changing the value of the load reactive component 1208 (see, e.g., FIG. 12), in the present case a variable capacitor, until power transfer is maximized. This digital value of the matched impendence may be used either internally by the RFID tag 1500, or read and used by the reader 1504, to discern relative environmental information to which the RFID tag 1500 is exposed. For example, tag 1500 may contain a calibrated look-up-table within the clock/control circuit 824 which may be accessed to determine the relevant environmental information. Likewise, a RFID reader 1504 may issue commands (see transaction 1 in FIG. 15) to retrieve (see transaction 2 in FIG. 15) the values contained in digital shift register 1502 via conventional means, and use that retrieved information to evaluate the environment to which tag 1500 is exposed. The evaluation could be as simple as referencing fixed data in memory that has already been stored and calibrated, or as complex as a software application running on the reader or its connected systems for performing interpretive evaluations.

Likewise, consider a tag 1500 containing a field strength (i.e., received power) detector wherein the method of operation of the system containing the RFID tag 1500 calls for field strength detector to selectively perform a sweep function and developing the quantized digital representation of the current via the method discussed earlier. As illustrated in FIG. 15, counter 818 will contain the digital representation developed by our field strength detector 610 of the RF signal induced current, and may be used either internally by the RFID tag 1500, or read and used by the reader 1504, to discern relative environmental information to which the RFID tag is exposed. For example, reader 1504 may issue a command to the RFID tag 1500 to activate tuner 606 and/or detector 610 and, subsequent to the respective operations of tuner 606 and/or detector 310, receive the digital representations of either the matched impedance or the maximum current developed during those operations. Once again, this digital value of the field strength stored in the counter 818 may be used either internally by the RFID tag 1500, or read and used by the reader 1504, to discern relative environmental information to which the RFID tag 1500 is exposed. For example, tag 1500 may contain a calibrated look-up-table within the clock and control block 824 which may be accessed to determine the relevant environmental information. Likewise, a RFID reader may issue commands to retrieve the values contained in digital shift register 1502, and use that retrieved information to evaluate the environment to which tag 1500 is exposed. The evaluation could be as simple as referencing fixed data in memory that has already been stored and calibrated, or as complex as a software application running on the reader or its connected systems for performing interpretive evaluations. Thus, the combining of the technologies enables a user to sense the environment to which a tag 1500 is exposed as well as sense changes to that same environment.

Some environmental factors can change the effective impedance of the RFID antenna. Thus, it is possible to dynamically retune the tank circuit 604 or other like impedance to compensate for the environmentally-induced change in impedance by systematically changing the digital tuning parameters of tank circuit 604. By characterizing the antenna impedance as a function of various factors, one can develop an estimate of the relative change in the environmental factor as a function of the relative change in the digital tuning parameters of the tank circuit 604.

Figure 16:
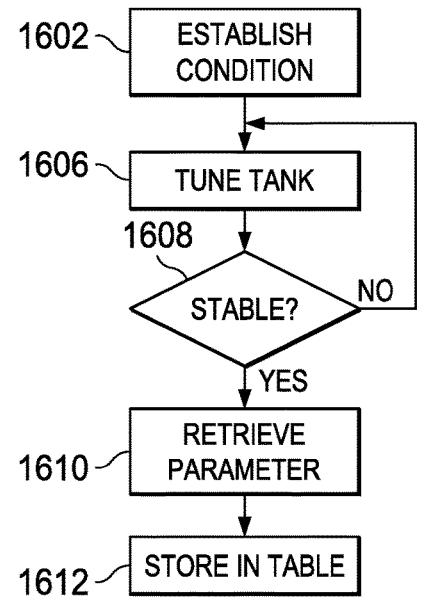
FIG. 16 illustrates, in flow diagram form, the sequencing of the operations in developing a reference table associating tank tuning parameters with system frequency.

As can be seen in Table 1, above, it is possible to develop, a priori, a reference table storing information relating to a plurality of environmental reference conditions. Thereafter, in carefully controlled conditions wherein one and only one environmental condition of interest is varied (see, FIG. 16), an operational tag 1500 is exposed to each of the stored reference conditions (step 1602) and allowed to complete the tank tuning process. (recursive steps 1606 and 1608. After tuning has stabilized, the RFID tag 1500 can be interrogated (step 1610), and the final value in the shift register 1502 retrieved (step 1610). This value is then stored in the reference table in association with the respective environmental condition (step 1612). The resulting table might look like this:

TABLE 2

| | Tuning Parameters vs. Frequency | | | | | | | |
|---|---|---|---|---|---|---|---|---|
| | 860 MHz | 870 MHz | 880 MHz | 890 MHz | 900 MHz | 910 MHz | 920 MHz | 930 MHz |
| In Air | 25 | 21 | 16 | 12 | 8 | 4 | 0 | 0* |
| On Metal | 31 | 27 | 22 | 17 | 12 | 8 | 3 | 0 |
| On Water | 20 | 19 | 12 | 12 | 4 | 0 | 0* | 0* |

TABLE 2-continued

Tuning Parameters vs. Frequency

|  | 860 MHz | 870 MHz | 880 MHz | 890 MHz | 900 MHz | 910 MHz | 920 MHz | 930 MHz |
|---|---|---|---|---|---|---|---|---|
| On Glass | 21 | 17 | 12 | 8 | 4 | 0* | 0* | 0* |
| On Acrylic | 23 | 19 | 14 | 10 | 6 | 2 | 0* | 0* |

0* indicates that a lower code was needed but not available; 0 is a valid code.

In contrast to prior art systems in which the antenna impedance must be estimated indirectly, e.g., using the relative strength of the analog signal returned by a prior art tag 1500 in response to interrogation by the reader 1504, methods of the present disclosure employ the on-chip re-tuning capability of our tag 1500 to return a digital value which more directly indicates the effective antenna impedance. Using a reference table having a sufficiently fine resolution, it is possible to detect even modest changes in the relevant environmental conditions. It will be readily realized by practitioners in this art that, in general applications, environment conditions typically do not change in an ideal manner, and, more typically, changes in one condition are typically accompanied by changes in at least one other condition. Thus, antenna design will be important depending on the application of interest.

One possible approach mounts the antenna on a substrate that tends to amplify the environmental condition of interest, e.g., temperature.

Figure 17A:
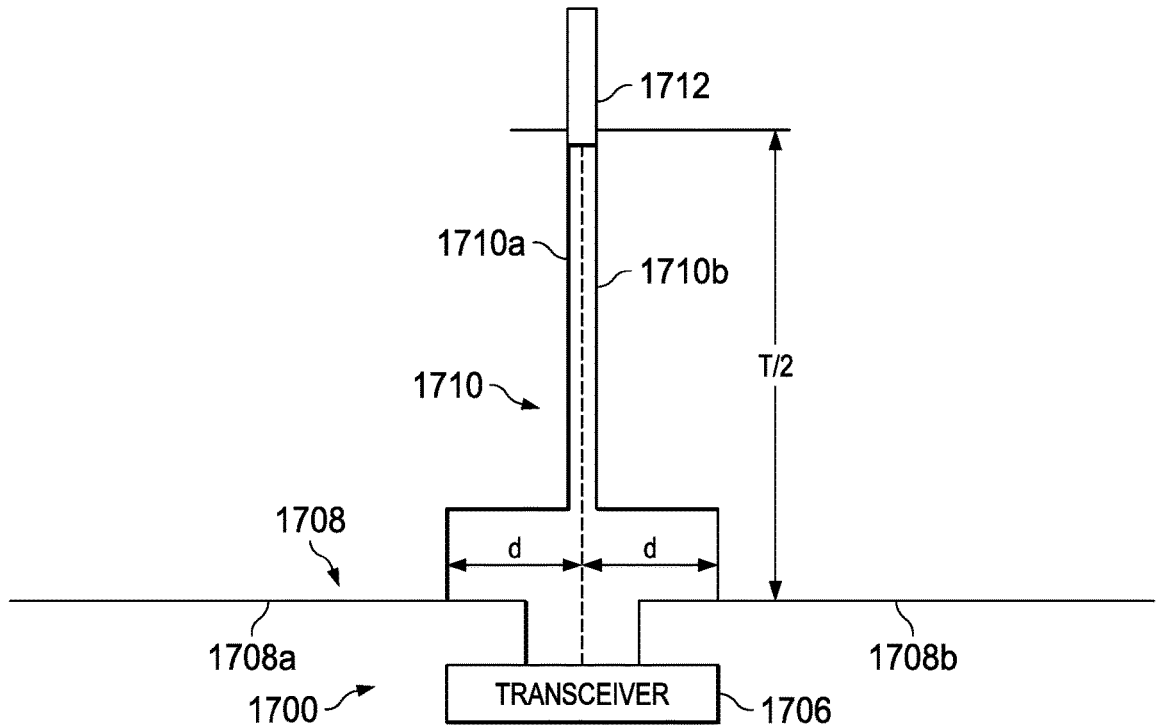
FIGS. 17A and 17B, illustrates an RF system constructed in accordance with one embodiment of the present disclosure to sense environmental conditions in a selected region surrounding the system.
Figure 17B:
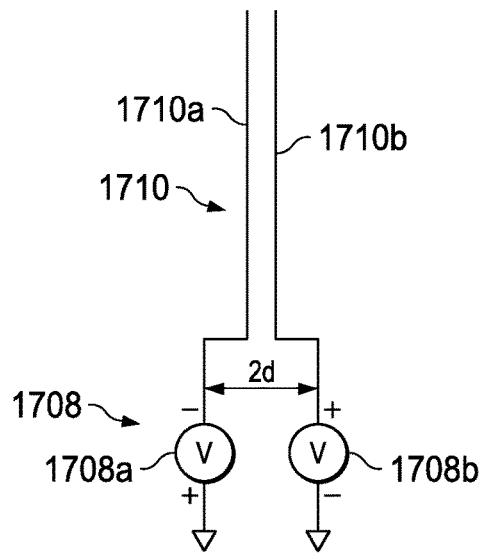

Shown in FIGS. 17A and 17B is an RF sensing system 1700 constructed in accordance with one embodiment of embodiments of the present disclosure, and specially adapted to facilitate sensing of one or more environmental conditions in a selected region surrounding the system 1700. In general, the system 1700 comprises: an RF transceiver 1706; a di-pole antenna 1708 comprising a pole 1708A and an anti-pole 1708B; and a tail 1710 of effective length T, comprising respective transmission line pole 1710A and transmission line anti-pole 1710B, each of length T/2. Tail 1710 includes a sensing portion having the transmission lines and a transporting portion 1712. Transporting portion 1712 may transport a disturbance from a remote location towards the sensing portion. In one embodiment transport portion 1712 wicks fluids/moisture/wetness from a remote location to be monitored to the sensing portion where the proximity of the sensing portion to the wicked fluids/moisture/wetness alters the load impedance of the transmission lines. The transporting portion 1712 and sensing portion may entirely overlap in certain embodiments or partially overlap in others. In accordance with embodiments of the present disclosure, the differential transmission line elements 1710A-1710B are symmetrically coupled to respective poles 1708A-1708B at a distance d from the axis of symmetry of the antenna 1708 (illustrated as a dotted line extending generally vertically from the transceiver 1706). In general, d determines the strength of the interaction between the transmission line 1710 and the antenna 1708, e.g., increasing d tends to strengthen the interaction. In the equivalent circuit shown in FIG. 17B, the voltage differential between the complementary voltage sources 1708A and 1708B tends to increase as d is increased, and to decrease as d is decreased. Preferably d is optimized for a given application. However, it will be recognized that the sensitivity of the antenna may be degraded as a function of d if a load, either resistive or capacitive, is imposed on the tail 1710.

In operation, the tail 1710 uses the transmission line poles 1710A-1710B to move the impedance at the tip of the tail 1710 to the antenna 1708, thus directly affecting the impedance of the antenna 1708. Preferably, the transceiver 1706 incorporates our tuning circuit 606 so as to detect any resulting change in antenna impedance and to quantize that change for recovery, e.g., using the method we have described above with reference to FIG. 16.

Figure 18:
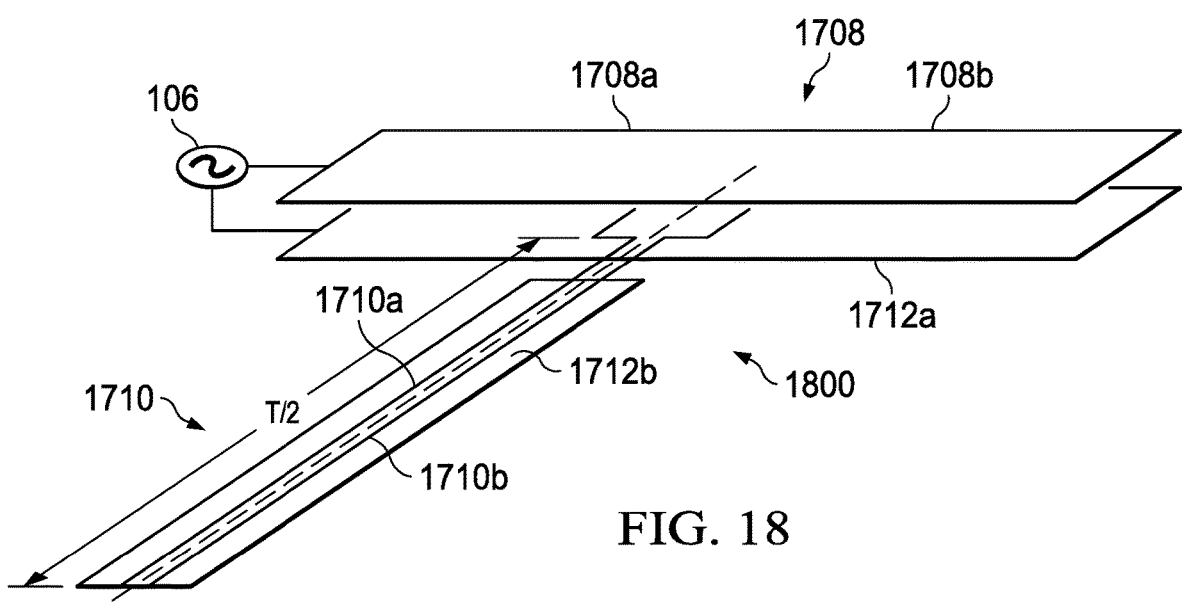
FIG. 18 illustrates, in perspective, exploded view, one possible configuration of an antenna and tail arrangement adapted for use in the system of FIG. 17.

FIG. 18 illustrates one possible embodiment of the system 1800 in which the antenna poles 1708A-1708B are instantiated as a patch antenna (illustrated in light grey), with the antenna pole 1708A connected to one output of transceiver 1706, and the other output of transceiver 1706 connected to the antenna anti-pole 1708B. A ground plane 1712A (illustrated in a darker shade of grey than the patch antenna 1708) is disposed substantially parallel to both the antenna poles 1708A-1708B and a ground plane 1712B disposed substantially parallel to the transmission line poles 1710A-1710B. As is known, the ground planes 1712 are separated from the poles by a dielectric substrate (not shown), e.g., conventional flex material or the like. If the dielectric layer between the antenna poles 1708 and ground plane 1712A is of a different thickness than the layer between the transmission line poles 1710 and the ground plane 1712B, the ground plane 1712B may be disconnected from the ground plane 1712A and allowed to float. In general, this embodiment operates on the same principles as described above with reference to FIGS. 17A and 17B.

Figure 19:
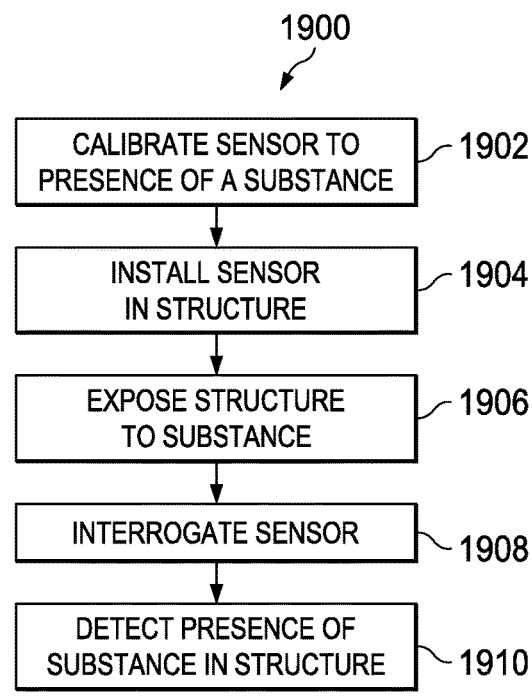
FIG. 19 illustrates, in flow diagram form, the sequencing of the operations in detecting the presence of a contaminant using, e.g., the antenna of in the system shown in FIG. 18.

Shown in FIG. 19 is one possible flow for a sensing system 1700 using the antenna 114. As has been explained above with reference to FIG. 16, operations 1900 begins with the sensor being first calibrated (step 1902 to detect the presence of varying levels of a particular substance. For the purposes of this discussion, we mean the term substance to mean any physical material, whether liquid, particulate or solid, that is: detectable by the sensor; and to which the sensor demonstrably responds. By detectable, we mean that, with respect to the resonant frequency of the antenna in the absence of the substance, the presence of the substance in at least some non-trivial amount results in a shift in the resonant frequency of the antenna, thereby resulting in a concomitant adjustment in the value stored in the shift register 1502; and by demonstrably responds we mean that the value stored in the shift register 1502 varies as a function of the level the substance relative to the tip of the tail 1710 of the antenna 1700. Once calibrated, the sensor can be installed in a structure (step 1904), wherein the structure can be open, closed or any condition in between. The structure can then be exposed to the substance (step 1906), wherein the means of exposure can be any form appropriate for both the structure and the substance, e.g., sprayed in aerosol, foam or dust form, immersed in whole or in part in a liquid, or other known forms. Following a period of time deemed appropriate for the form of exposure, the sensor is interrogated (step 1908) and the then-current value stored in the shift register 1502 retrieved. By correlating this value with the table of calibration data gathered in step 1902, the presence or absence of the substance can be detected (step 1910).

In one embodiment, the table of calibration data can be stored in the sensor and selectively provided to the reader during interrogation to retrieve the current value. Alternatively, the table can be stored in, e.g., the reader and selectively accessed once the current value has been retrieved. As will be clear, other embodiments are possible, including storing the table in a separate computing facility adapted to selectively perform the detection lookup when a new current value has been retrieved.

Figure 20:
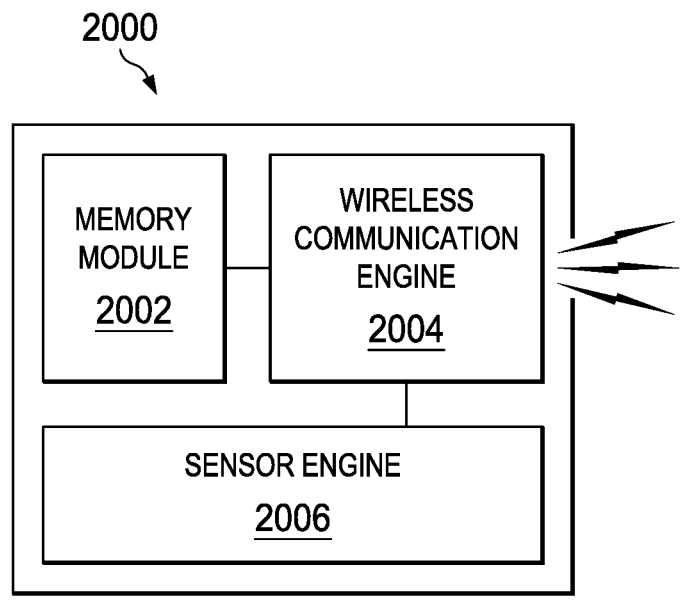
FIG. 20 is a block diagram of a RFID wireless solution provided by embodiments of the present disclosure.

FIG. 20 is a block diagram of a RFID wireless solution provided by embodiments of the present disclosure. Integrated circuit (IC) 2000 comprises a memory module 2002, a wireless communication engine 2004, and a sensor engine 2006 which includes an antenna 2008. IC 2000 is capable of sensing a change in the environmental perimeters proximate to IC 2000 via impedance changes associated with antenna 2008. In other embodiments, a proximity sensor may be employed to determine the proximity of IC 2000 to a given location or RFID reader by tuning the antenna 2008 and an associated tunable impedance. Memory module 2002 is coupled with both the wireless communication engine 2004 and sensor engine 2006. Memory module 2002 is capable of storing information and data gathered by sensor engine 2006 and communicated via wireless communication engine 2004. Further, wireless communication engine 2004 and sensor engine 2006 may be fully programmable via wireless methods. Passive RFID sensors of FIG. 20 may be deployed as an array of smart sensors or agents to collect data that may be sent back to a central processing unit.

Figure 21:
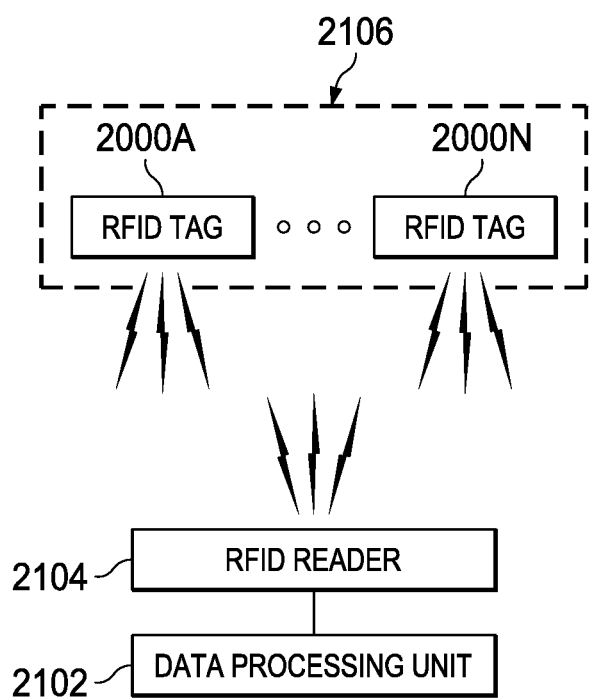
FIG. 21 is a block diagram of one arrangement of smart sensors and a data processing unit in accordance with embodiments of the present disclosure.

FIG. 21 is a block diagram of one arrangement of smart sensors and a data processing unit 2102 in accordance with embodiments of the present disclosure. Here a series of passive RFID sensors 2000A-N are deployed wherein each sensor may have a unique identification number stored within the memory module and communicated via the internal wireless communications engine 2004 to a data processing unit. Interrogator (RFID reader) 2104 interacts with passive RFID sensors 2000A-N. Interrogator 2104 may then communicate with a data processing unit 2102. Thus, the passive RFID sensor array 2106 may allow information to be sensed and communicated via RFID reader 2104, wherein this information may be pre-processed at the passive RFID sensor, or remotely processed at the RFID reader 2104 or data processing unit 2102 depending on the system needs.

Embodiments of the present disclosure realize an advantage over prior systems, in that not all sensing requires high precision sensors which are both expensive and consume relatively large amounts of power. The sensors provided by embodiments of the present disclosure are relative measurements and post processing of collected measurements yields sense information. Calibration may be done during manufacturing at the wafer or die level or when the assembled sensors are deployed in the field wherein this calibration information may be stored in the memory module 2002. This information may be retrieved at any time for baseline calculations. From relative changes, accurate information may then be derived from remote data processing provided by data processing unit 2102. Calibration may involve retrieving sensing measurements from memory module 2002 or current measurements directly form sensor engine 2006. The use of this information then allows accurate data associated with environmental conditions to be determined. In one example, RFID sensor array 2106 of FIG. 21 may include temperature sensors. Wherein each passive RFID sensor 2000A-N is an independent sensor and may sense a current condition at time zero that is stored to memory module 2002 or sent to data processing unit 2102. This measurement may be repeated at Time 1. Wherein this data is either stored or transmitted. Data processing unit 2102 may perform more complex calculations. For example, if the temperature is known at Time 0, the sensor information collected at Time 1, when communicated may be processed using information associated with the measurements and known temperature at Time 0 in order to determine or approximate an actual temperature. This may involve a lookup in a characterized data table or computations based on mathematical models of the calibration of the sensors to determine or approximate the actual temperature.

Another embodiment can sense the level of wetness or humidity proximate to the sensor engine. In either case, temperature or moisture, raw data may be collected from passive RFID sensors via the RFID reader for processing to be performed by data processing unit 2102 where the computation to determine a humidity or temperature measurement.

Figure 22:
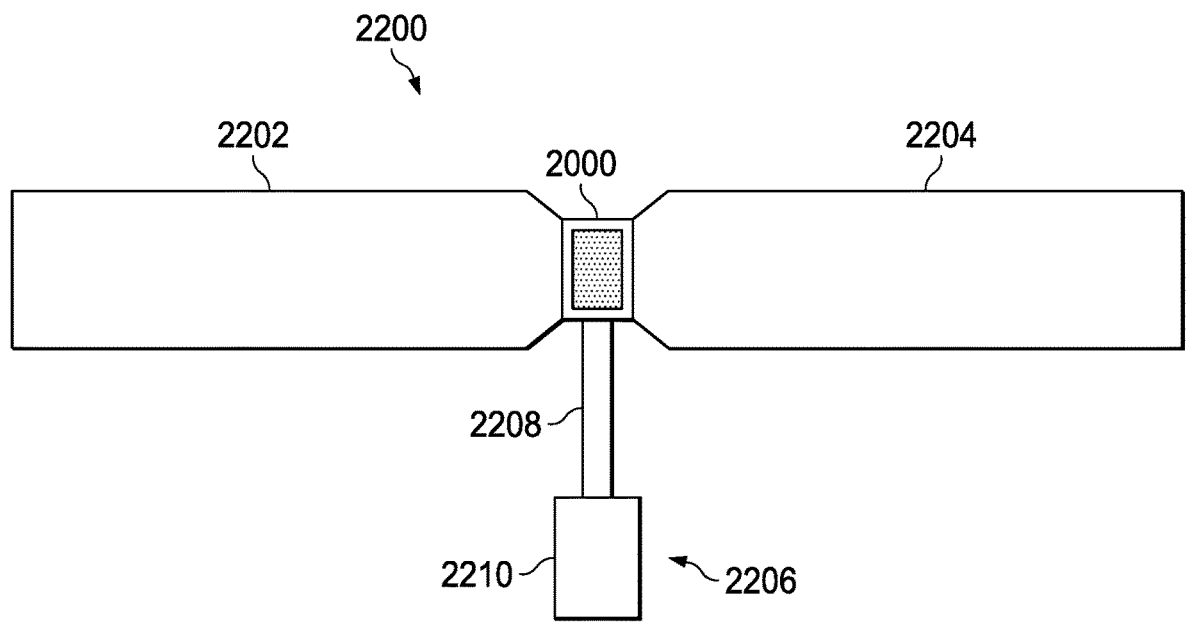
FIG. 22 provides an illustration of an antenna arrangement in accordance with embodiments of the present disclosure.

FIG. 22 provides an illustration of an antenna arrangement in accordance with embodiments of the present disclosure. In this antenna arrangement 2200 the antenna comprises a first antenna wing 2202, a second antenna wing 2204, and a tail 2206 coupled to IC 2000.

Tail 2206 includes a sensing portion 2208 having the transmission lines and a transporting portion 2210. Transporting portion 2210 may transport a disturbance from a remote location towards the sensing portion. In one embodiment transport portion 2210 wicks fluids/moisture/wetness from a remote location to be monitored to the sensing portion where the proximity of the sensing portion to the wicked fluids/moisture/wetness alters the load impedance of the transmission lines. The transporting portion 2210 and sensing portion 2208 may entirely overlap in certain embodiments or partially overlap in others.

IC 2000 may optimize the impedance match between the IC 2000 and antenna 2200 and tail 2206. This can be accomplished by adding shunt capacitors, variable inductors or variable impedances across the input terminals of IC 2000. As a result, the input impedance of the integrated circuit can be varied, in one embodiment, between 2.4 minus J 67.6 to 0.92 minus J 41.5 ohms. An antenna such as that provided in FIG. 22 may be designed to operate within these impedance values.

In one embodiment, this may provide an RF sensitivity of approximately −10.5 DbM. The antenna provided in FIG. 22 may be optimized to provide a conjugate match in one embodiment at about 960 megahertz. This allows the integrated circuit to optimize and match by selecting the best self tuning value over the remaining portion of the frequency band. The operational bandwidth is proportional to the RFID tag thickness.

The antennas provided by embodiments of the present disclosure may be fabricated in one embodiment using flex PCB materials. Electrical connections between the bumps of the integrated circuit and the antenna allow the antenna and integrated circuit to be electrically coupled.

Figure 23:
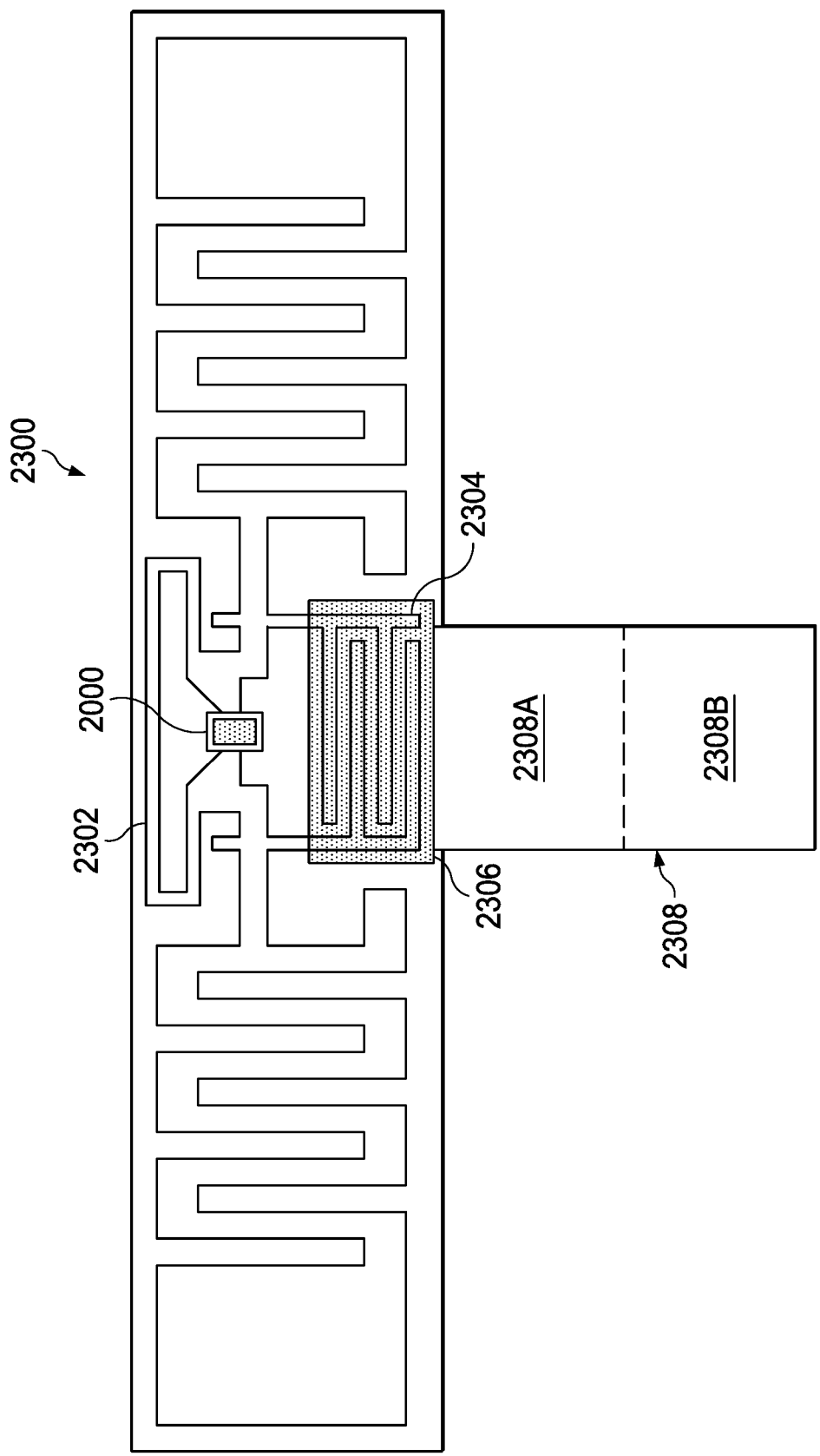
FIG. 23 is a view of an RFID moisture or humidity sensing tag in accordance with an embodiment of the present disclosure.

FIG. 23 is a view of an RFID moisture or humidity sensing tag 2300 in accordance with an embodiment of the present disclosure. Moisture or humidity sensing 2300 is a passive RFID tag, which includes a sensor, the sensor having a variable sensor impedance, and IC 2000. The sensor impedance varies as the coupling of interdigitated capacitor 2304 responds to environmental changes. These changes may be wicked to the interdigitated capacitor 2304 by tail 2308 which may be entirely composed of a material that transports fluids/moisture/wetness to the interdigitated capacitor 2304 by capillary action. More generally tail 2308 transports environmental disturbances to the interdigitated capacitor 2304. In one embodiment, interdigitated capacitor 2304 is located proximate to a film 2306 applied above interdigitated capacitor 2304. Film 2306 may be a material having an affinity for water (i.e. moisture or humidity) or other fluids. These fluids may include CO, CO2, Arsenic, H2S or other known toxins or gases of interest. When film 2306 absorbs a fluid such as those described previously, the dielectric constant proximate to the interdigitated capacitor 2304 changes causing an impedance change. The impedance of the interdigitated capacitor 2304 sensed by the processing module coupled to the sensor then produces an output, a sensor code, representative of the absorbed material within film 2306. This data may be stored within a memory circuit of IC 2000 or transmitted to an external reader by the wireless communication module of IC 2000.

Figure 24:
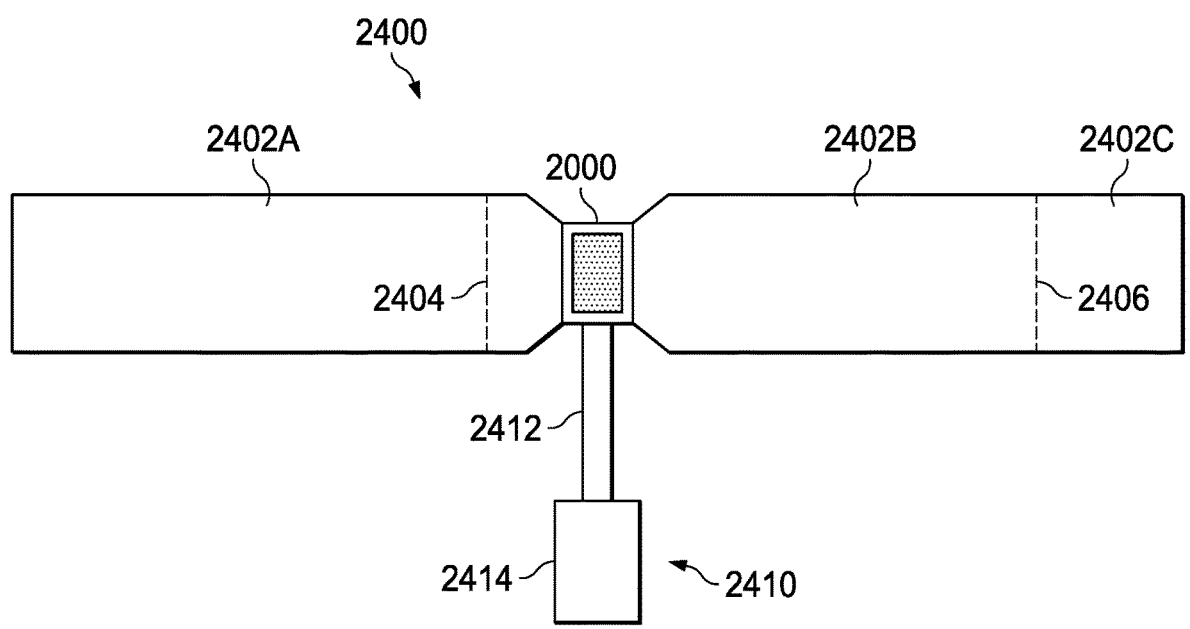
FIG. 24 is a view of a folded RFID tag comprising a radiating element in accordance with an embodiment of the present disclosure.

FIG. 24 is a view of a folded RFID tag 2400, including antenna 2402 comprising a radiating element, the radiating element comprising a first wing 2402A and a second wing, the second wing divided into a proximal section 2402B and a distal section 2402C, the distal section 2402C folded onto the proximal section 2402B, and the first wing 2402A folded onto the folded second wing, the distal section 2402C of the second wing capacitively couples to the proximal section 2402B and the first wing 2402A. Tail 2410 includes a sensing portion 2414 having the transmission lines and a transporting portion 2412. Transporting portion 2412 may transport a disturbance from a remote location towards the sensing portion. In one embodiment transport portion 2412 wicks fluids/moisture/wetness from a remote location to be monitored to the sensing portion where the proximity of the sensing portion to the wicked fluids/moisture/wetness alters the load impedance of the transmission lines. The transporting portion 2412 and sensing portion 2410 may entirely overlap in certain embodiments or partially overlap in others. These sections are folded about a PCB core.

Figure 25A:
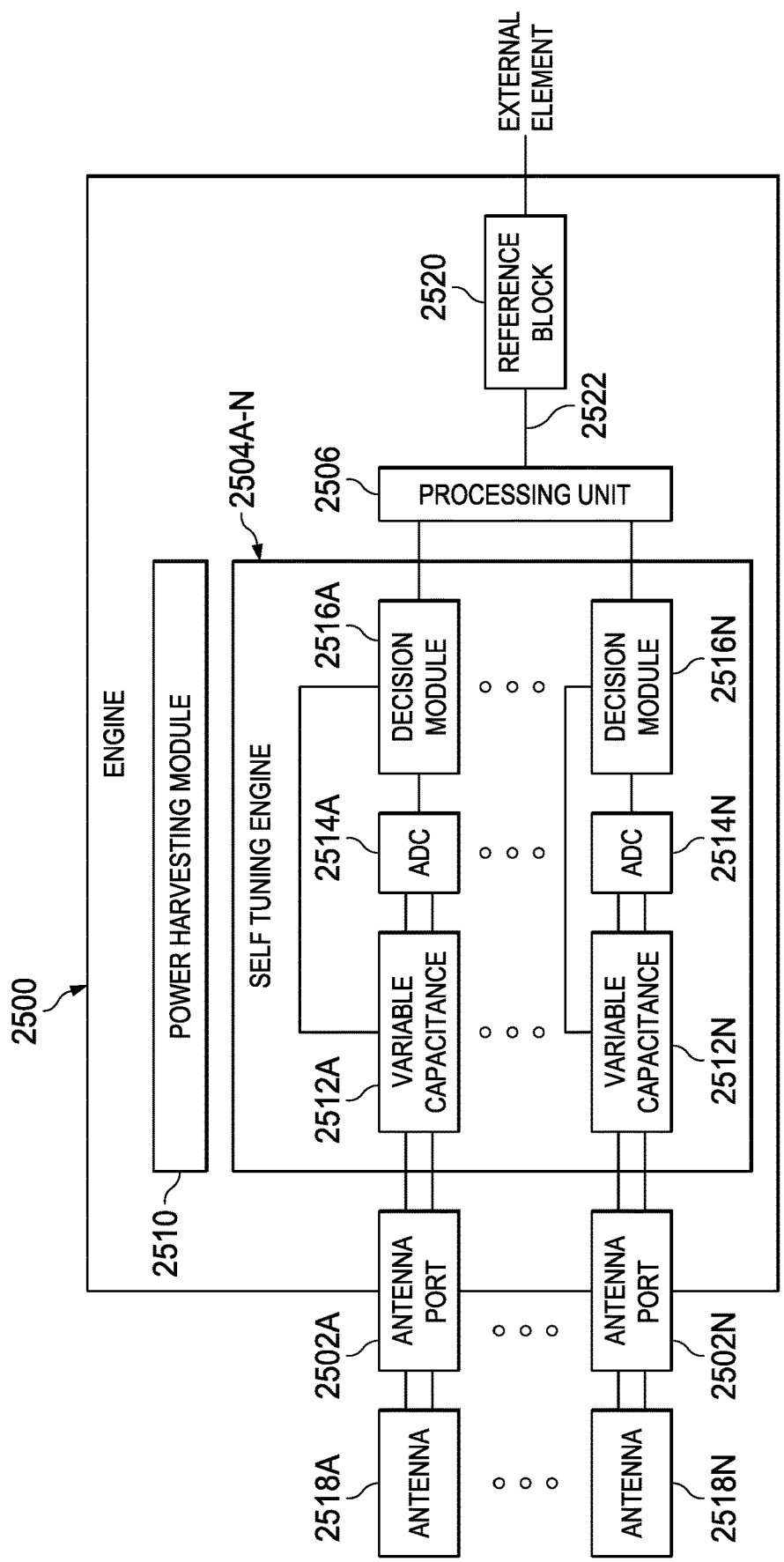
FIGS. 25A-C are block diagrams of arrangements of self-tuning engines to support the reporting of several stimuli with multiple passive RFID sensors using antenna impedance sensing mechanisms in accordance with embodiments of the present disclosure.
Figure 25B:
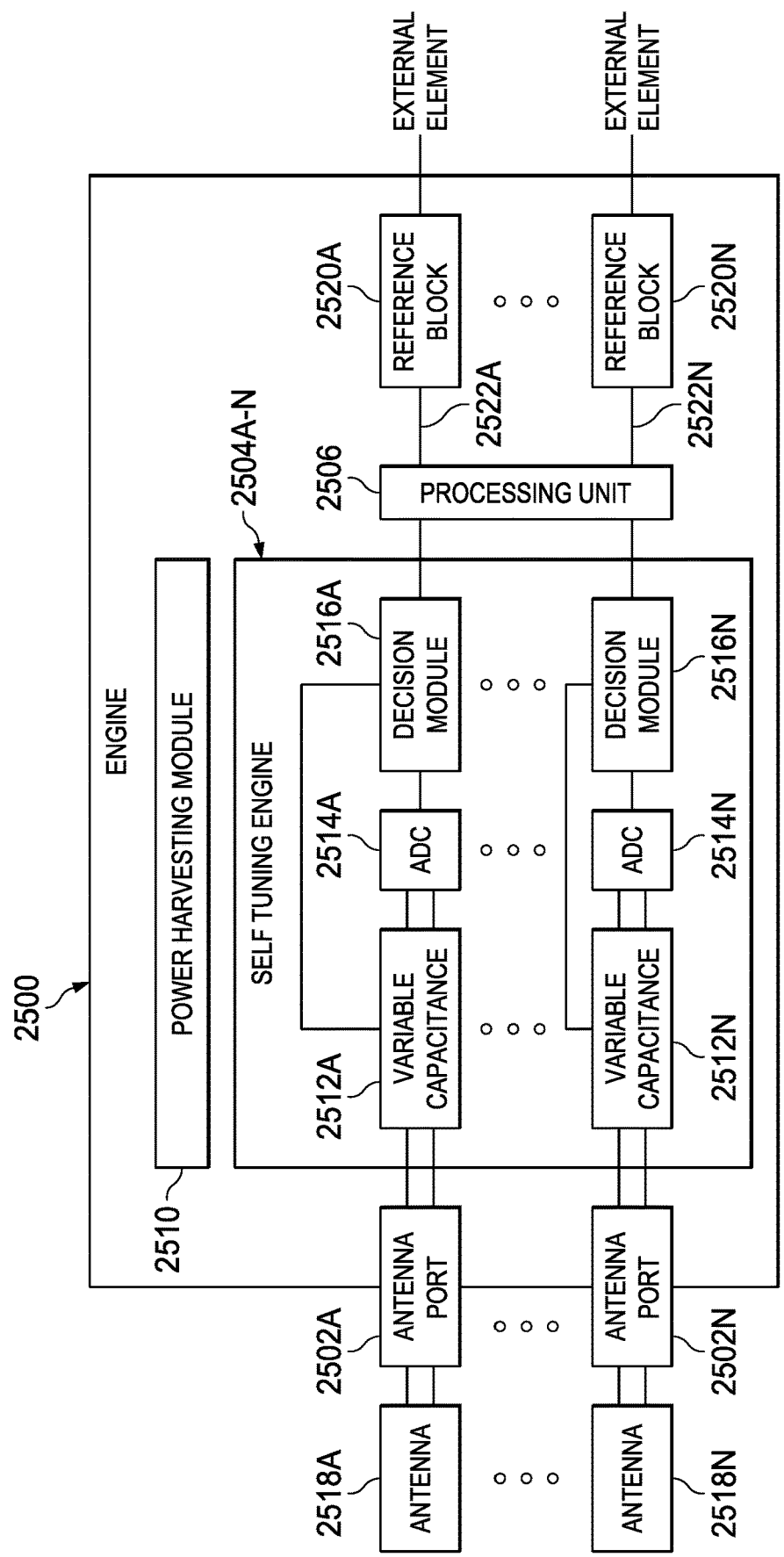
Figure 25C:
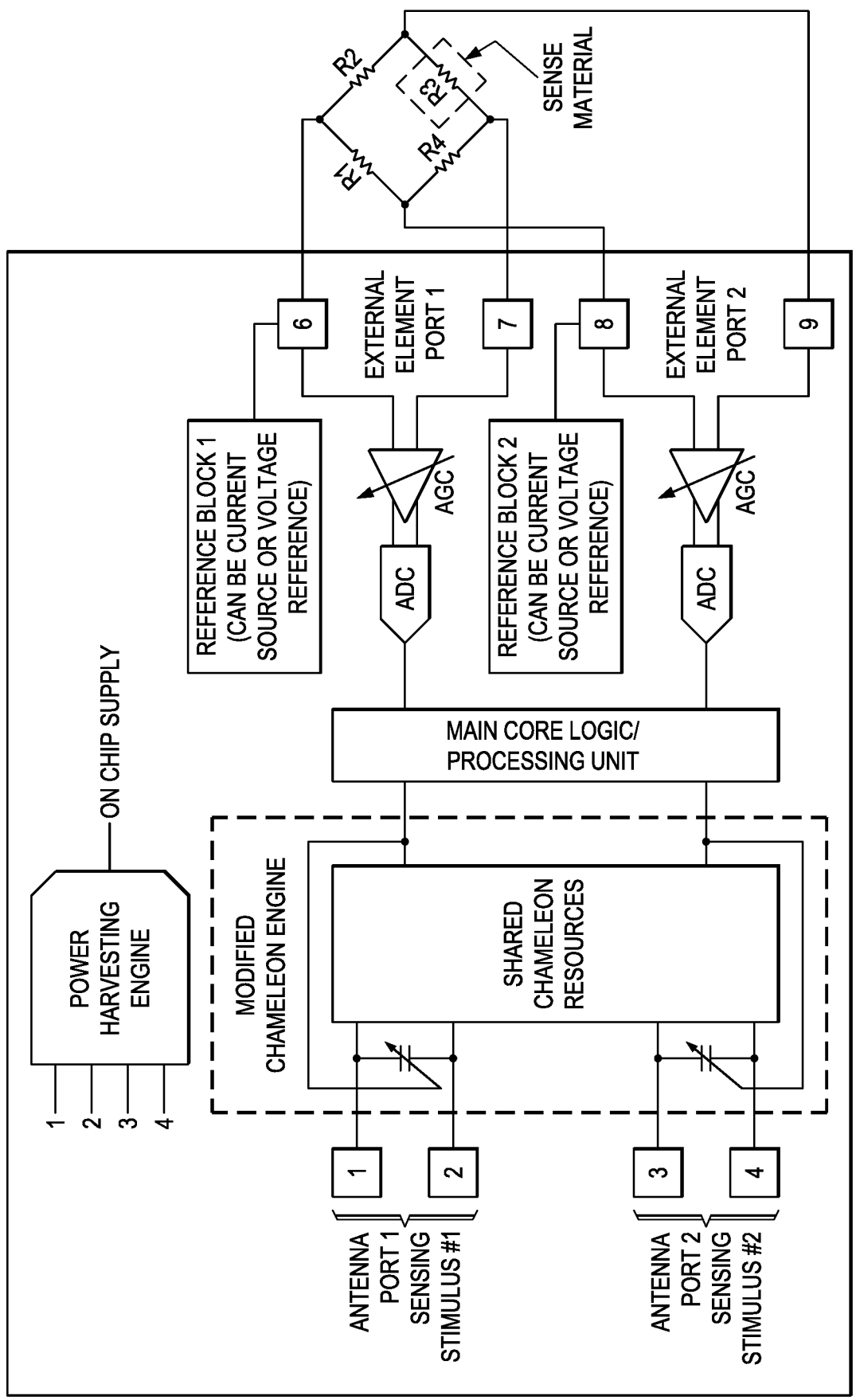

FIGS. 25A-C are block diagrams of arrangements of a self-tuning engine to support the reporting of several stimuli with multiple passive RFID sensors using an antenna impedance sensing mechanism in accordance with embodiments of the present disclosure. Module 2500 includes antenna ports 2502A-N, self-tuning engines 2504A-N, processing unit 2506, reference input module 2508 and power harvesting module 2510. A number of antenna ports 2502A-N passively sense stimuli through changing antenna inductance as previously discussed. The self-tuning engines 2504A-N adjusts a variable capacitance 2512A-N in response to the inductance sensed as ADC 2514A-N wherein decision module 2516A-N directs feedback to adjust the value of variable capacitance 2512A-N and produce a code reported to processing unit 2506. This sensor code reflects the sensed stimuli relative to the antenna inductor 2518A-N. The stimuli sensed may be any combination of stimuli sensed by the changing inductance of the antenna (i.e. pressure, moisture, proximity etc.) Processing unit 2506 is coupled to the self-tuning engines 2504A-N and other potential reference inputs such as those provided by reference block 2520. Reference block 2520 allows the processing unit to compensate for external elements sensitive to external stimulus with an input to processing unit 2506. One such example may be where an external element is sensitive to a condition such as temperature, in this example reference block 2520 provides a reference signal 2522 for the processing unit 2506. The block as a whole may be powered by a power harvesting engine 2510 to supply on-chip power needs.

Embodiments of the present disclosure encompass the ability for the passive RFID tag to (or based on the data supplied by the RFID tag) to make decisions based on multiple sensory inputs. Implemented in an on-chip signal processing circuit, single self tuning engine 2504A-N automatically adjusts the input impedance to optimally tune the RFID tag every time it is accessed.

RFID tags based on conventional chips can be detuned by a variety of external factors, most commonly by proximity to liquids or metals. Such factors can change the impedance characteristics of a tag's antenna. When the RFID tag chip has a fixed impedance, a mismatch between the chip and the antenna results, reducing the RFID tag's performance. Self tuning engine 2504A-N maintains the chip-antenna match as conditions change, resulting in more consistent RFID tag performance.

Reference signal 2522 is basically a reference voltage that is generated by an external sensing mechanism. In combination with one or more of the single self tuning engine 2504A-N, various decisions (e.g. co-dependent decisions) and sensing can be made based on various parameters collected from these multiple ports. A device can be interfaced to provide reference signal 2522. Examples of such devices include an accurate resistor (e.g. 1% resistor) between used to calibrate the various circuitry or sensors. The 1% resistor value can be digitized to calibrate temperature or pressure measurement. Other examples include: A photodiode to sense light; A pin diode; A remote temperature sensor; An LED (Light Emitting Diode); An infrared (I/R) sensor; and Basic I/O, ADC, DAC to input/output data from/to the sensor chip It may be desired to eliminate process variations or temperature variations from a sensing measurement (e.g. gas sensing application).

FIG. 25B illustrates yet another embodiment with two external sensing ports providing reference signals 2522A and 2522N. As discussed in various parts of this disclosure, the sense material can cause a change in resistance due to an environmental variable that is to be sensed and thus would affect the variation sensing leg differently than its effect on the rest of the resistors. All other environmental variables would affect the four balanced resistors equally and as such would be calibrated out and would not be sensed isolating the effect to the environmental variable affecting the variation sensing leg via the applied sense material.

One of the differences of sensing using an antenna port vs. an external element port is the fact that the sensing via the antenna port uses AC power generated by the application of a CW (continuous wave). The sensing on an external element port uses DC power that is generated via the power harvesting engine (using one or more charge pumps) as explained below. Given the fact that a charge pump efficiency of about 20% results in approximately five times increase in power consumption by sensing using the external element port vs. the antenna port (sensing using high frequency rather than DC).

Power harvesting engine 2510 generates DC power using one or more charge pumps. The charge pump is included in for example regulator 608 of FIG. 6, regulator 702 of FIG. 7, regulator 608 of FIG. 8, regulator 316 of FIG. 3 and regulator 316 of FIG. 5. Given the fact that a charge pump efficiency can greatly vary. The efficiency of a charge pump equals power delivered to its output (i.e. to the rest of the circuit it is to provide a supply voltage and current) divided by power consumed at its input. A charge pump, as known in the art, is continuously switching and whose voltage waveforms vary with time, so in general, efficiency can be measured as the ratio of the average power at input and output, as opposed to the ratio of instantaneous powers. A simple low efficiency charge pump can be designed to have a very quick startup time but will result in a great loss of power and thus be unable to operate a large amount of circuitry or sustain the operation of a circuit over a longer period of time compared to a higher efficiency charge pump. On the other hand, a higher efficiency charge pump in general will take a longer period of time to startup, but will be able to operate more circuitry given the same input power and would be able to sustain operation over a longer period of time that its low efficiency counterpart.

In order to achieve quick startup and efficient operation, a set of charge pumps may be used having different efficiencies. A first charge pump may be used to initially energize the RFID sensor. Once essential circuitry is operational, additional more efficient charge pumps may be used to energize the sensor and the remaining circuitry. This allows for a shorter time requirement to initialize the RFID sensor. Longer term operation of the RFID sensor may then be switched to the more efficient charge pump.

The charge pump(s) harvest power from the ports 2502A-N and then supplies DC power to the rest of the circuitry. Another embodiment includes the use of two or more charge pumps one corresponding to an individual port and then combining the currents from both in order to produce the DC supply voltage for the RFID Sensor. In yet another embodiment, two charge pumps can be used for a single self tuning engine 2504A-N regardless of whether the RFID tag a single or multiple single self tuning engine 2504A-N/Sensing antenna 2518 arrangements.

Two or more charge pumps may be coupled to an individual antenna. One charge pump to turn on the single self tuning engine 2504A-N quickly, and is thus optimized for low turn-on power which sacrifices efficiency. The second charge pump has a higher turn on power threshold but has a much higher efficiency. Both charge pumps may operate in parallel but results in a much faster turn-on time for the RFID tag.

Once sufficient stable power is available, power harvesting engine 2510 will produce a PowerOK signal to initiate system as seen in FIG. 4. A variable resistor can be provided in parallel with an inductor, so as to automatically vary this resistance to control the gain of the tank circuit within the power harvesting engine 2510.

The operation of the self-tuning engine in response to the PowerOK signal is illustrated in the description of FIG. 3, FIG. 4 and FIG. 5.

Another aspect of this disclosure is extending a mode that would allow for self-operation without the need for a reader but only a continuous wave (CW) source for power. In this self-operation mode, sensor values could be self-written in a user defined circular buffer in the memory (or other types of memories).

This mode would be entered with a header length in excess of specified period of time. For a typical transaction, the part would power up in the typical ready state to accept commands from a reader and respond like a traditional tag. Once a sufficient amount of time had passed and a command was not received, the part would enter into the self-operation mode of data logging. Some control and status registers could be preset by the user to configure this mode that could include:

d. data buffer size (1-x words in user bank)
    e. data buffer pointer/index
    f. Sensor to log (Self-tuning engine and/or Temp)
    g. Max/Min threshold value
    h. Max/Min Threshold exceeded count Every time the RFID sensor entered this logging mode the RFID sensor would measure/log the data, auto increment the pointer/index to the next word in the buffer and then hold in an idle state. If thresholds were employed, a count could simply be maintained for any measurements over/under the threshold. This is useful in applications like cold chain management of produce or pharmaceuticals where the customer only cares if a perishable product has fallen outside of a specified temperature window.

The primary benefit of this self-operation mode would be the low cost CW sources that could be utilized instead of full reader to create a wireless logging system. The CW source would essentially just be tied to a timer that would control when and how long it was turned on. The timer on the CW source would set the data logging interval with one sample taken every time the CW source was turned on.

The CW sources would be used throughout the system to maintain data collection operation for the RFID tags and then readers would only be needed at the endpoints of the system to gather the data logged. For a cold chain application, the low cost CW sources could be placed in the refrigeration trucks or warehouses and then the customer would verify the product condition with a reader when it arrived at market. This is an economically viable idea since the infrastructure required to simply generate CW source would be much less than implementing a full functionality reader and communication capabilities.

Yet another aspect of this disclosure is the IC harvesting power from a CW source that is a different bandwidth than the UHF bandwidth for RFID readers in the United States (902-928 MHz). But rather using a 2nd Self-tuning engine engine/antenna/sensor port in that is tuned for other frequency bands such as an ISM band source.

Another aspect of this disclosure is the integration of an antenna, self tuning engine and processing circuitry as part of a silicon wafer or a large IC (e.g. Microprocessor die, FPGA die). Such integration would enable a variety of applications that are currently not possible without powering an IC (e.g. Micro-processor or FPGA). For example, the ability to embed a serial number on in a Magnus register and to use an RFID reader to inventory the ICs. Such devices are very expensive and valuable and the ability to inventory each IC individually would provide great economic benefit such as saving time, fraud control and inventory control.

Additionally, having the sensor functionality can alert manufacturers, vendors, distributors and customers pre-production, post-production, pre-shipping, post-shipping and in the field to any exposure to environmental variables that are critical to the economic value and operation of the IC. Such harmful exposure is moisture, for example. Any of the sensory applications mentioned earlier in this application is possible.

Additional sensory applications are the detection of exposure to fluids (which includes gases, such as Oxygen for example). The locations of embodiments of the present disclosure do not have to be part of the IC design process but rather as part of the scribe area.

Figure 26:
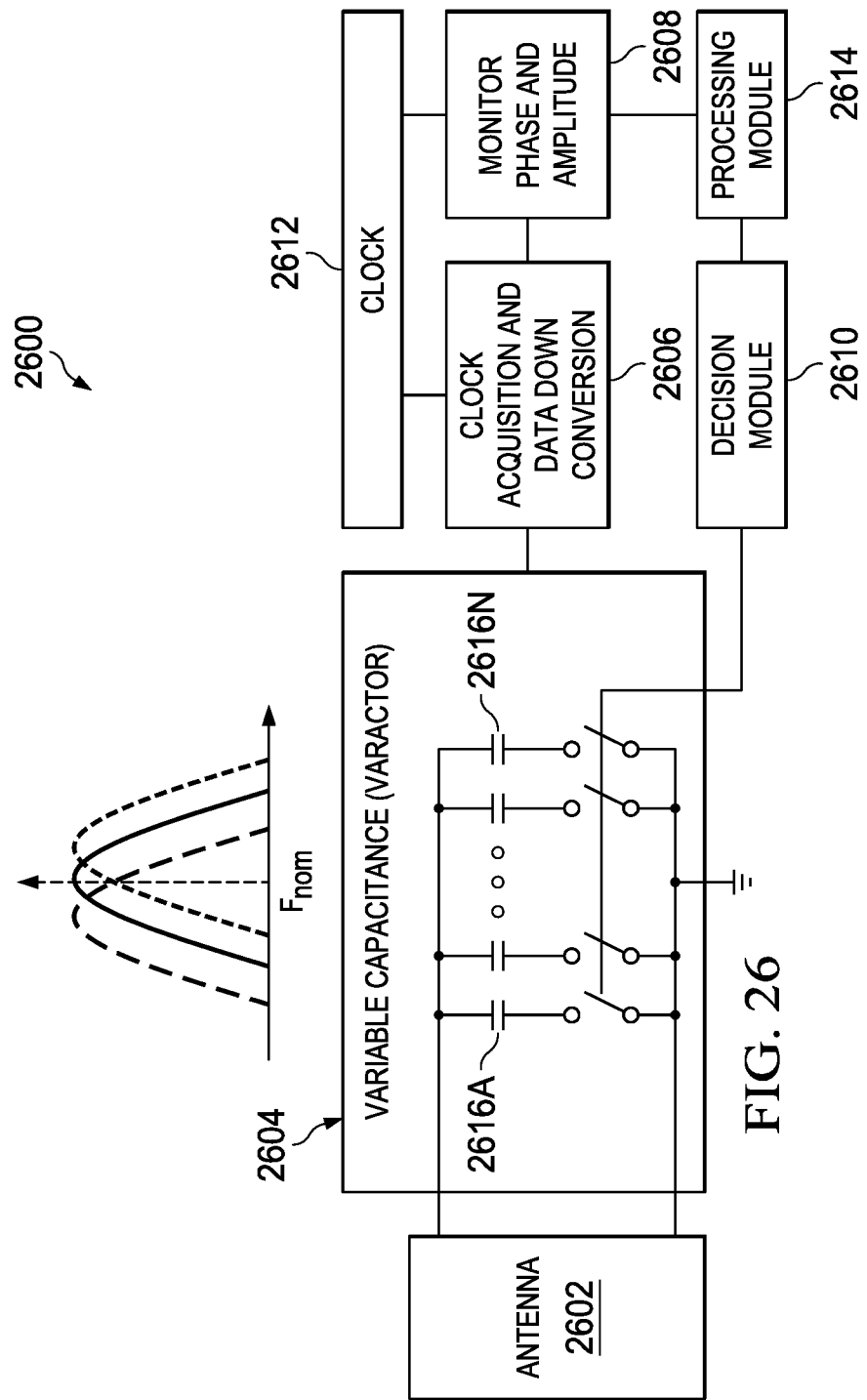
FIG. 26 is a block diagram of a self-tuning engine in accordance with embodiments of the present disclosure.

FIG. 26 is a block diagram of a self-tuning engine in accordance with embodiments of the present disclosure. Self-tuning engine 2600 includes an antennae 2602, a variable capacitance or varactor module 2604, a clock acquisition and data conversion module 2606, a monitoring module 2608, a decision module 2610, processing module 2614, and a clock module 2612.

Varactors are basically voltage-controlled capacitors. Varactors are implemented in various forms, for example as discrete components, in integrated circuits, in MEMS (micro-electro-mechanical systems). Varactors are widely used in RF circuits as tuning elements.

Figure 27:
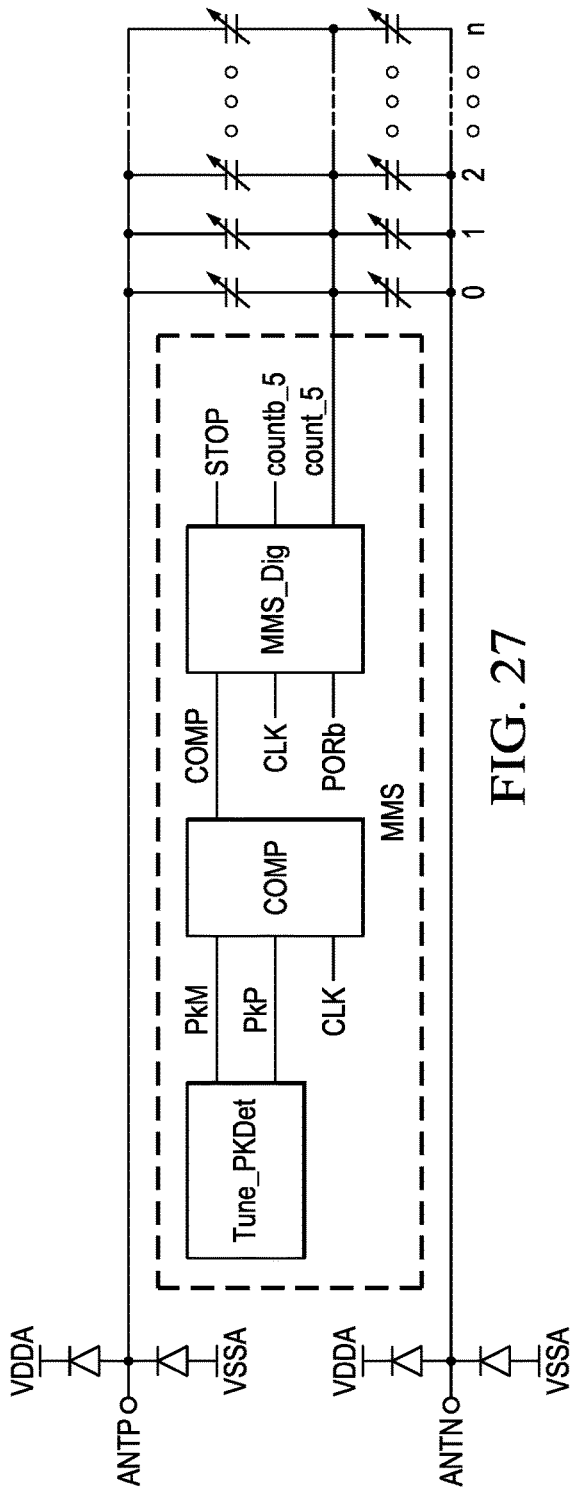
FIG. 27 illustrates an embodiment of the self-tuning engine provided by embodiments of the present disclosure along with the varactors that are driven by the self-tuning circuitry (also referred to as MMS engine in this disclosure)

FIG. 27 illustrates an embodiment of the self-tuning engine provided by embodiments of the present disclosure along with the varactors that are driven by the tuning circuitry (referred to as self tuning engine). The varactors in this embodiment are enhancement MOS varactors. In one embodiment, the engine generates 5 bits of sensor code (also referred to as MMS code) that are then converted to 16 bits (i.e. n=16) of thermometer codes. Each bit of the thermometer code drives one varactor unit. In this embodiment, there are a total of 16 varactor units (each unit is a varactor on its own). Each code can be either VDDA (a high voltage) or VSSA (a low voltage signal). The antenna ports; ANTP and ANTN, are set at a voltage value of VDDA/2.0 under normal operation. Looking at this from the varactor perspective, the Gate of each of the 16 varactor units will always be at VDDA/2.0V with respect to Bulk, while the S/D, (Source/Drain), connection of each of the 16 varactor units will be set to VDDA or 0V with respect to Bulk, depending on the sensor code generated. Hence, each of the 16 varactor units will be set to either its min capacitance or max capacitance value. The total capacitance of the varactor structure is the sum of these min/max values. This implementation is referred to here as a digital implementation of an embodiment of the self-tuning engine provided by embodiments of the present disclosure.

One embodiment of the present disclosure uses non-equal capacitors in the self-tuning engine with no simple ratio metric relationship (e.g. integer multiple or ratio of integers) to implement dithering.

Returning to FIG. 26, the clock acquisition and data conversion module 2606 will sense a voltage associated with the variable capacitance or varactor 2604 that may change as a function of antennae impedance wherein the impedance is changed based on environmental stimulus or other like conditions. Monitoring module 2608 may monitor phase and amplitude or other qualities associated with the data collected by clock and data conversion module 2606. This information is then provided to processing module 2614 which in conjunction with decision module 2610 may place capacitors 2616A through N in service within the variable capacitance or varactor 2604 in order to maximize power transfer or other like considerations with antennae 2602. The manipulation of the varactor 2604 will relate to a sensor code as discussed previously or other like signal. Clock 2612 provides a clock input to the various modules within Engine 2600 such that the data acquisition and the actions of the various processing modules may be coordinated.

Figure 28:
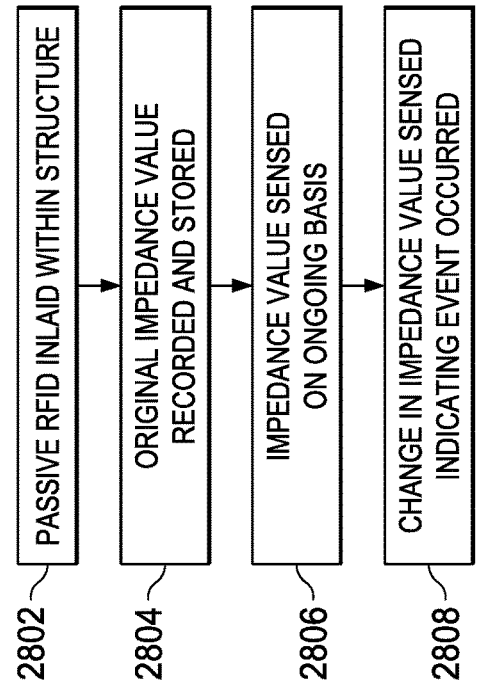
FIG. 28 provides a flow chart of one embodiment of the present disclosure.

Embodiments of the present disclosure may provide a passive RFID sensor (IC chip, antenna, and package) such that once an event of interest has occurred, the structure of the antenna and package may change its characteristics in an irreversible manner. FIG. 28 provides a flow chart of one such embodiment. In Block 2802, a passive RFID sensor, such as an antenna may be inlaid within the structure wherein a physical characteristic of the antenna and/or the sensor, such as impedance, may be altered when exposed to a sudden force. For example, an antenna may be wrapped around a glass or other structure. The original unique impedance value may be recorded and stored for comparison in block 2804. In block 2806, the impedance value may be read on an ongoing basis wherein when the impedance value or a code associated with the impedance value changes, that change signals that the event of interest may have occurred. Such an event may be when an object on which the passive sensor is mounted has been dropped.

In an embodiment, step 2806 of FIG. 28 can be altered so rather than sensing on an ongoing basis, the impedance is read at a later time that is offset from the event that caused the original unique impedance to change value. The sensing in step 2808 thus indicates that the particular event occurred that changed the original unique impedance because the new code read is different than the original code recorded in step 2804. The recording can be locally on the tag itself via a non-volatile memory or in a database remote from the tag as is associated with the unique identification number of the tag. In any of the cases, the magnitude of the impedance change, results in a different code change and thus is used to also detect the magnitude or amount of exposure to an event or and environmental change.

Figure 29A:
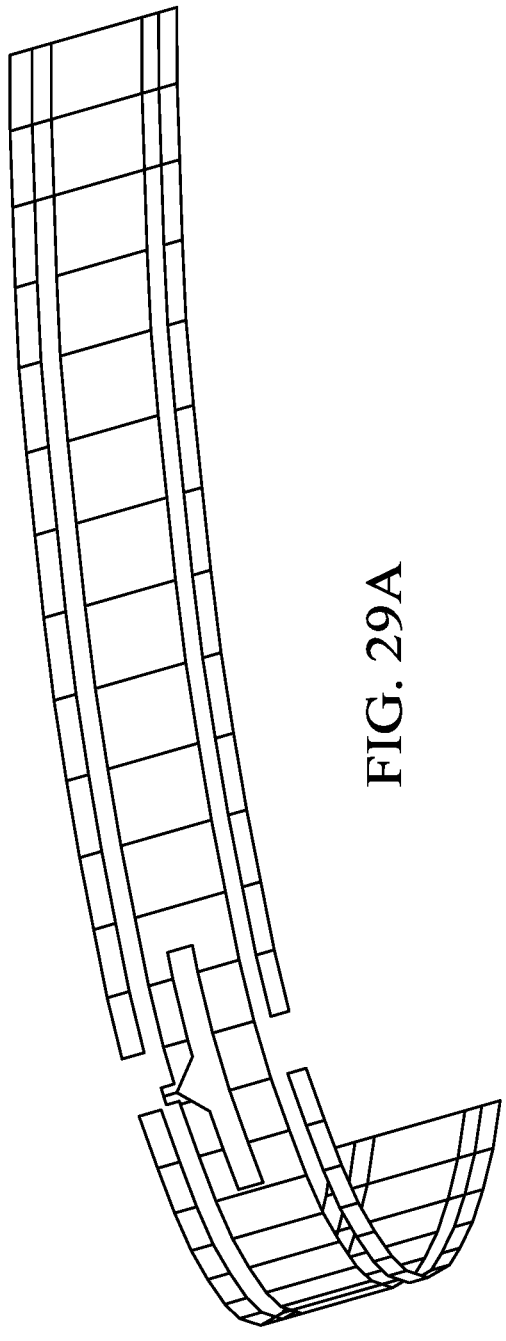
FIGS. 29A and 29B illustrate one passive RFID sensor in accordance with an embodiment of the present disclosure.
Figure 29B:
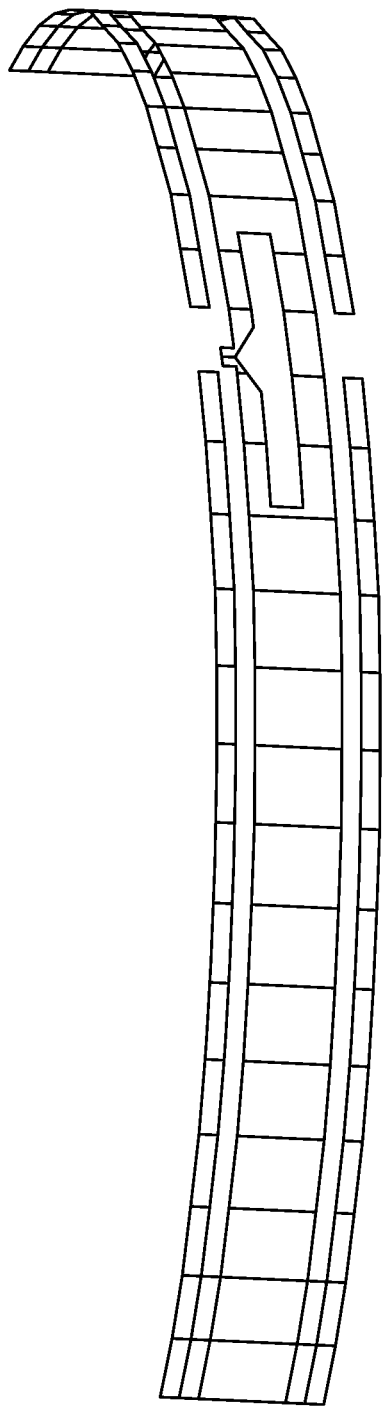

FIGS. 29A and 29B illustrate one passive RFID sensor in accordance with an embodiment of the present disclosure. FIGS. 29A and 29B provide an embodiment of an RFID tag with a particular antenna structure being a dual-mode dipole design designed to perform directly on the skin. The RFID moisture sensor may be optimized to achieve roughly equal performance whether the antenna is tight against the skin or spaced about 1 cm from the skin. This results in a balanced design to provide the same read range whether the band is tight or loose on the wrist. FIGS. 29A and 29B show a WristTag Antenna constructed with an antenna that is made of ½ oz copper (Cu) on 10 mil PET with no overlay. The IC 2000 may be flip-mounted directly to the Cu using anisotropic conductive adhesive (ACP).

FIGS. 30-38 are graphs of several measurements taken using two different samples (sample 1 and sample 2) while on a human wrist and on a 2.5 inch diameter water bottle in different configurations. The placement on the 2.5" bottle is used to simulate placement on a human wrist. The results presented show that the results are similar.

Figure 30:
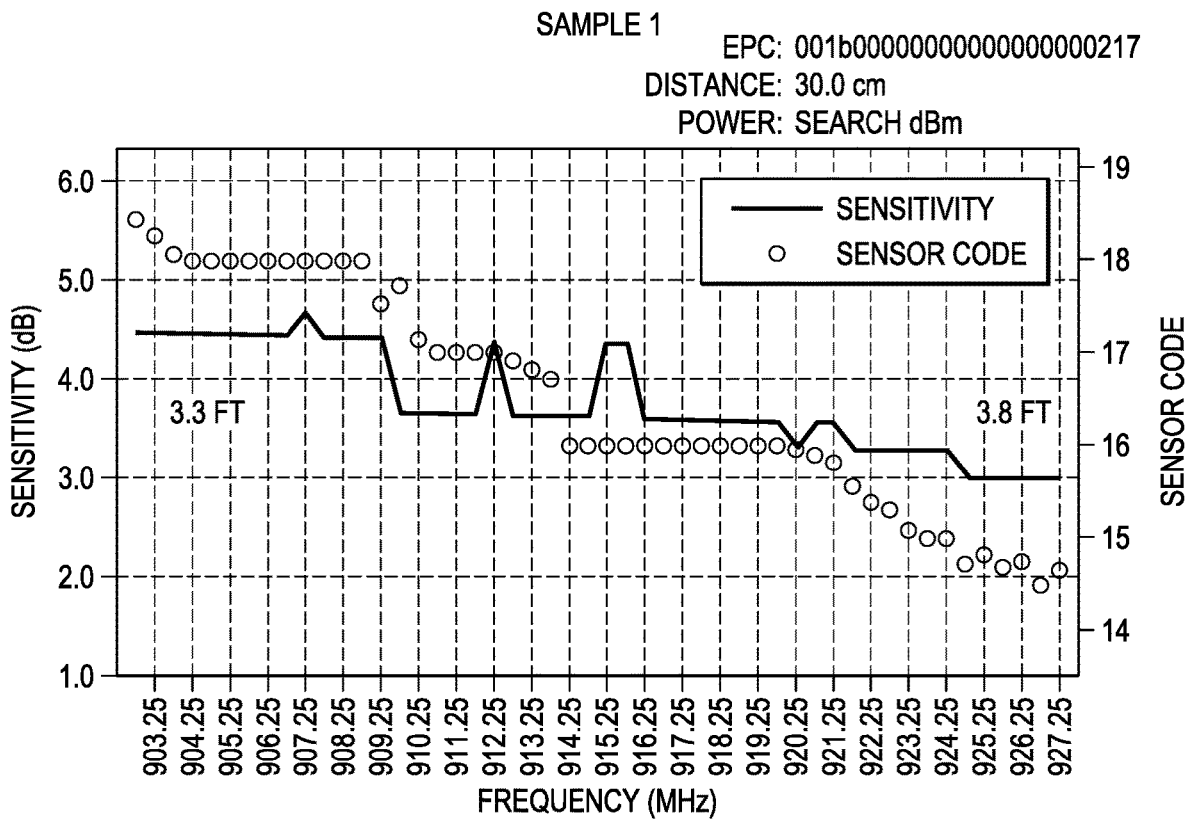
FIGS. 30-38 are graphs of several measurements taken using two different samples (sample 1 and sample 2) while on a human wrist and on a 2.5 inch diameter water bottle in different configurations in accordance with embodiments of the present disclosure.
Figure 30:
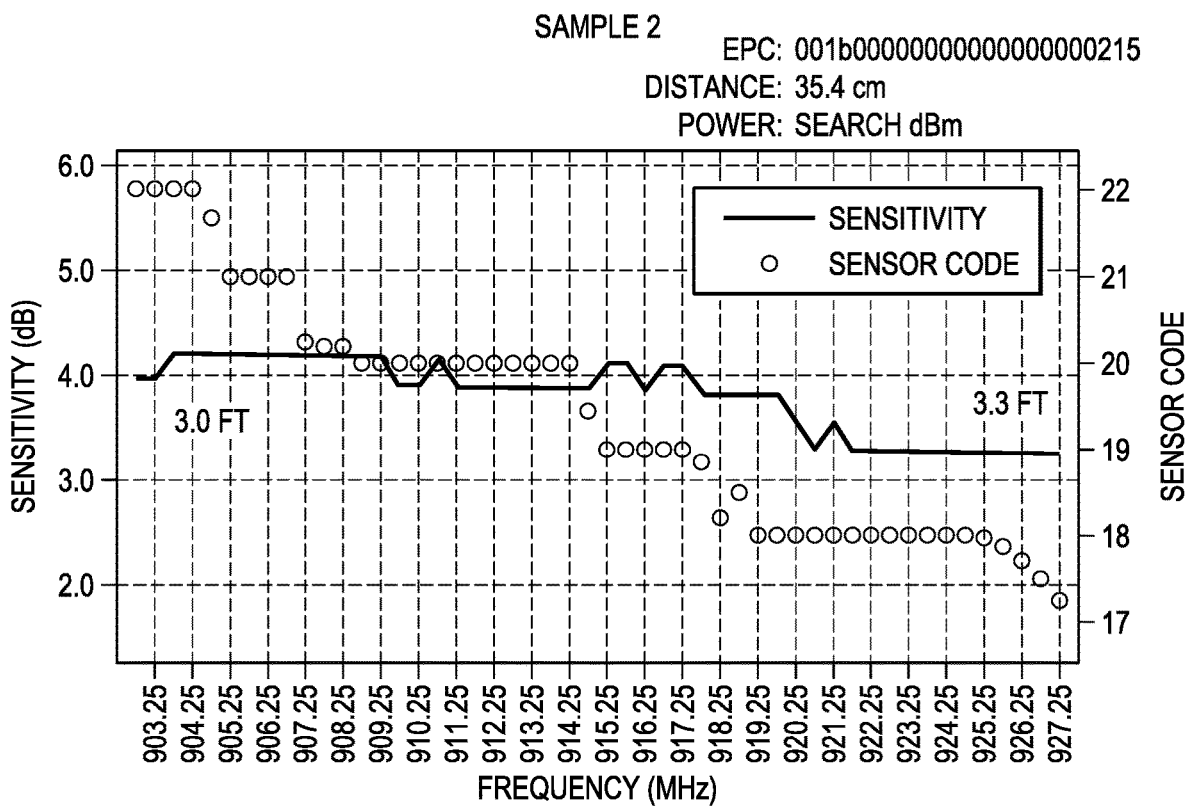
Figure 31:
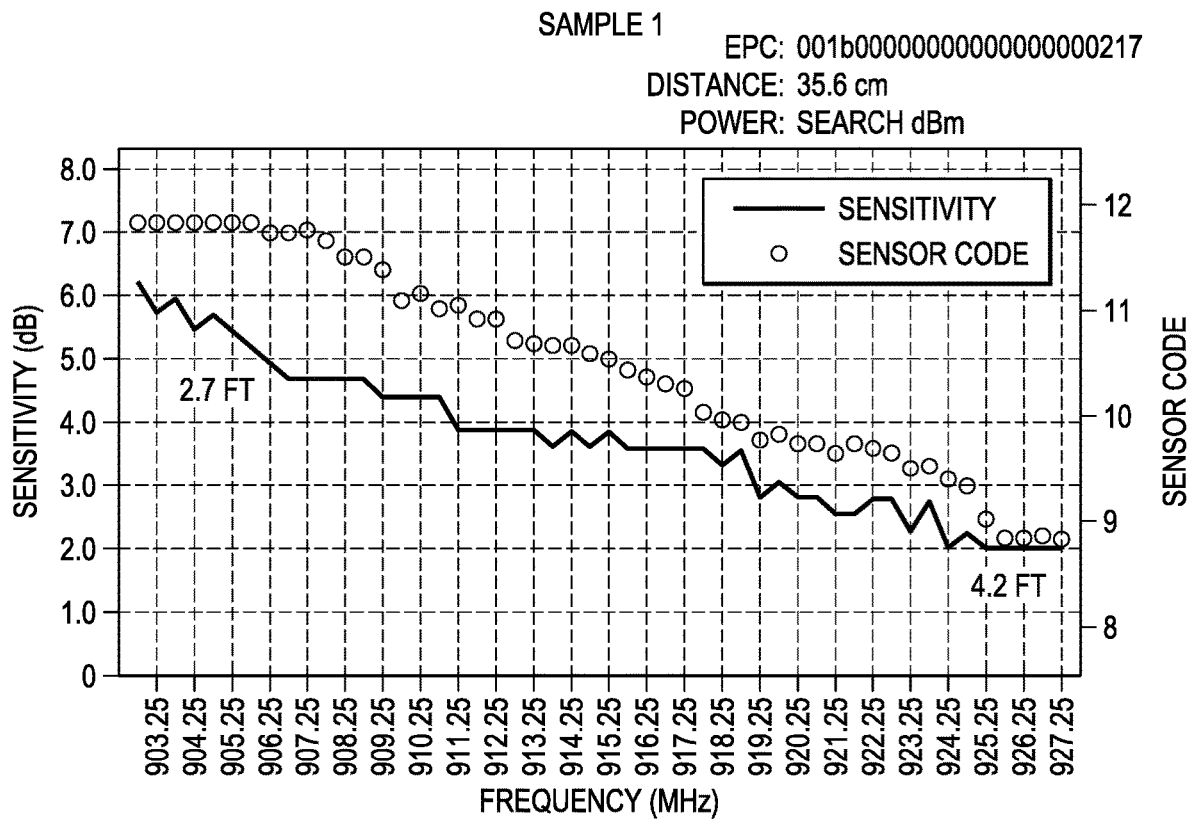
Figure 31:
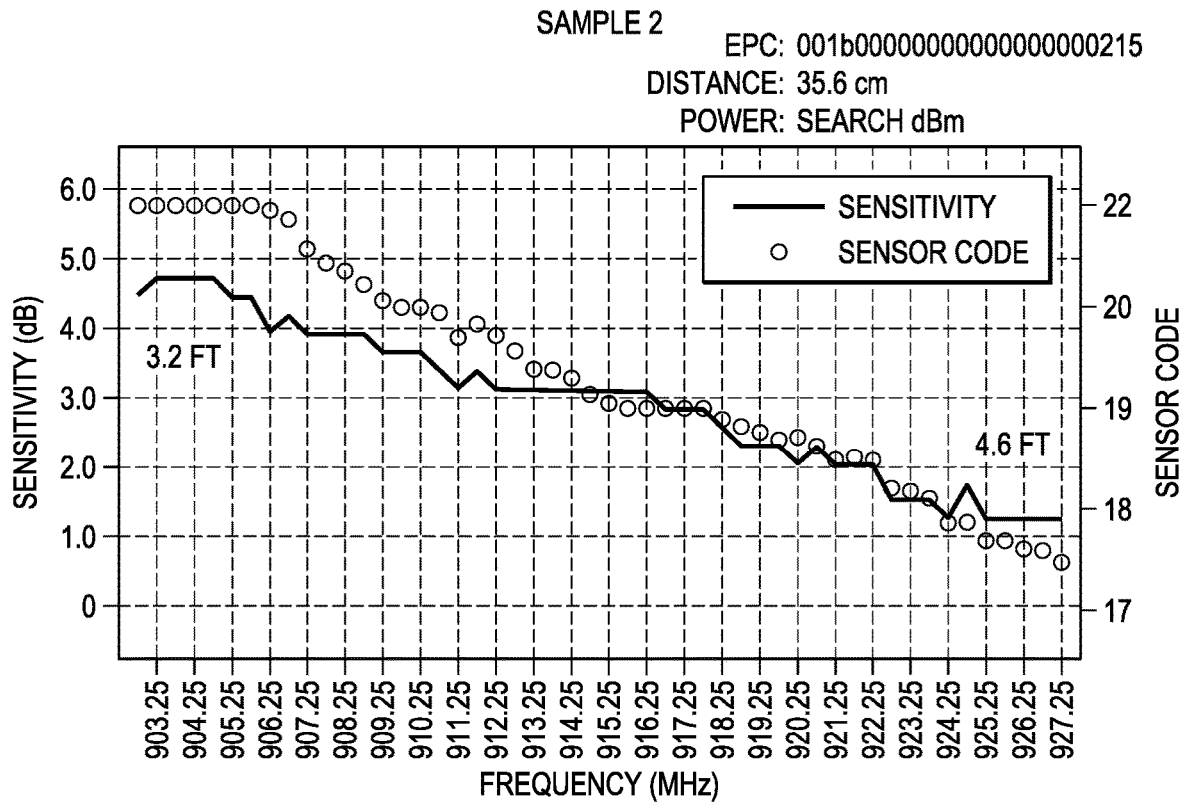
Figure 32:
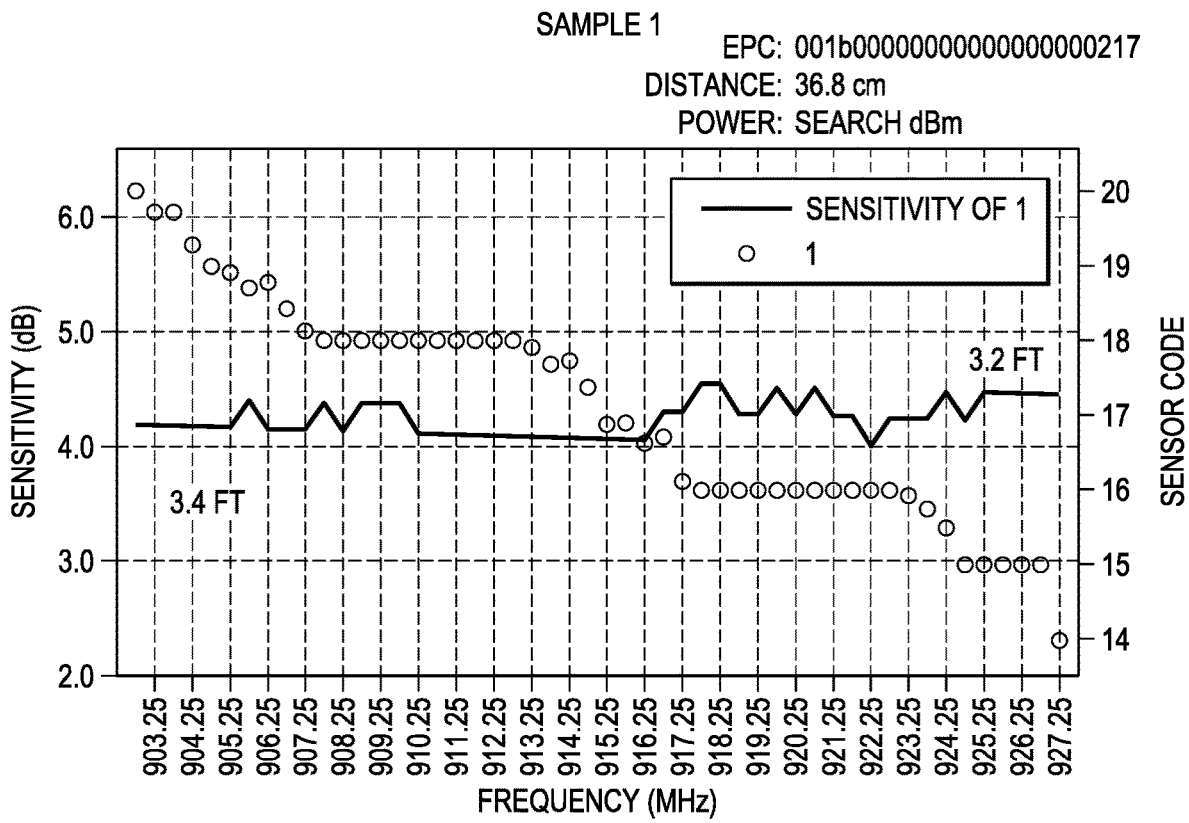
Figure 32:
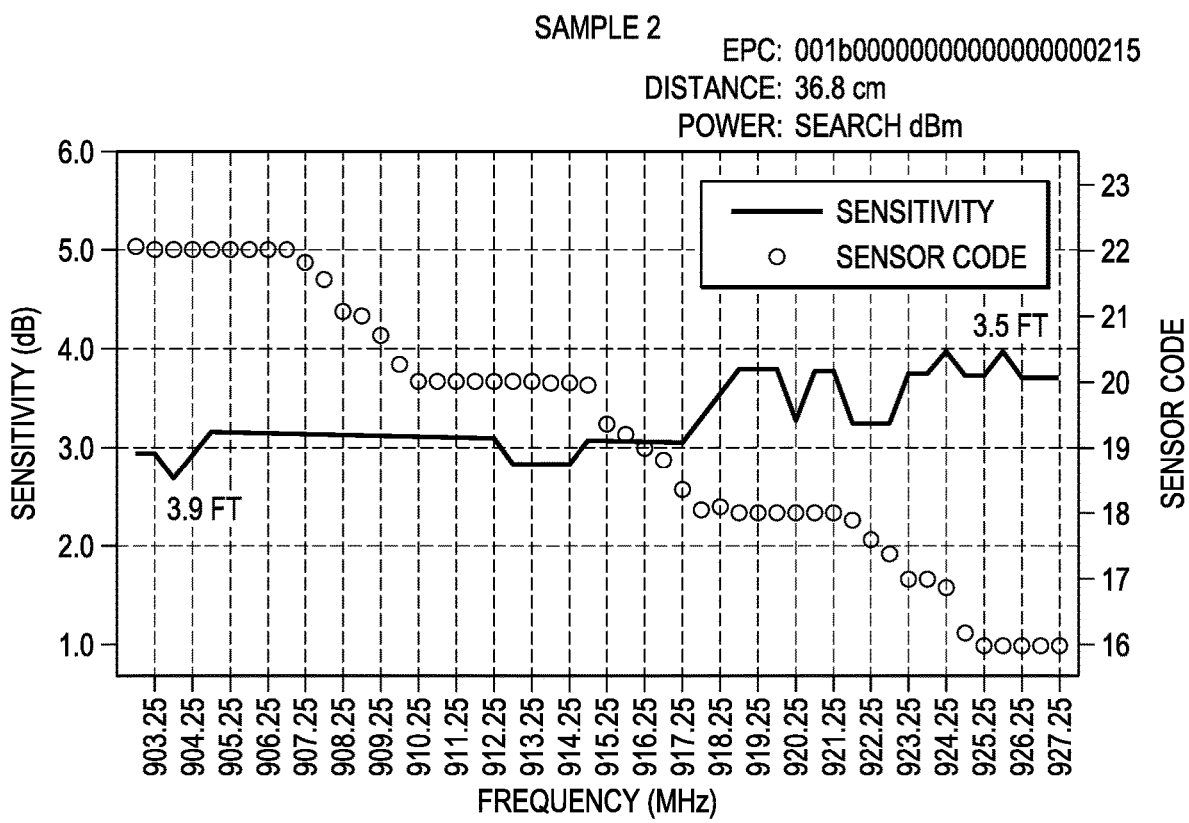
Figure 33:
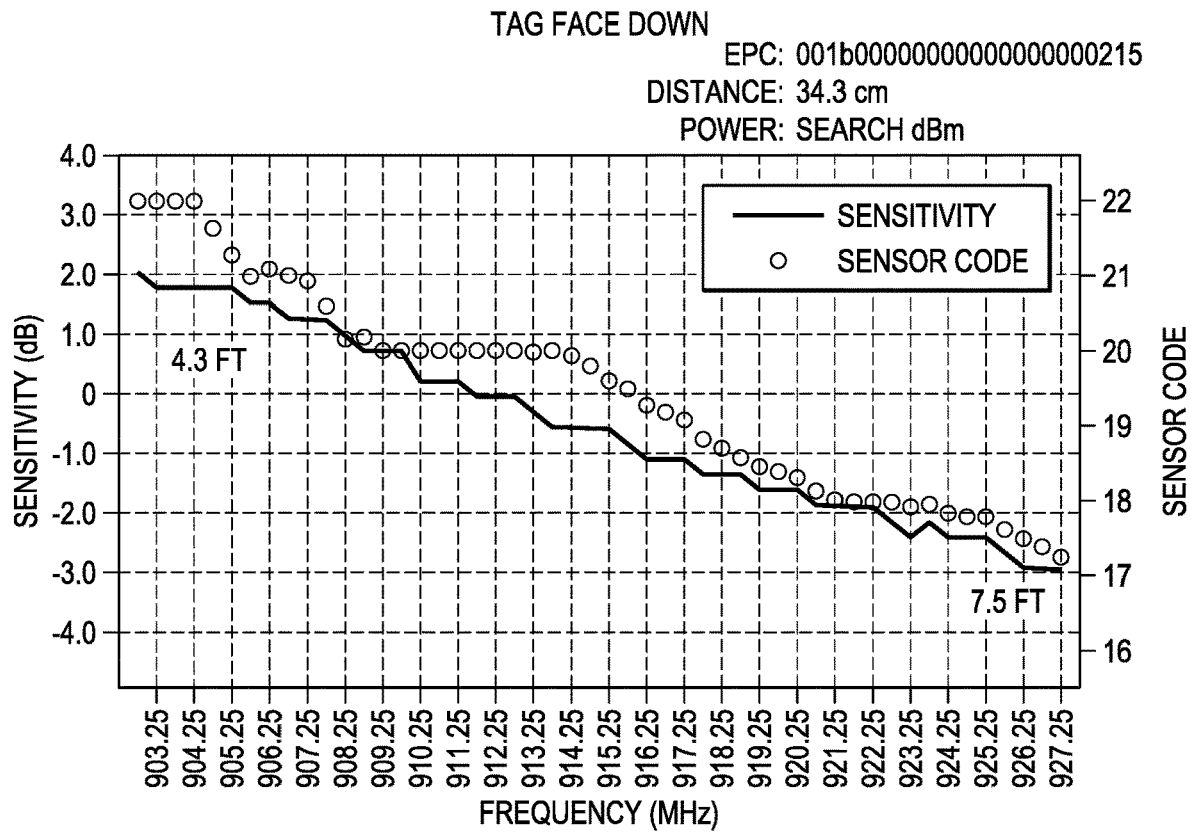
Figure 33:
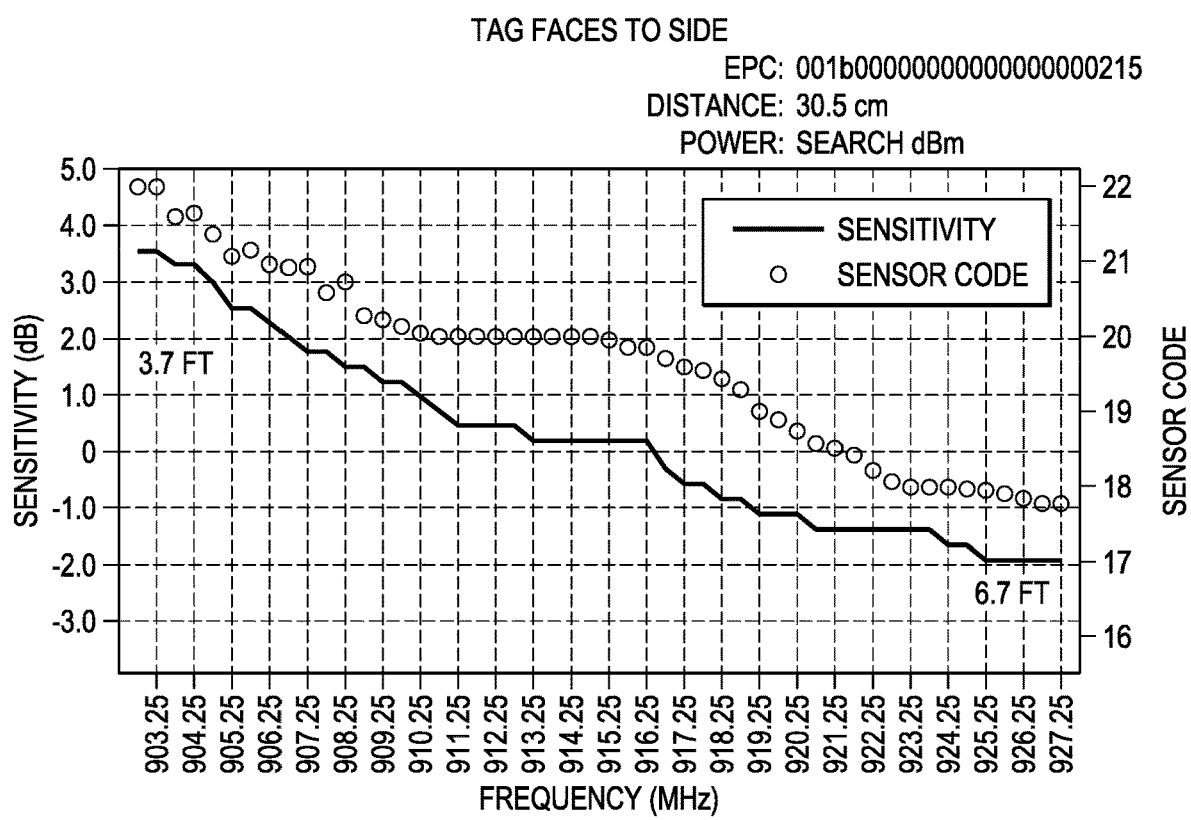
Figure 34:
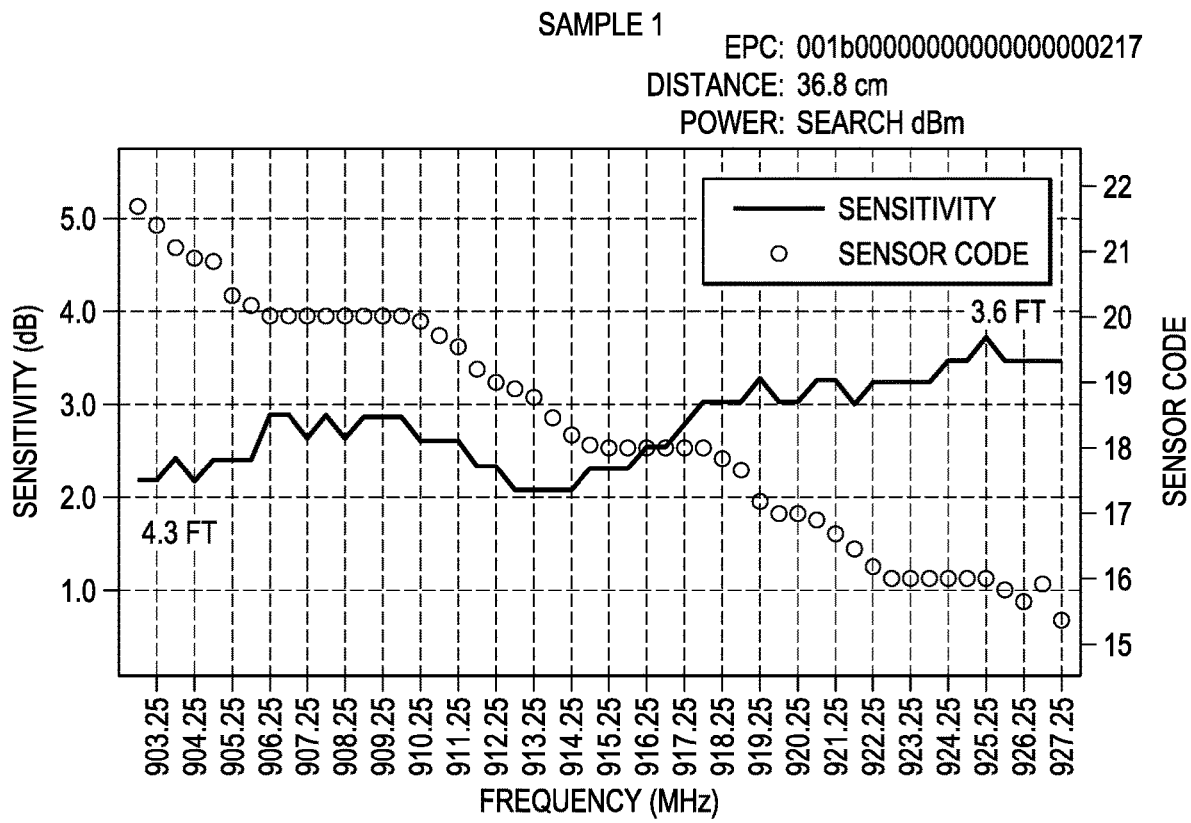
Figure 34:
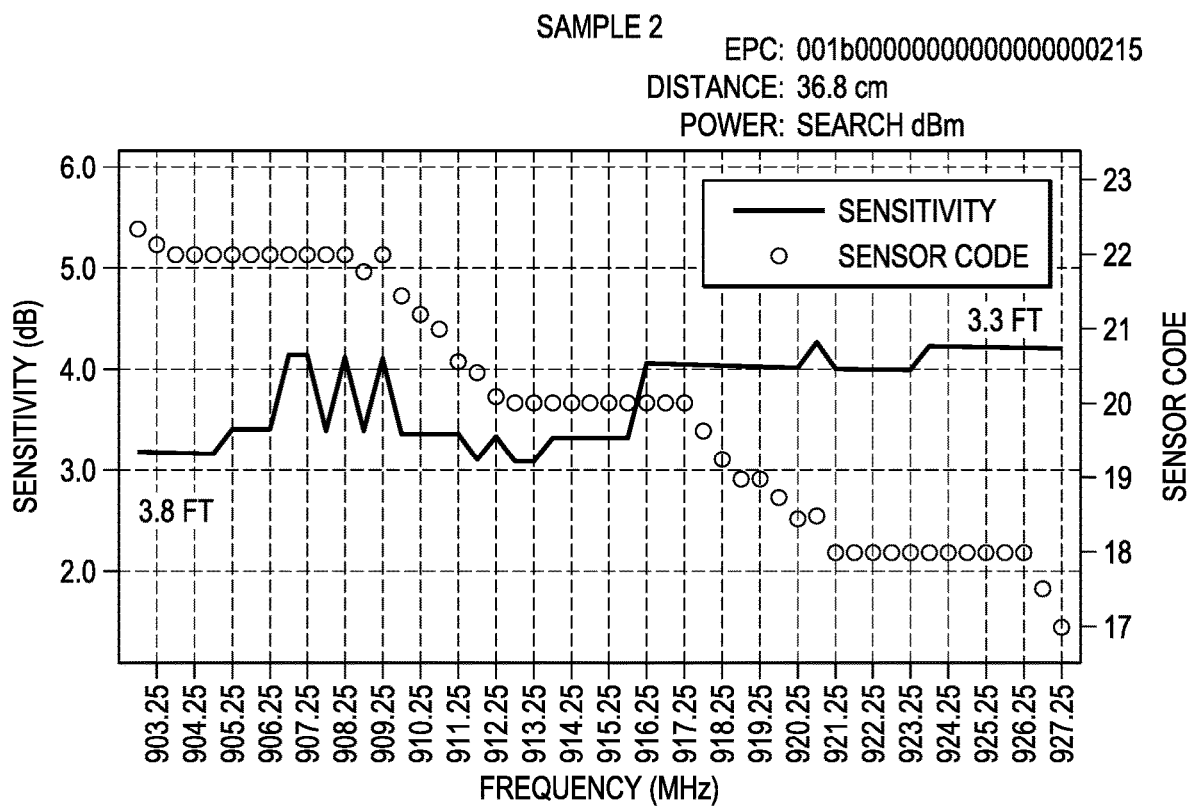
Figure 35:
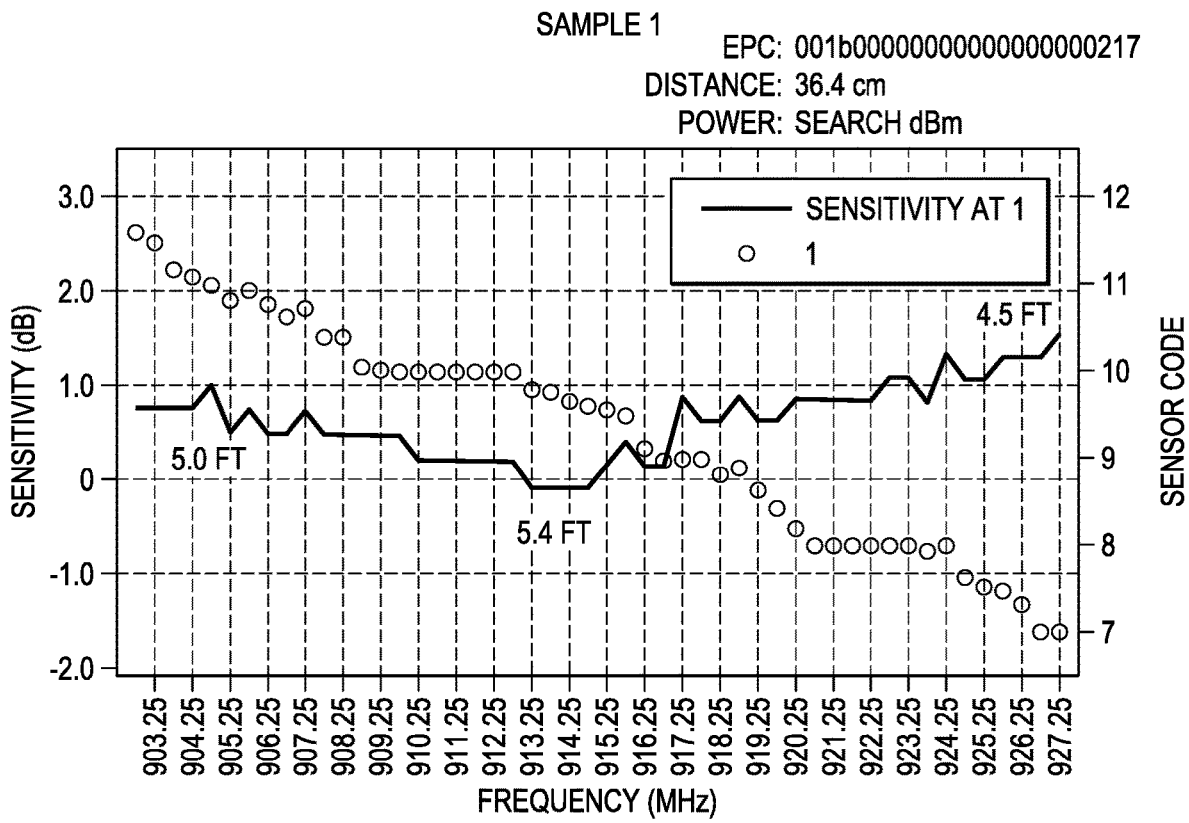
Figure 35:
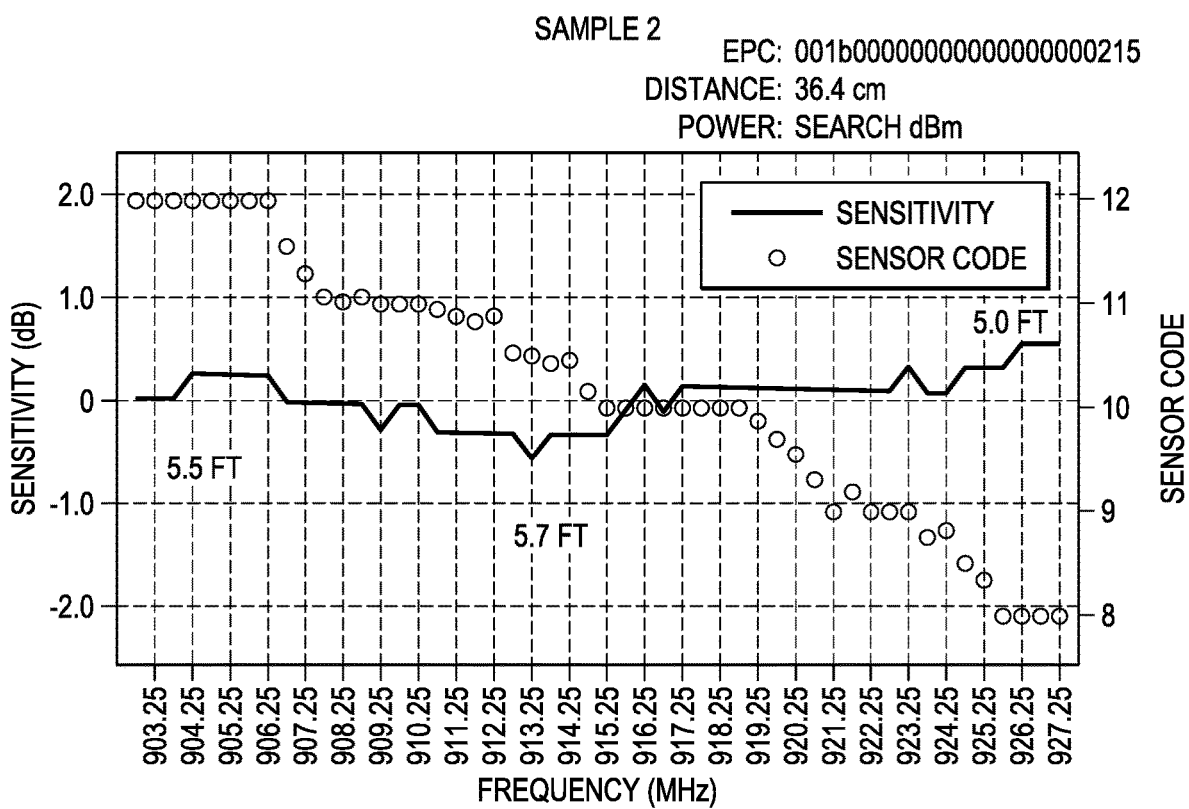
Figure 36:
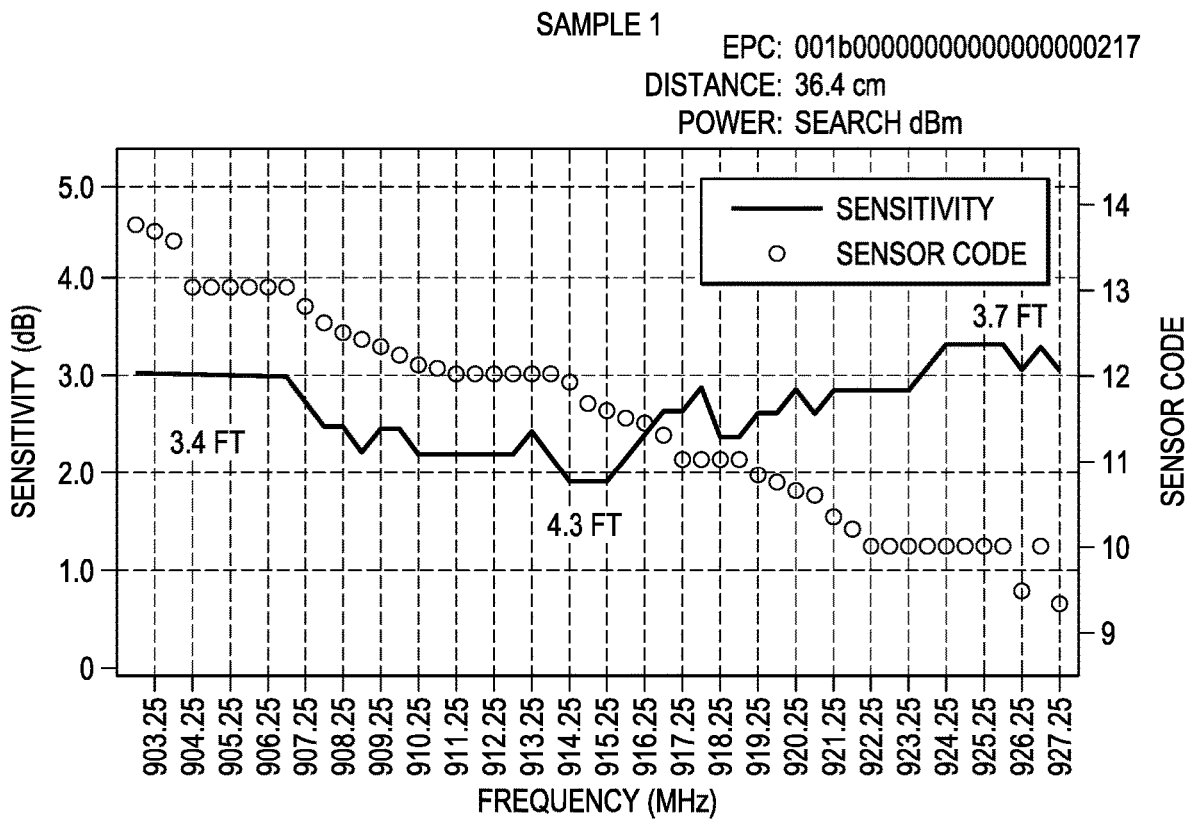
Figure 36:
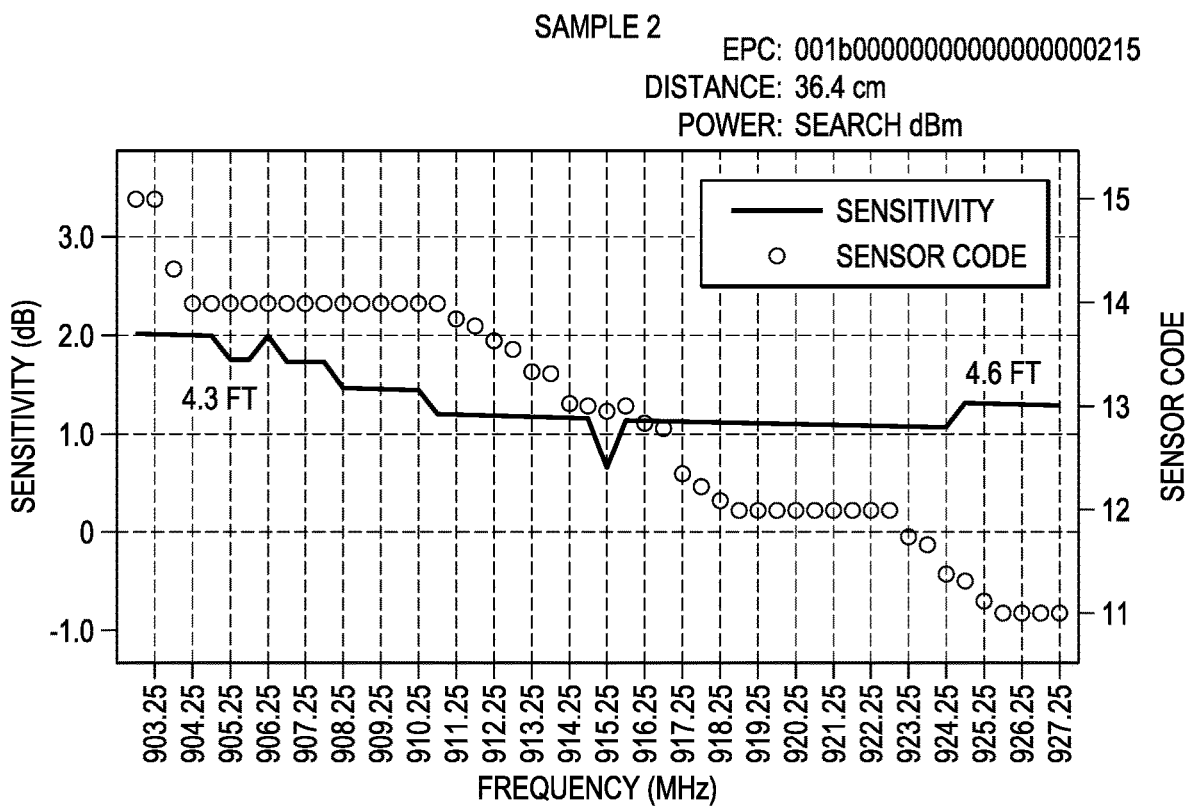
Figure 37:
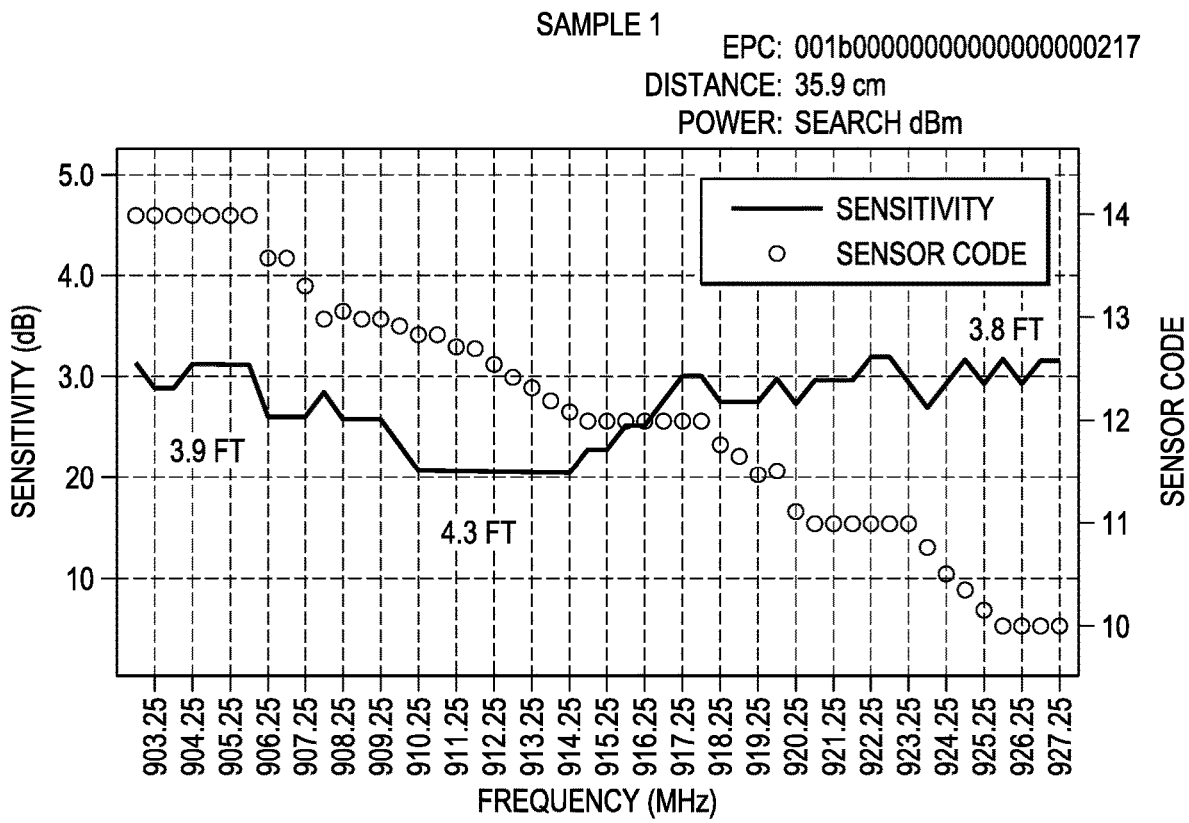
Figure 37:
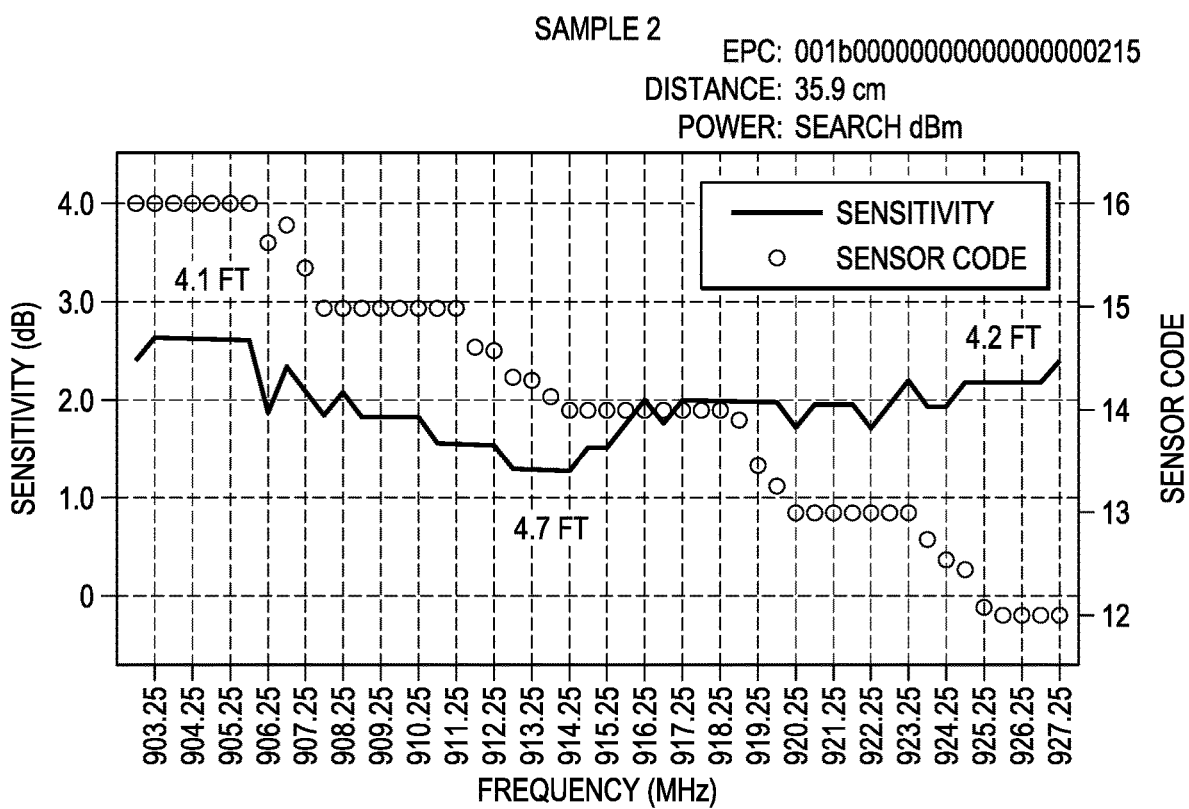
Figure 38:
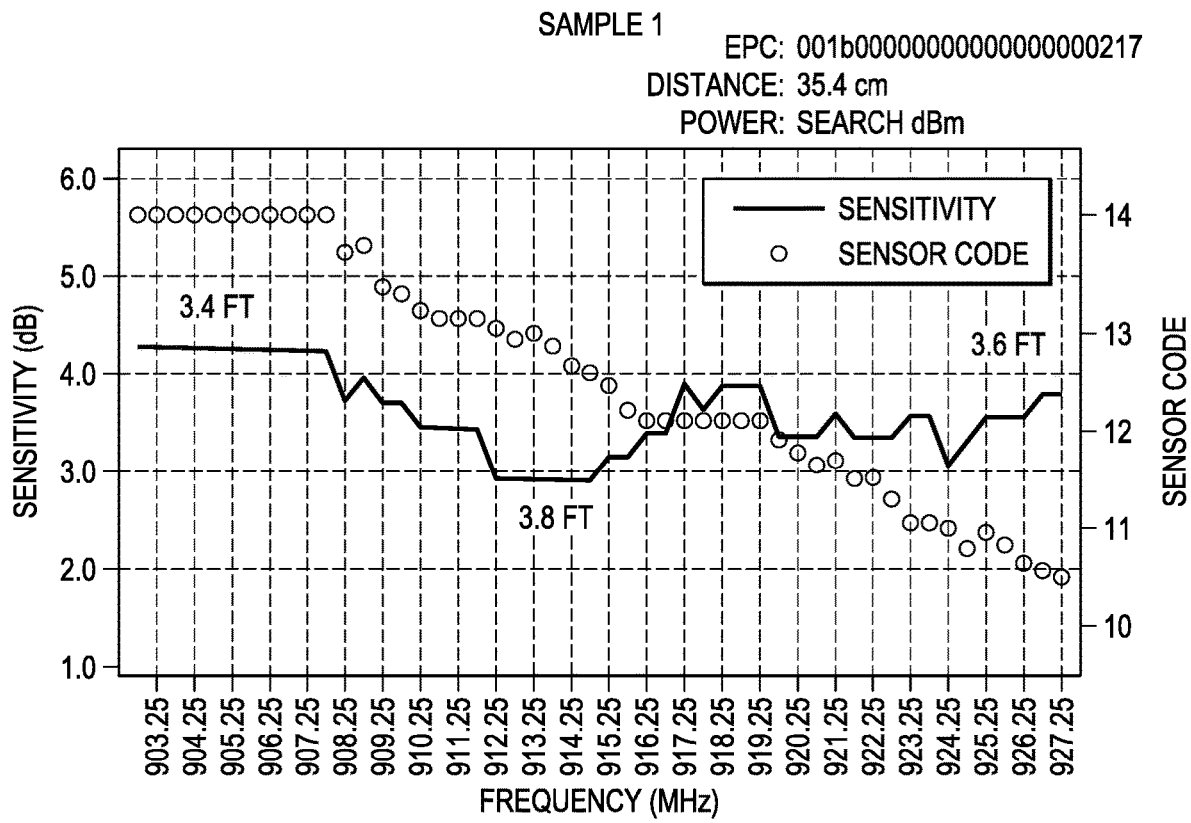
Figure 38:
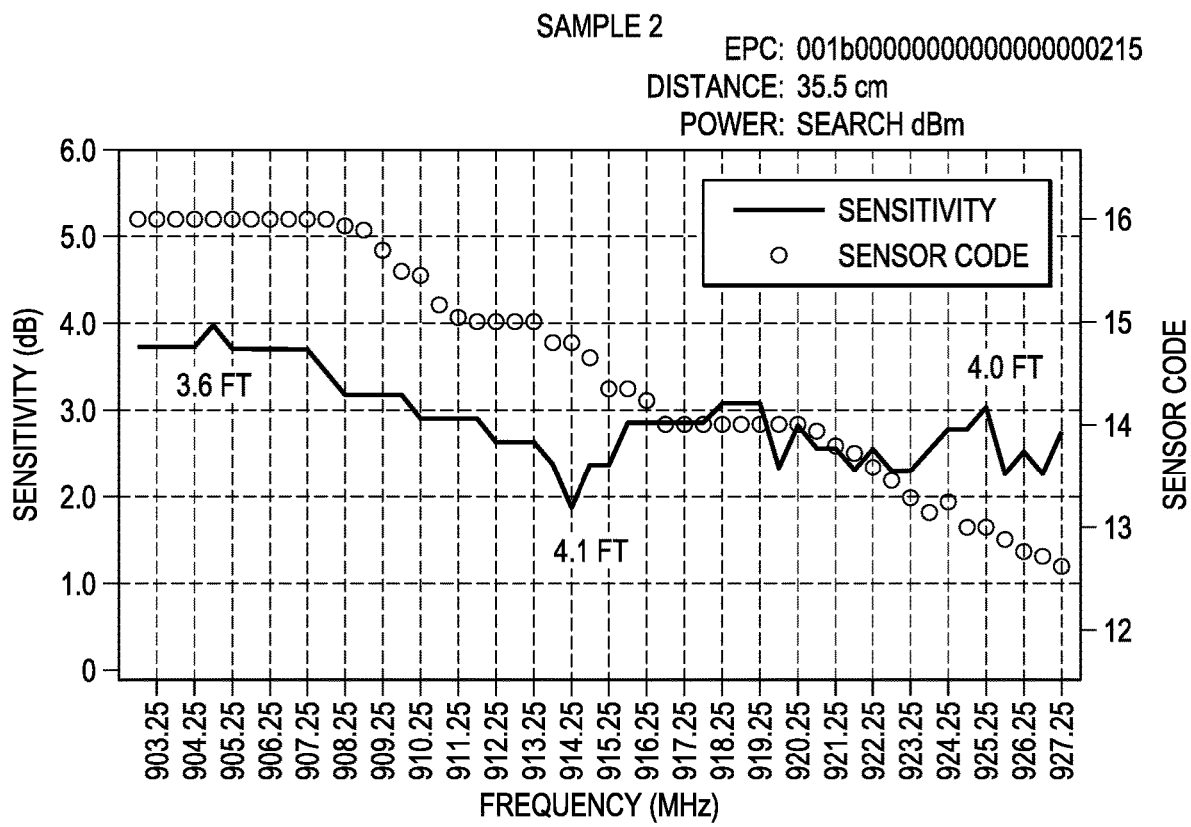

In the FIGs., the sensitivity (measured as explained previously), is plotted (red solid line, in dB) and the sensor code from the impedance matching engine is also plotted (discrete circles). Noted on the figures are range estimates for max FCC power and linear polarization. FIG. 30 is a graph of several measurements taken using a WristTag placed tightly on a human wrist. FIG. 31 is a graph of several measurements taken using a WristTag placed loosely on human wrist (about 10 mm air gap). FIG. 32 is a graph of several measurements taken using a WristTag placed on 2.5" diameter water bottle (results very similar to on-wrist measurements). FIG. 33 is a graph of several measurements taken using a WristTag (Sample 2) placed on 2.5" diameter water bottle with tag in alternate positions: facing down and facing to side (Bottle seems to focus the RF power, the WristTag works better facing away from the reader). FIG. 34 is a graph of several measurements taken using a WristTag off bottle (with 10 MIL PET Spacer inserted between bottle and tag). FIG. 35 is a graph of several measurements taken using a WristTag off bottle (with 3.5 mm air gap between bottle and tag)—these show best performance numbers. FIG. 36 is a graph of several measurements taken using a WristTag off bottle (with 5.5 mm air gap between bottle and tag). The results show a small range reduction compared to the 3.5 mm air gap results. FIG. 37 is a graph of several measurements taken using a WristTag off bottle (with 9 mm air gap between bottle and tag)—From FIG. 37 one can see that the range is similar to 5.5 mm air gap of FIG. 36. FIG. 38 is a graph of several measurements taken using a WristTag off bottle (with 14 mm air gap between bottle and tag)—FIG. 38 shows a slight range reduction compared to the 9 mm air gap measurements. These results demonstrate that the WristTag dual-mode antenna achieves balanced sensitivities across a range of wristband positions.

As can be seen from the sensor code results, the sensor codes from the Self tuning engine are in-range for all configurations (no code saturation) which leaves sufficient codes for adapting to environmental variations. The off-wrist read range is improved vs. the on-wrist read range. The WristTag of FIGS. 29A and 29B operates both tight on the wrist and loose on the wrist. Since the antenna is in close proximity to the body at all times, the sensor code tends to be the same in all positions which leaves plenty of codes to operate the tag as a sensor as well.

By inducing a second mode of operation for tight-on-wrist positioning, the tag sensitivity is maintained while also inducing a large change in sensor code.

Figure 39:
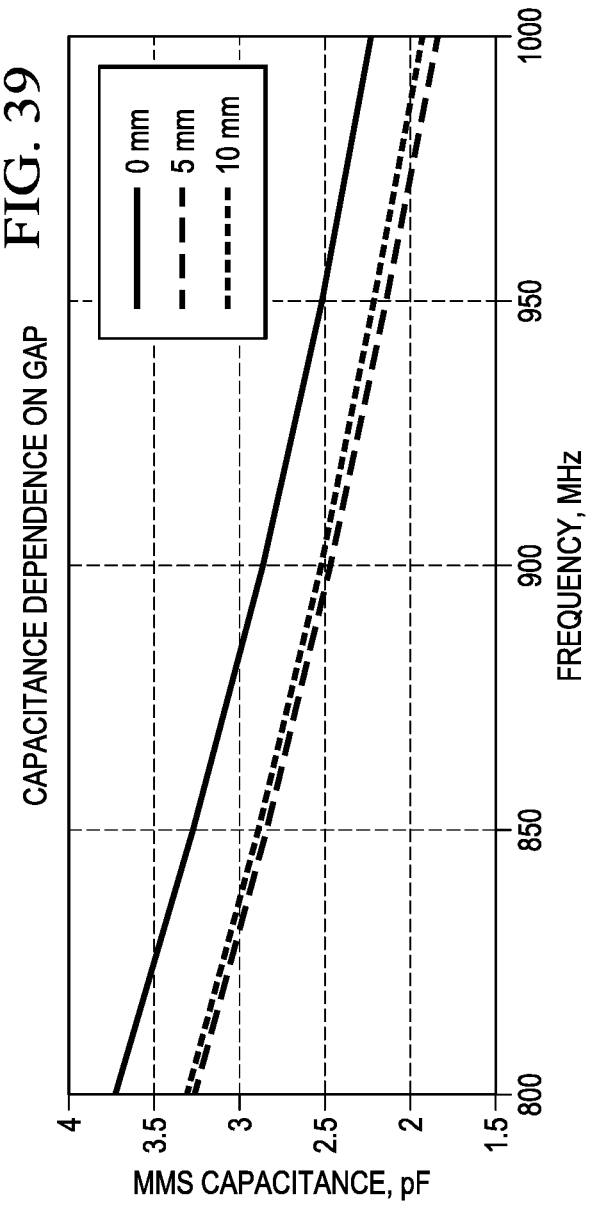
FIG. 39 is a graph of the WristTag capacitance variation vs. air gap in accordance with embodiments of the present disclosure.

FIG. 39 is a graph of the WristTag capacitance variation vs. air gap. The capacitance value in Self tuning engine is set by the generated code. The graph in FIG. 39 shows that the required tuning capacitance is almost identical when the tag is 5 or 10 mm from the body, but there is a jump in required capacitance for on-the-wrist operation.

Figure 40:
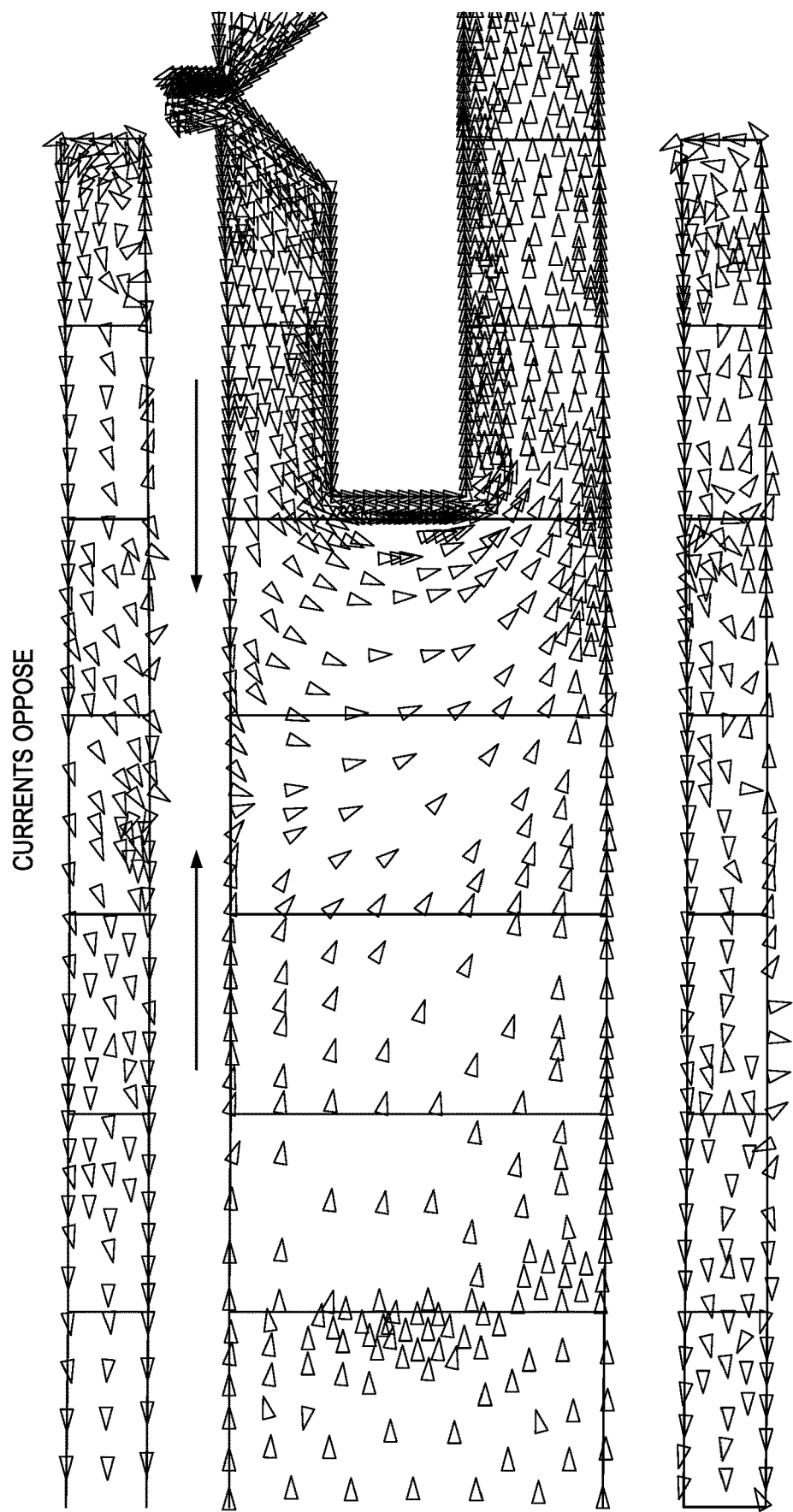
FIGS. 40, 41 and 42 show plots of the internal currents in the antenna with 10 mm gap, 5 mm gap and no gap between antenna and wrist in accordance with embodiments of the present disclosure.
Figure 41:
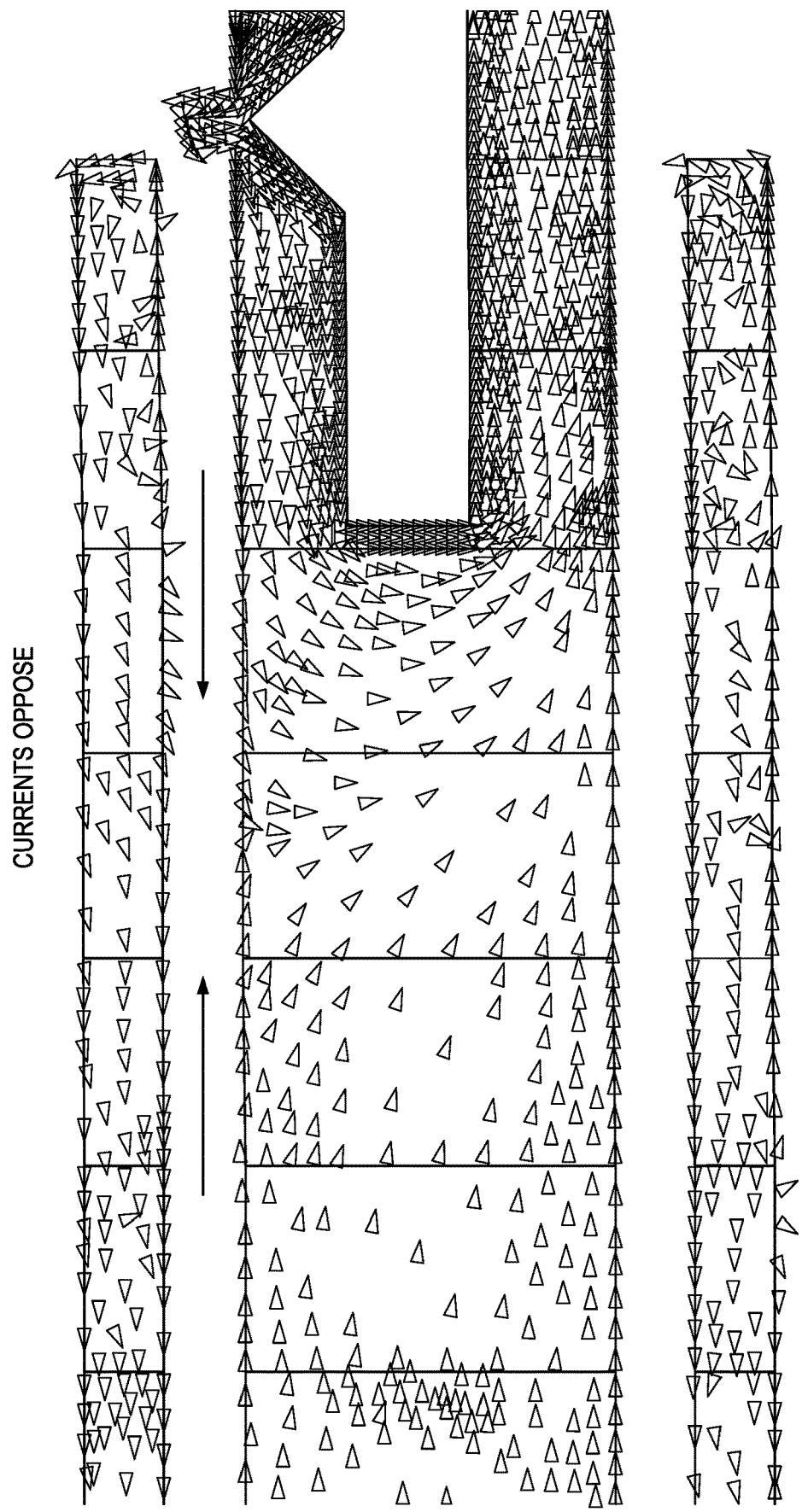
Figure 42:
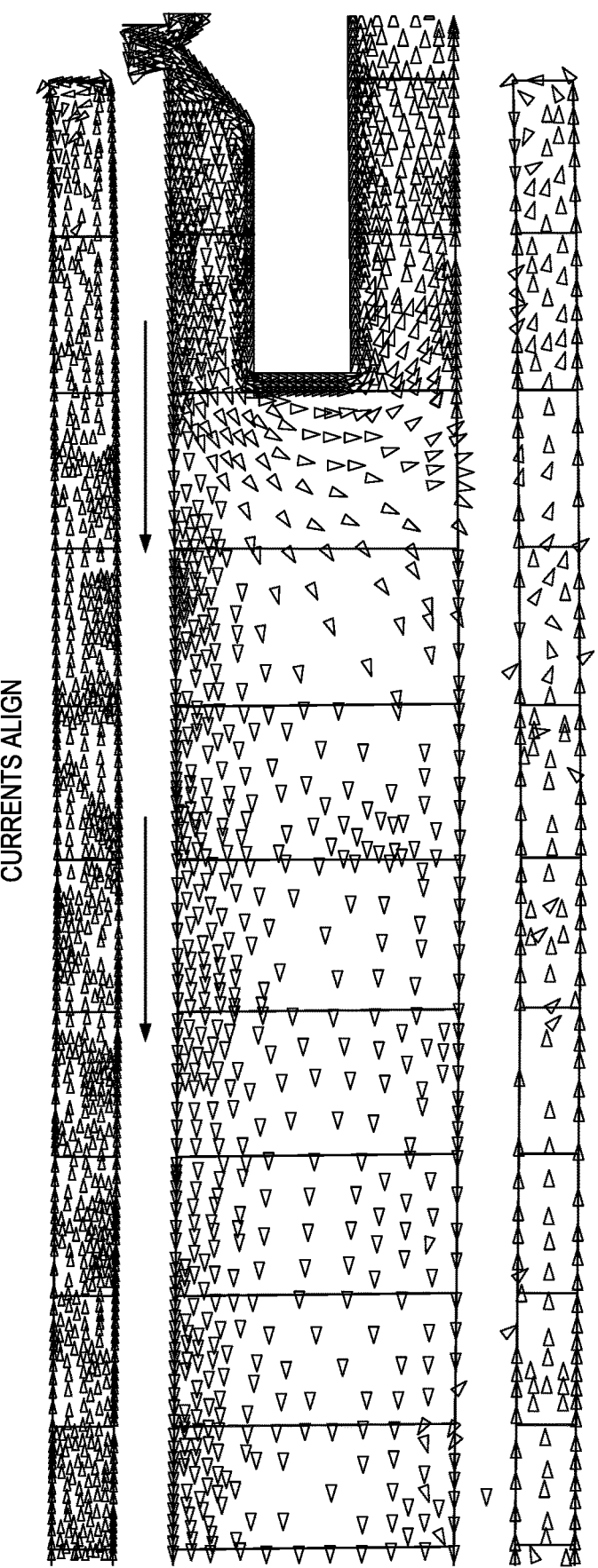

FIGS. 40, 41 and 42 show plots of the internal currents in the antenna with 10 mm gap, 5 mm gap and no gap between antenna and wrist. As can be seen from FIG. 40, the flip in the current direction for tight-on-wrist operation compared to an off-wrist operation (with a gap) as seen in FIG. 40 and FIG. 41 represent a second mode of operation for the antenna. The second mode of operation requires a substantially different tuning capacitance from the die, and this leads directly to a substantially different sensor code. The significant change in the sensor code for on-the-wrist vs. off-the-wrist operation enables the tag to perform a sensor function. For example, the sensor code can be used to determine the proximity of the tag to skin.

Another embodiment of a passive RFID moisture tag/sensor is a diaper tag. The diaper tag is a variation of the WristTag discussed in the previous section that works for a diaper application.

The differences between the diaper tag and the WristTag involve optimizing basic dimensions as required since the diaper tag lays flat and the WristTag wraps around (flat vs. curved), and, improving the performance with three added features. These features include: boxed extensions on the ends, slits in the middle, and a pad of metal inside the tuning inductor. The dual-mode behavior is explained in the previous section. The same physical mechanism occurs for the diaper tag.

Figure 43:
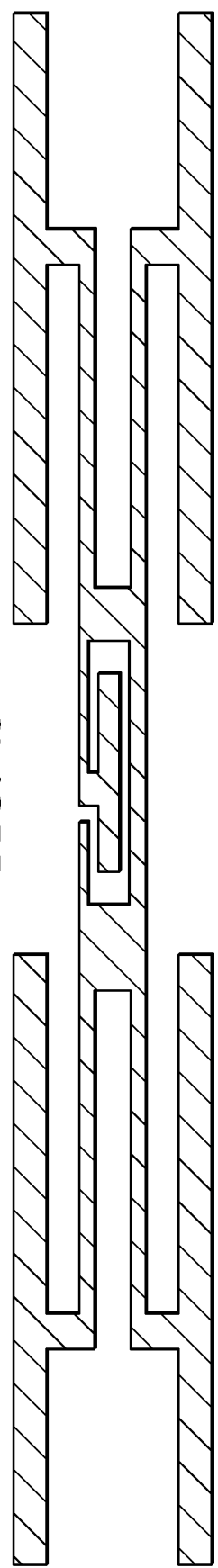
FIG. 43 is a diagram of an embodiment of a diaper tag/sensor in accordance with an embodiment of the present disclosure.

FIG. 43 is a diagram of an embodiment of a diaper tag/sensor in accordance with an embodiment of the present disclosure. In the embodiment, the antenna is a dipole antenna where the radiating elements are the metal sheets extending in two directions and are looped around for various reasons (also referred to as a folded dipole). The dipole uses a standard T-match configuration. Inside of the T-match is a capacitive pad used for tuning purposes. The following measurements on the tag of FIG. 43 were taken on a 1 gallon bottle and all the measurements were taken broadside (i.e. the reader and tag antennas are parallel with the centers lined up). The one gallon bottle is similar to a one gallon milk jug with four corners. Water is added to the diaper at the upper center point and the lower center point. The water was added in 30 ml increments centered on the tag while the diaper stays in place and held down by 3 rubber bands. The "corner" of the water bottle creates a compression line which creates a pinching effect. This causes all absorption on the front side (where the tag is affixed) which becomes highly saturated as water is added. The results show excellent behavior across the 902-928 MHz frequency range and exhibit very large code shifts making the addition of water very detectable by RFID tag/sensor.

Figure 44:
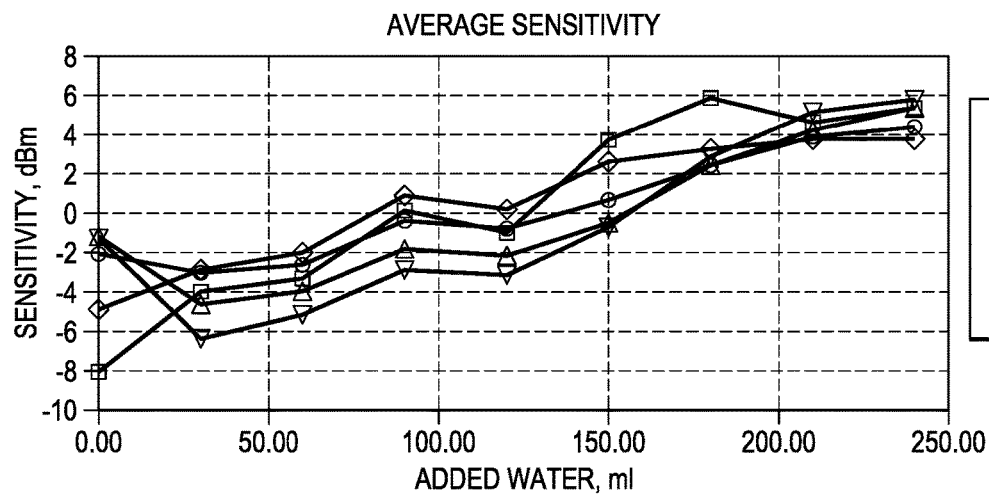
FIG. 44 is a plot of average sensitivity as water is added for various frequency ranges in accordance with embodiments of the present disclosure.
Figure 45:
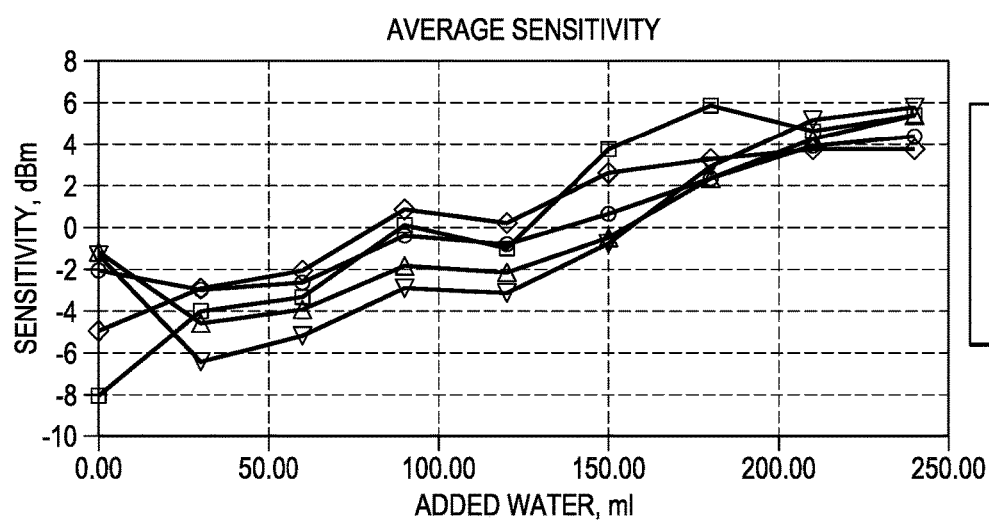
FIG. 45 is a plot of average sensor code as water is added for various frequency ranges in accordance with embodiments of the present disclosure.
Figure 46:
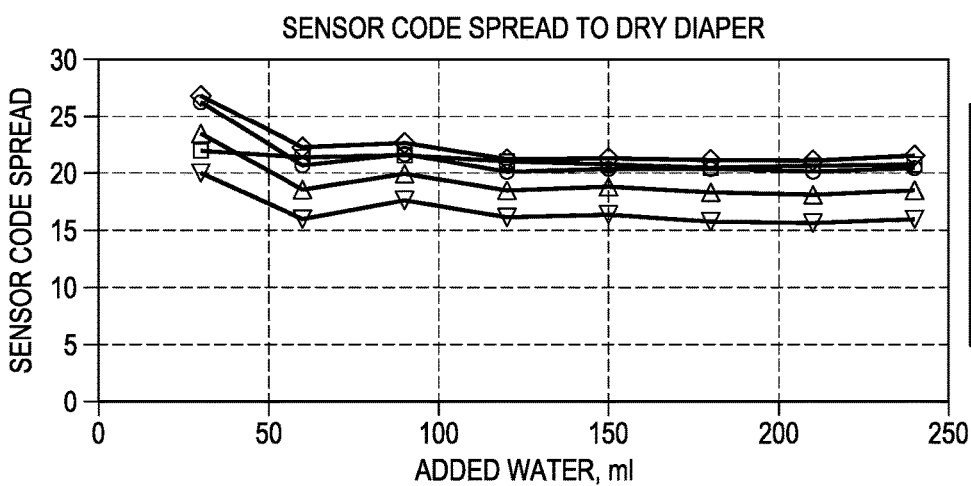
FIG. 46 is a plot of showing the code shift magnitude from a dry condition vs. amount of water added for the various frequency ranges in accordance with embodiments of the present disclosure.

FIG. 44 is a plot of average sensitivity as water is added for various frequency ranges. FIG. 45 is a plot of average sensor code as water is added for various frequency ranges. As can be seen, there is a large code shift for all the frequency ranges from the dry (0 ml) to the wet conditions. FIG. 46 is a plot of showing the code shift magnitude from a dry condition vs. amount of water added for the various frequency ranges.

Figure 47:
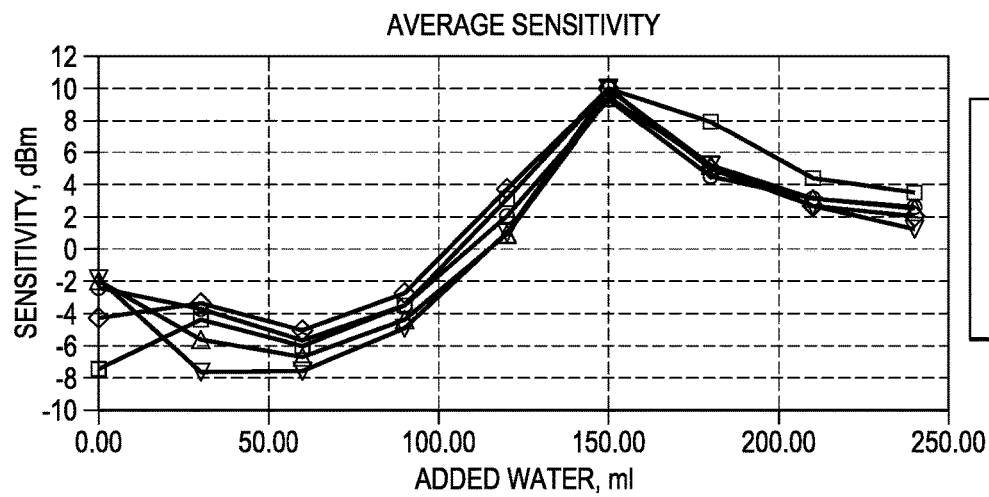
FIGS. 47, 48 and 49 show results of behavior across the 902-928 MHz frequency range and exhibit very large code shifts making the addition of water very detectable by RFID tag/sensor in accordance with embodiments of the present disclosure.
Figure 48:
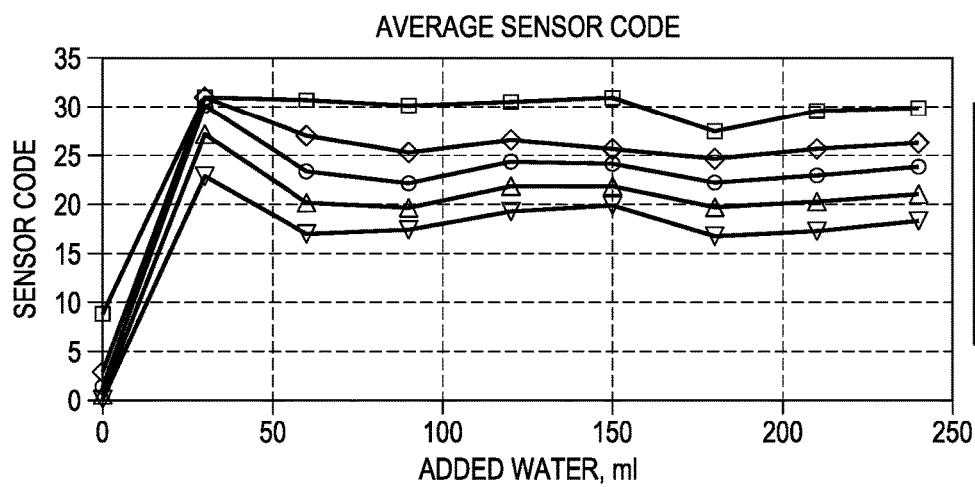
Figure 49:
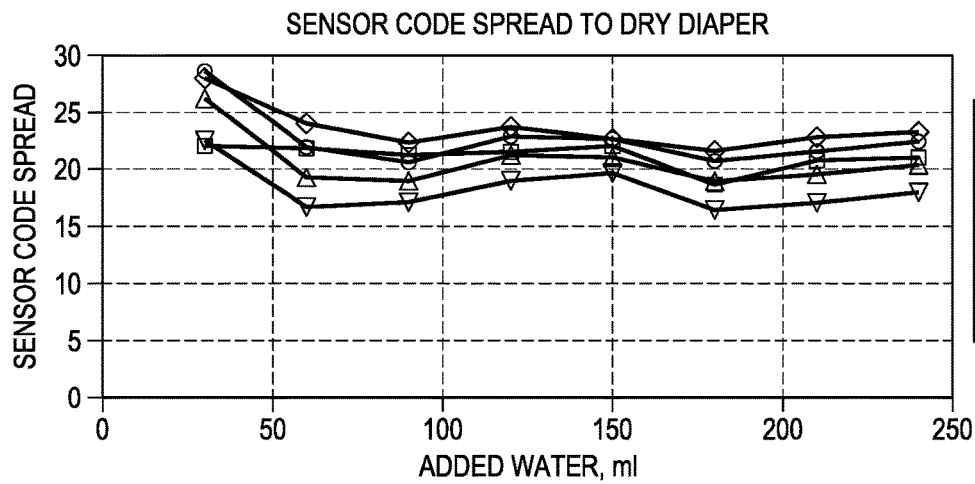

As with the first experiment, FIGS. 47, 48 and 49 show results of excellent behavior across the 902-928 MHz frequency range and exhibit very large code shifts making the addition of water very detectable by RFID tag/sensor.

FIG. 47 is a plot of average sensitivity as water is added for various frequency ranges. FIG. 48 is a plot of average sensor code as water is added for various frequency ranges. As can be seen, there is a large code shift for all the frequency ranges from the dry (0 ml) to the wet conditions. FIG. 49 is a plot of showing the code shift magnitude from a dry condition vs. amount of water added for the various frequency ranges.

Figure 50:
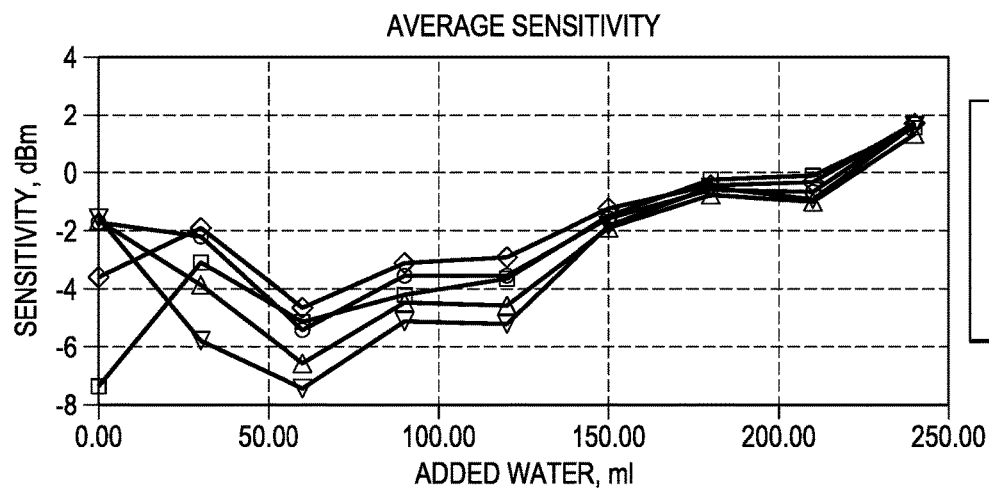
FIGS. 50, 51 and 52 show results where the RFID tag was mounted with the center 120 mm from the edge of the Super-Absorbent Polymer (SAP) filler which is where the water is added to the diaper in accordance with embodiments of the present disclosure.
Figure 51:
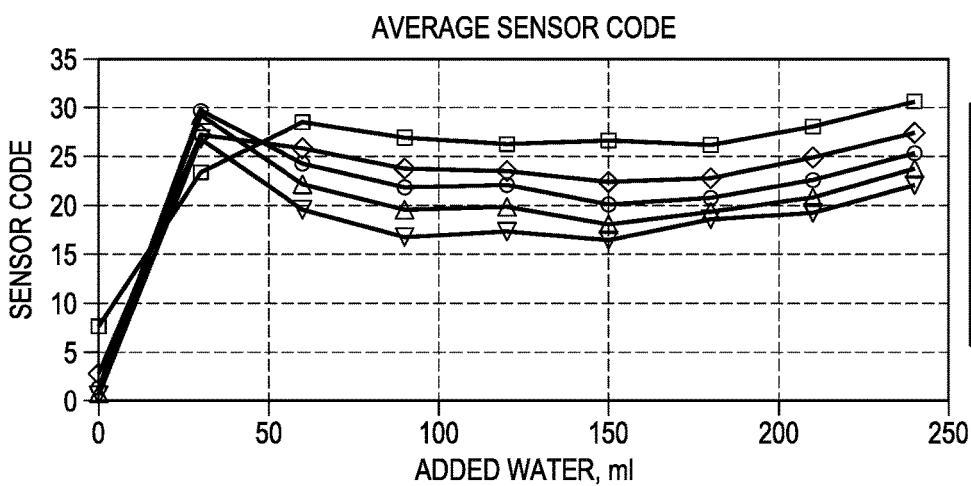
Figure 52:
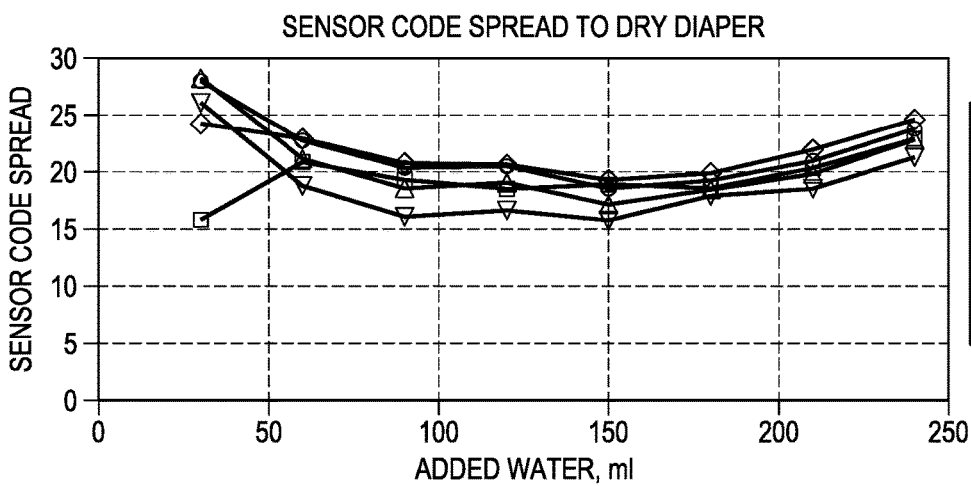

FIGS. 50, 51 and 52 show results where the tag was mounted with the center 120 mm from the edge of the Super-Absorbent Polymer (SAP) filler. Water is added to the center of the diaper. The water was added in 30 ml increments centered on the diaper that is, offset to the tag. In this experiment, the diaper is removed to add water to avoid the "corners" of/the jug from limiting absorption. The bulge that forms is at a 45 degree angle to the antenna and causes a small lensing effect near 180 ml.

As with the previous experiments, the results show excellent behavior across the 902-928 MHz frequency range and exhibit very large code shifts making the addition of water very detectable by RFID tag/sensor. Additionally, the sensitivity for the high water loadings is improved. FIG. 50 is a plot of average sensitivity as water is added for various frequency ranges. FIG. 51 is a plot of average sensor code as water is added for various frequency ranges. As can be seen, there is a large code shift for all the frequency ranges from the dry (0 ml) to the wet conditions. Additionally, there is additional shift at the high water level (near 180 ml). FIG. 52 is a plot of showing the code shift magnitude from a dry condition vs. amount of water added for the various frequency ranges. There is additional shift at the high water level (near 180 ml).

As can be seen from the data above, the diaper tag exhibits the following behavior. The performance is well centered on the North America 902-928 MHz band. Sensor code movement is robust across all measurement setups and diaper fill levels. Easy binary decision: dry for codes<10, wet for codes>10. However, Sensor codes are not giving an indication of "how wet". Sensitivity steadily degrades as the diaper becomes more wet. Wetness centered on the tag measures worst-case sensitivity of about 4 dBm. Offsetting the tag from the wetness measures worst-case sensitivity of about 2 dBm with no penalty in code movement. The offset tag should also produce better sensitivity relative to centered tag due to the raised position of the offset tag giving better line-of-sight to the reader.

Expected field behavior using offset tag placement is as follows: Dry diaper—Best-case read range of about 3 feet. Sensor codes<5. Slightly wet diaper—Read range improves to a maximum of about 4 feet. Sensor code>20. Saturated diaper—Read range degrades to about 2 feet. Sensor code>20.

Figure 53:
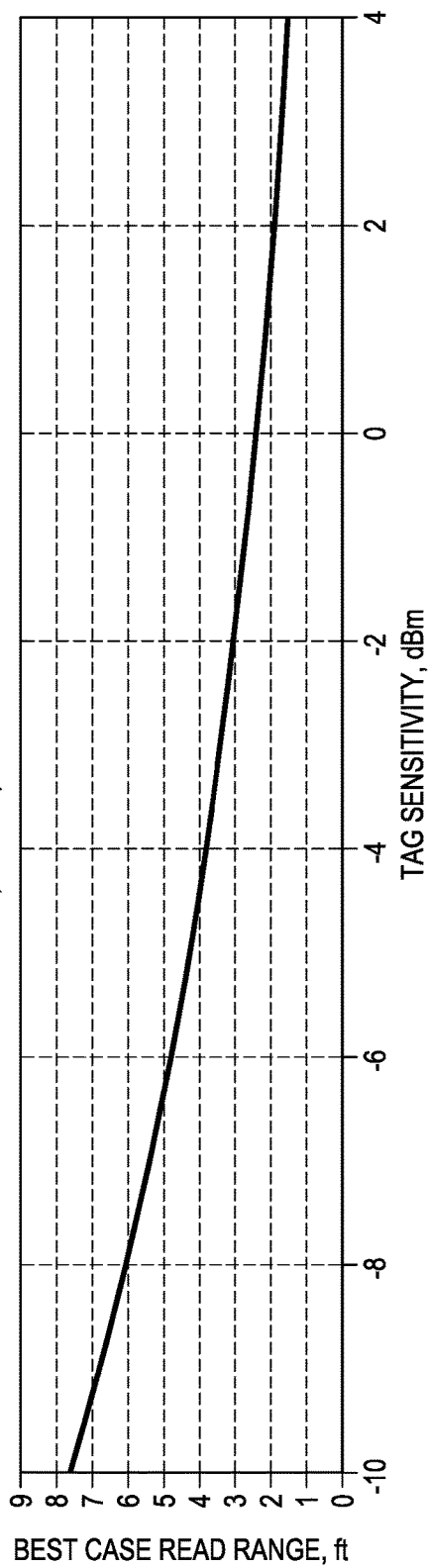
FIG. 53 is a plot of the read range for the hand-held reader in accordance with embodiments of the present disclosure.

FIG. 53 is a plot of the read range for the hand-held reader, best case read range vs. tag sensitivity. Tag sensitivity is always measured because that is the fundamental measure of performance of the tag. The read range of the tag depends on the tag sensitivity and several other use-dependent variables: reader antenna polarization, reader antenna orientation (if linearly polarized), reader output power, and reader antenna gain. The plot in FIG. 53 calculates the expected best-case read range given assumptions for these variables as shown in the plot title: reader output power of 27 dBm, reader antenna gain of 5 dBi, and circular polarization for the reader antenna [so orientation does not matter]. For this application, these assumptions on the reader enable the customer to see what kind of read range they can expect since the tag sensitivity is a somewhat abstract concept to them and they do not know how to convert tag sensitivity to read range. So, the reader considerations were: Assumed: 27 dBm output power, 5 dBi gain antenna, circular polarization; 30 dBm output power and linear antenna would double the read range.

Antennas directly on a water/air interface produce asymmetrical field patterns with far more gain into the water than into the air. In effect, the water sucks in the electromagnetic fields. The effect causes the loss of sensitivity as the diaper becomes more saturated. The effect is reduced as the antenna moves away from the water, as in the dry diaper case. The human body will affect the fields differently than bottles of water, and this will affect the sensitivity of the tags by an unknown amount.

Figure 54:
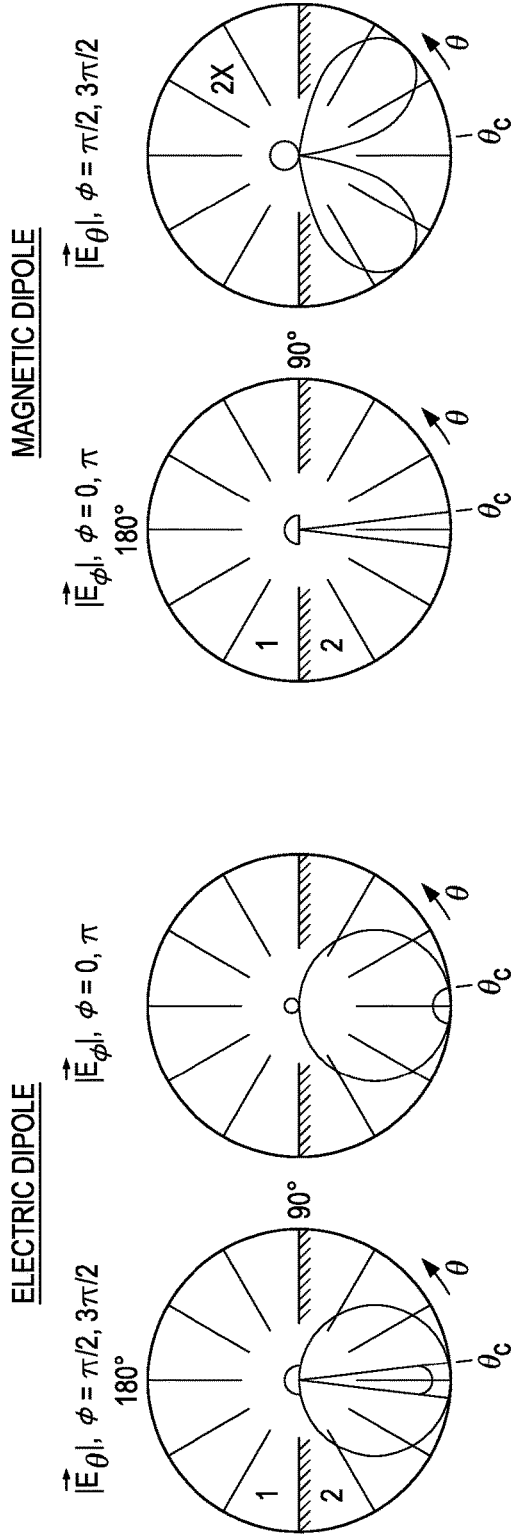
FIG. 54 is a graph showing Antenna behavior at air/water interface (top half labeled 1 is air bottom half labeled 2 is water) in accordance with embodiments of the present disclosure.

FIG. 54 is a graph showing Antenna behavior at air/water interface (top half labeled 1 is air bottom half labeled 2 is water). Because of the high dielectric constant of water, small volumes of water (such as in bottles) tend to resonate and affect results, both in simulation and measurement.

Figure 55A:
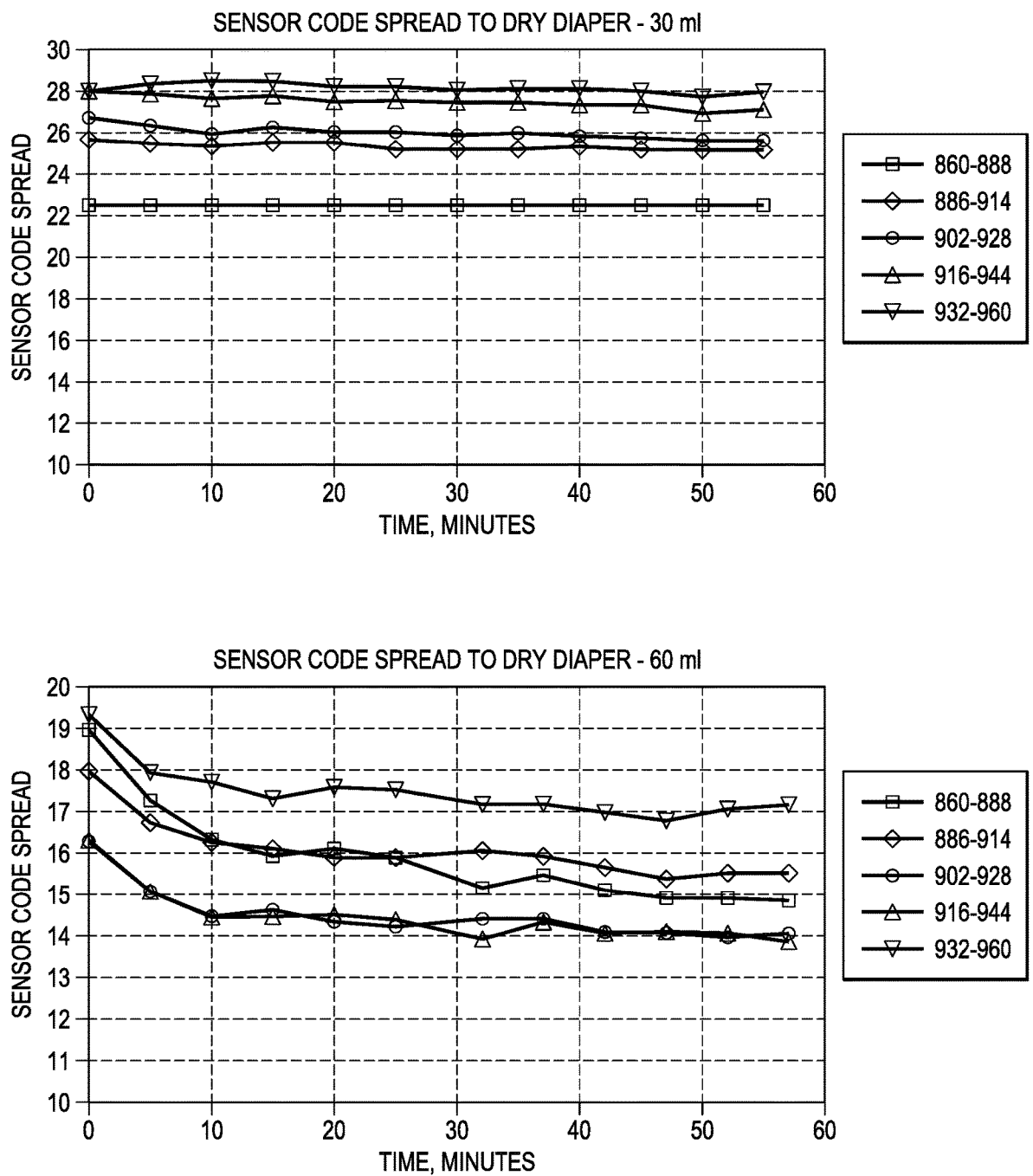
FIGS. 55A and 55B are a set of plots showing sensor code spread vs. time for various frequency ranges and various wetness level (30 ml, 60 ml, 120 ml and 240 ml shown top left, top right, bottom left and bottom right, respectively) in accordance with embodiments of the present disclosure.
Figure 55B:
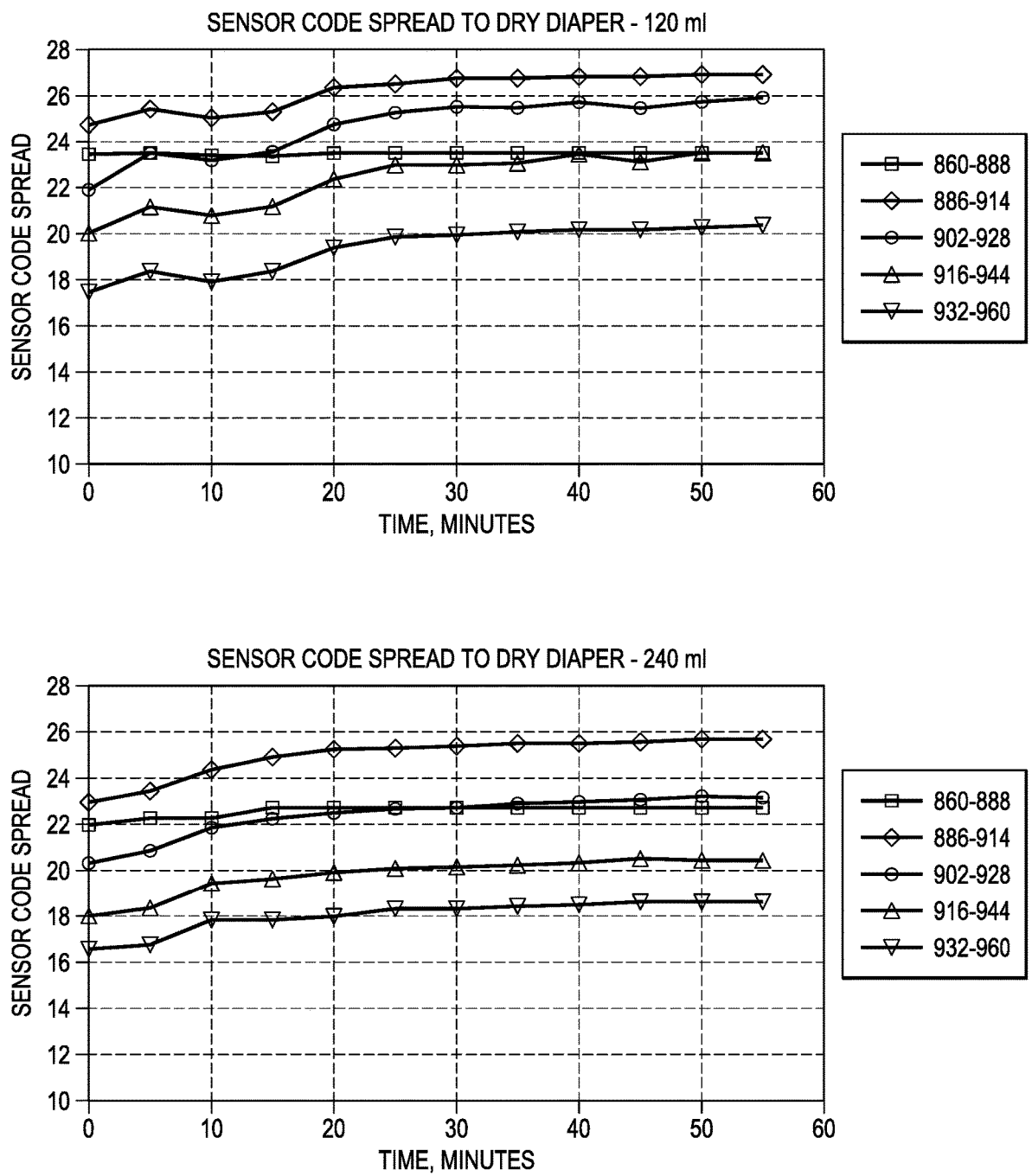

It is possible that diffusion in the super-absorbent polymer (SAP) may cause the sensor codes to move over time. Measurements were made to show the movement of sensor codes over a 1-hour time span. The experiment entailed: The diaper is mounted onto the bottle and the diaper is measured dry. The specified amount of water is added. The measurements are repeated at 5 min intervals without disturbing the bottle. Results show that code movement is not sufficient to affect dry vs. wet decisions. FIGS. 55A and 55B are a set of plots showing sensor code spread vs. time for various frequency ranges and various wetness level (30 ml, 60 ml, 120 ml and 240 ml shown top left, top right, bottom left and bottom right, respectively).

While all the previous measurements discussed were done with the diaper tight against a water jug or bottle, in real life, diapers can develop an air gap due to their own weight pulling them away from the skin. To test for this effect, measurements were repeated with 6 mm of foam inserted between the diaper and the 1 gallon jug of water. Results show that the "saggy" diaper does not significantly impact the measurement system. The sensitivity is slightly improved relative to the tight-on-jug results (experiment #1) and the impact to sensor codes is minor and does not affect the dry vs. wet decisions.

Figure 56:
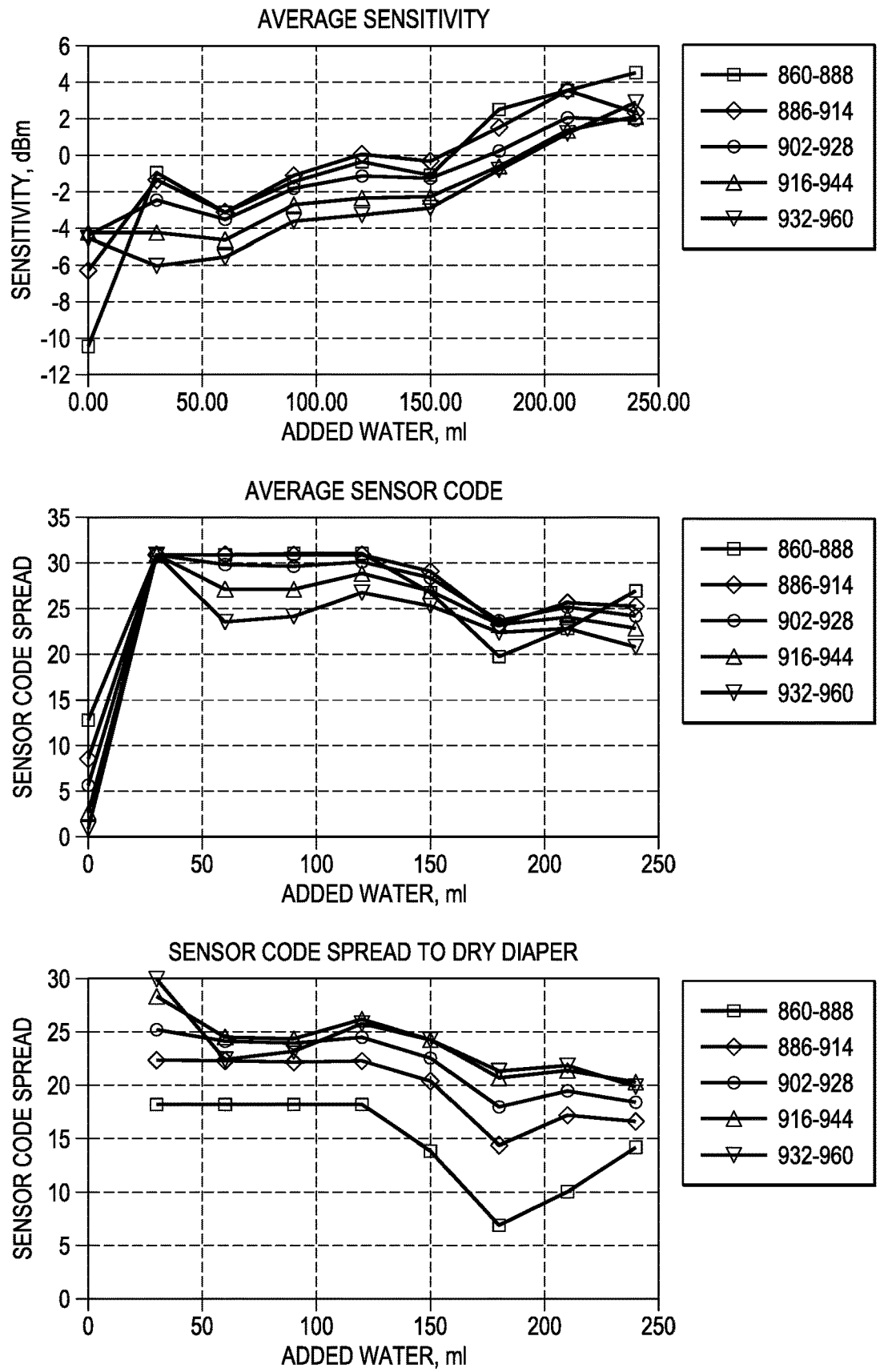
FIG. 56 is a set of plots showing similar to experiments with a 6 mm foam spacer added between the diaper and the jug in accordance with embodiments of the present disclosure.

FIG. 56 is a set of plots showing similar to experiments with a 6 mm foam spacer added between the diaper and the jug.

Figure 57:
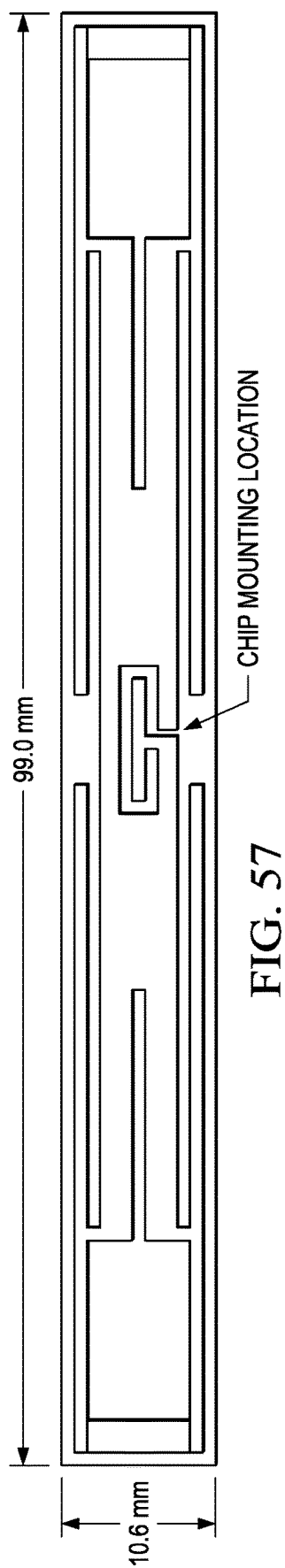
FIG. 57 is another embodiment of the RFID tag/sensor of the present disclosure.

FIG. 57 is another embodiment of the RFID tag/sensor of the present disclosure. The additional changes from the embodiment in FIG. 43 is equalizing the arm lengths on the top and bottom and capping the end extensions. Other embodiments include various changes to end extension lengths, arm attachment location along with body length, lateral slot presence, and lateral slot length.

Figure 58:
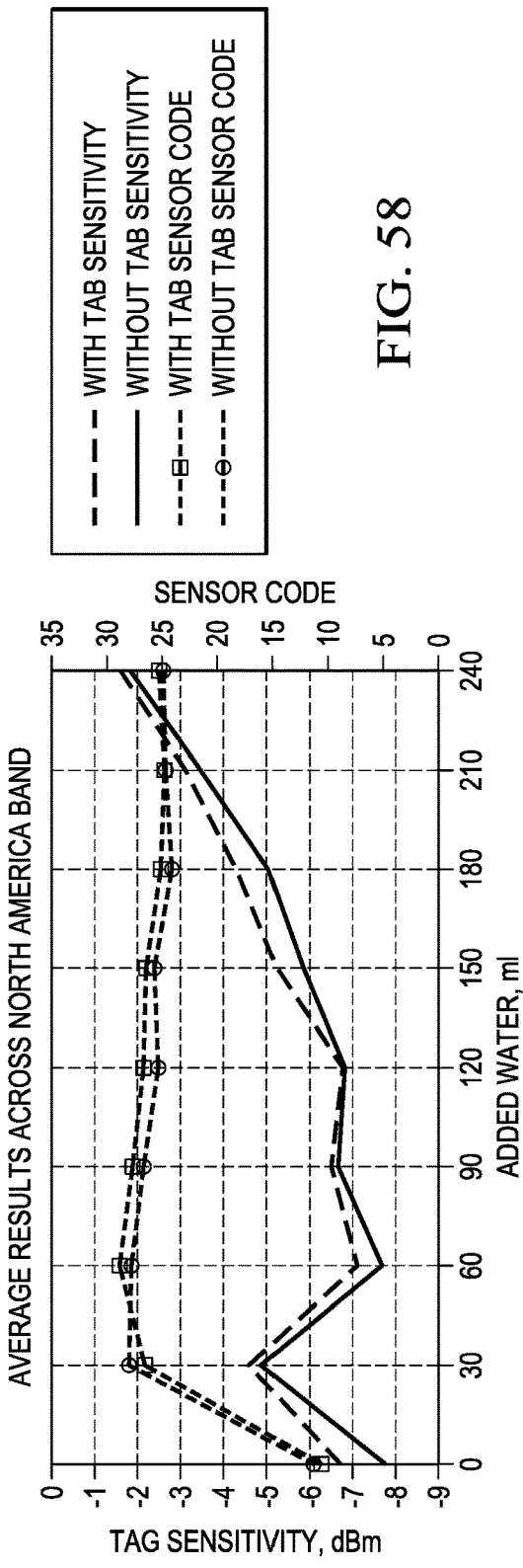
FIG. 58 is a set of plots showing average tag sensitivity across the North American band in accordance with embodiments of the present disclosure.

Experiments regarding placement and identical environment for each measurement show significant sensitivity improvement from 1 to 2 dBm across all wetness levels. It must be noted that both tags provide a robust dry/wet detection ability (threshold, code margin). However, the RFID tag of FIG. 58 alters the load impedance of the transmission lines provided a higher sensor code for the dry diaper that is tunable up or down with small impact on sensitivity if necessary. In the embodiment of FIG. 58, the tab inside the T-match tuning inductor creates an edge-couple capacitor that has little effect in air. With the tag placed on water, the antenna capacitance greatly increases, so a smaller tuning inductor is called for. The edge-coupled capacitor also increases in capacitance tuning out some of the inductance of the tuning inductor and improving the antenna match.

In the diaper application, the RFID tag is placed so that wetness initially occurs past the end of the tag and expands across the tag from one end with added wetness. If the tuning capacitor is in the center of the tag, it may not be needed. The advantage of having a tab is when the moisture hits the diaper directly in the middle of the tab. However, if the diaper tag is such that the moisture creeps up on the tag from one or the other end, then the results show that the tag without the tab will perform similarly. The moisture hitting the tag directly causes the biggest electrical effect, the antenna looks more capacitive so the Self tuning engine sensor code needs to move significantly. In order to get some code sensitivity, the tag codes should not be allowed to saturate (peg at max code) in order to maintain sensitivity and thus read range.

Measurements with the tag mounted off-center from the point where water is introduced show that the capacitive tab has negligible effect (from the edges of the tag). For very wet diapers, the capacitive tab shows benefits (e.g. for male subjects where the tab is likely to be hit directly).

The disclosed RFID tag/sensor are able to detect wetness (moisture) conditions with practical read ranges. In several embodiments, the design performs well over an extremely wide range of conditions. Measurements show robust performance of sensor codes to indicate dry vs. wet diapers with a practical read range. Read range is most affected by fully saturated diapers, where the tag at the air/water interface experiences a fundamental reduction in antenna gain. In an embodiment, offset tag placement is recommended to maximize readability of the tag.

In yet another embodiment a universal moisture tag antenna design is shown in FIG. 59. The antenna can be used with, for example, a Self tuning impedance matching engine (MIIC) with a self-tuning engine as described, for example, in association with FIGS. 3, 4, 5, 6, 8, 11, 15 and 20. The MIIC chip sensitivity is −16.1 dBm. FIG. 61 is a design of another embodiment of a Moisture tag of FIG. 59 antenna (Moisture tag of FIG. 59—MIIC, 89 mm×24 mm (2136 mm2). The antennas are both folded dipoles with conventional T-match tuning. The large width helps with making the antenna performance fairly consistent with changes to the dielectric constant of the mounting surface.

The moisture tag of FIG. 59 achieves a curling of the current in the end pads by widening the trace before it hits the pad. Measurements were taken using RFID tags on dry and wet surfaces of various kinds where wet is defined as 1 or 2 sprays from a water sprayer to simulate the wetness condition. The various surfaces the tags were attached to for the wet/dry measurements were air (foam), wood, PMMA, PET, PTFE and glass. Additionally, measurements were taken on: drywall that is both dry and then saturated with water; on metal with a foam spacers of 13 mm, 6 mm, and 2 mm thickness; on a 1-gallon water jug; on a water bottle, tightly fitted and with 6 mm foam spacer.

The results summarized in the table provided in FIG. 60 were averaged over several materials: Air, wood, PMMA, PET, PTFE, and glass. Dry sensitivity difference is 1.31 dBm, basically the same as the difference between the published sensitivity difference of the MIIC and Monza RFID chips of 1.3 dBm.

The moisture tag of FIG. 59 is more robust under water sprays, with no change in average performance. The moisture tag of FIG. 59 provides more robust performance over prior art antennas. The increased robustness is due to the self tuning engine in combination with the new antenna design. The self tuning engine enables the wet drywall performance to remain flat over the North America band.

The Universal Moisture Tag of FIG. 59 achieves remarkable performance with a 13 mm spacer. The self tuning engine enables excellent performance while it is not coded out. Note that the performance for 6 mm spacer is affected by MMS interference for codes of 10 and lower until it actually codes out at 0. The Self tuning engine enables a 5.9 dBm sensitivity advantage for the moisture tag of FIG. 59 for the worst-case tight-on-bottle position for a 2× advantage in read range. The Self tuning engine provides significant performance improvements in several areas: Average sensitivity improvement up to 0.5 dBm in water spray tests; a 2.7 dBm sensitivity advantage for glass sprayed with water; a 4.6 dBm sensitivity advantage for 13 mm spacing over a ground plane; a 1.2 dBm sensitivity advantage for mounting on a water jug; and a 5.6 dBm sensitivity advantage for mounting tight on a water bottle.

The Moisture tag of FIG. 59 has good code movement in the presence of water: the very damp paper towel placed over the tag. The Moisture tag of FIG. 59 is a good moisture tag for situations with large amounts of water present (i.e. low sensitivity to water) and the Moisture tag of FIG. 61 (explained in the next section) as a moisture tag for situations with small amounts of water present (i.e. high sensitivity to water).

The moisture tag antenna design shown in FIG. 61 may be fabricated using 1 oz copper on 5 mil PET with 2 mil adhesive tape coverlay. An example of a manufacturing construction would use approximately 9 mm Aluminum on approximately 2 mil PET with adhesive coverlay. The antenna is a folded dipole with T-match tuning plus an interdigitated capacitor on top of the T-match box. The antenna design is identical to Moisture tag of FIG. 59 presented previously except for the configuration of the T-match tuning inductor and the interdigitated capacitor. Large width helps with making the antenna performance fairly consistent with changes to the dielectric constant of the mounting surface. Moisture dependence is induced by the interdigitated capacitor. The interdigitated capacitor uses wide gaps to increase fringing to help detect moisture and surface materials.

Testing using the Moisture tag of FIG. 61 with an MIIC (Self tuning engine) on air (on top of foam), air (on top foam) and repeatedly drying the tag, PTFE, PMMA, wood, glass, drywall and PET with wet paper towel demonstrated that sensor code responds progressively with added water. The sensitivity is on target for −18.2 dBm (−16.1 dBm for the chip minus 2.1 antenna gain). Note that some sensitivity is lost due to MMS engine interference for sensor codes of 10 or less. The tag loses sensitivity for codes of 10 and lower. The tag in all water conditions has the same sensitivity while the codes are >10. The mechanism that causes the loss of sensitivity is the MMS engine not being finished adaptively tuning before the first command arrives due to insufficient power. The adaptive engine is still tuning, and this corrupts the incoming signal causing loss of communication. This can be avoided by increasing the reader power so that MMS finishes in time, and this shows up directly as a loss of sensitivity. This only happens for codes of 10 and below and for codes of 28 and up.

The air measurement when repeated with drying of the interdigitated capacitor after each water spray show that sensor code movement is dominated by the capacitor while the antenna is weakly affected by moisture (the fact that the antenna is weakly affected by addition of moisture was shown in the measurements of Moisture tag of FIG. 59).

The Moisture tag of FIG. 59 is insensitive to small and modest amounts of water applied by spraying water onto the tag. The sensitivity to water is increased by adding an interdigitated capacitor to create the Universal Moisture Tag of FIG. 61, which shows good code movement to water applied by spraying the tag. Note that sensitivity is impacted whenever the sensor code drops to 10 or less (MMS engine interference described earlier). For a very wet case, created by fully saturating one layer of paper towel, the Universal Moisture Tag of FIG. 61 may be sensitive with the code pegging low and a big loss of sensitivity. Since the Universal Moisture Tag of FIG. 59 is far less sensitive to water than the Universal Moisture Tag of FIG. 61, the Universal Moisture Tag of FIG. 59 is highly effective for this case with only a 3 dBm reduction in sensitivity.

The Universal Moisture Tag of FIG. 59 is an excellent foundation for moisture tags in general: Use the tag in its basic form for heavy concentrations of water. Add an interdigitated capacitor to increase sensitivity to smaller amounts of water. The larger the capacitor, the greater the sensitivity. The tradeoff is the range of moisture concentrations to be detected.

In yet another embodiment of the current invention, a moisture tag antenna design is shown in FIGS. 62, 63, 64 and 65. These antennas can be used with, for example, the IC 2000 and self tuning impedance matching engine (MIIC).

These antenna types may be folded ¼-wavelength patch antenna radiating from one edge. The use is any on-metal application. The prototype of the embodiment is made of 1 oz Cu laminated with transfer tape onto 5 mil PET. The spacer is 3M VHB acrylic foam tape 0.4 mm thick. Three layers of foam tape are used to build up the complete spacer ~1.2 mm thick. The Cu/PET lamination is then cut, IC 2000 is attached, and then folded around the spacer. IC 2000 ends up on the inside of the folded structure. The production tag may use aluminum on 2 mil PET along with the 3M VHB spacer.

Other embodiments are constructed by reducing the overhang, where the overhang is the distance from the metal to the edge of the substrate. The overhang can be increased or decreased without requiring antenna re-design.

Figure 62:
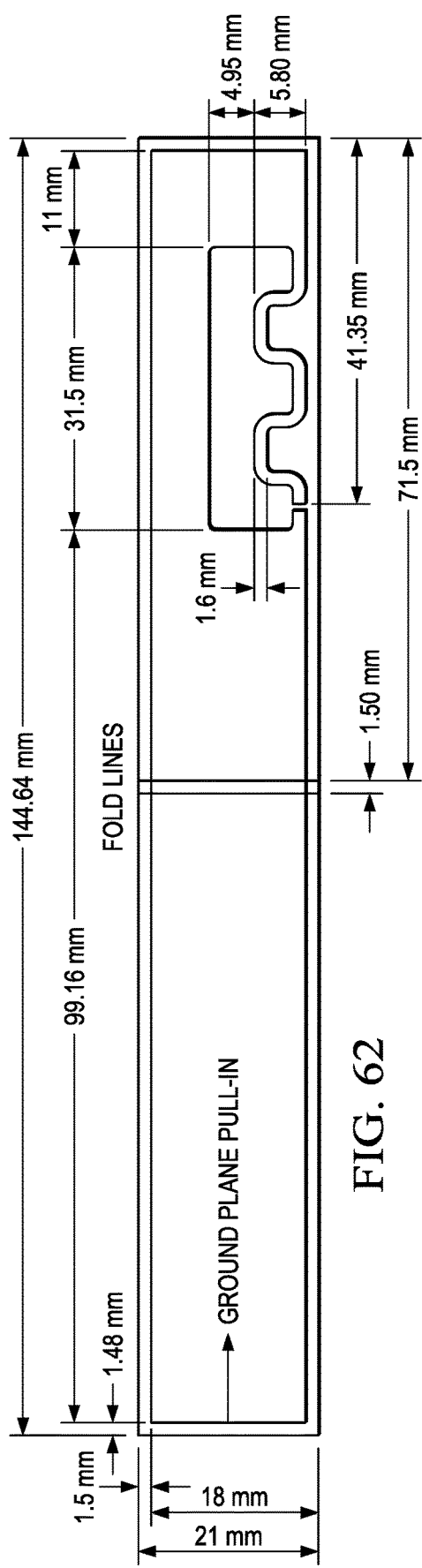
FIGS. 62, 63, 64 and 65 are schematics of yet other embodiments of a moisture tag antenna design where these antenna can be used with, for example, the IC of FIG. 20 in accordance with embodiments of the present disclosure.

Yet another embodiment can be constructed by decrease ground plane length (e.g. FIG. 62). The ground plane can be pulled in to improve performance by a small amount at the expense of increasing performance variability due to adhesive tape thickness. Typical distance is 2-3 mm. Radiation efficiency is enhanced when the gap between the top metal plate and bottom metal plate is increased. This directly improves tag sensitivity. The spacing between the plates is 1.2 mm for this tag. If the bottom metal plate is cut back by 2-3 mm, then the spacing is increased by the thickness of the adhesive tape, and let's call that 3 mil, or 75 um. The gap is now 1.275 mm, or 6.25% larger. This is not a lot, but it is significant. Since the bottom metal plate is capacitively coupled to the metal surface on which the tag is attached, they are effectively shorted together. Now the tag is slightly dependent on the tape thickness.

The embodiments show excellent sensitivity for its size of (−8 dBm), very wide bandwidth, and good response to water that is dependent on the overhang length.

Figure 63:
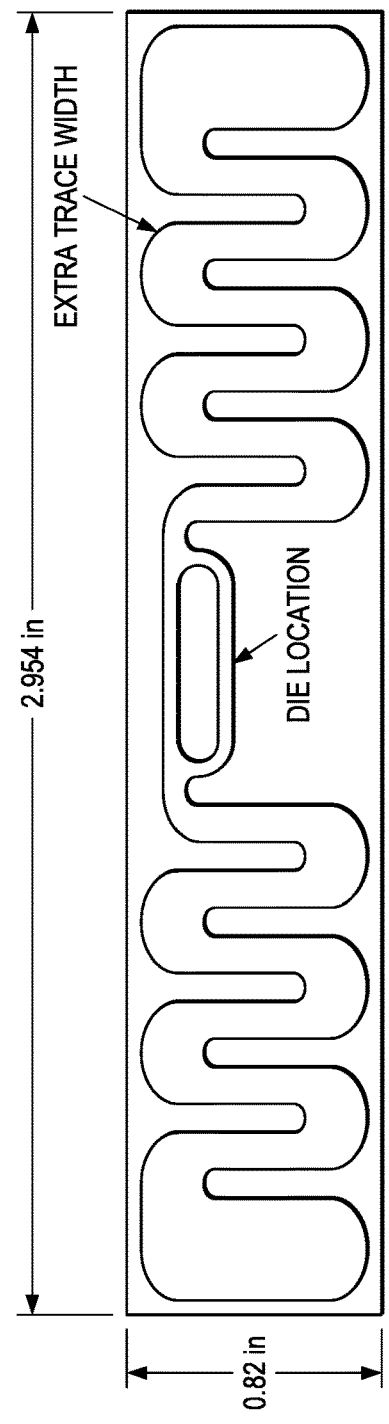
Figure 64:
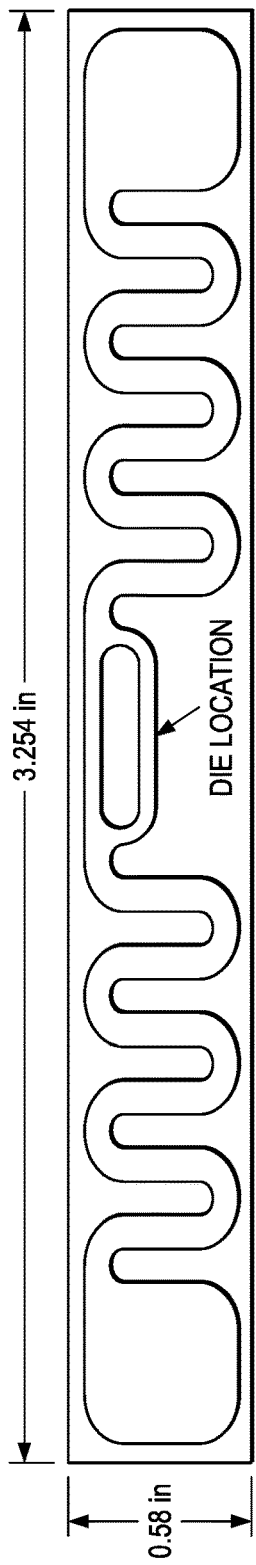
Figure 65:
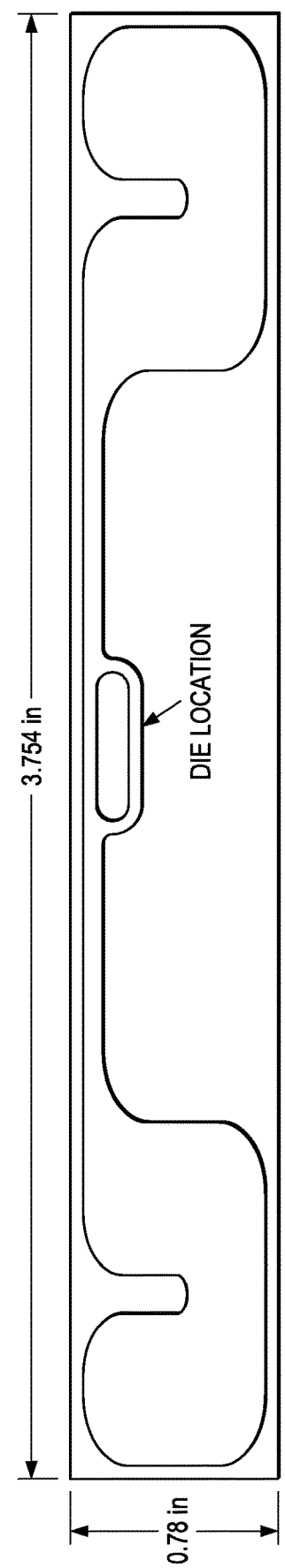

In yet another embodiment of the current invention, three more moisture tag antenna designs are shown in FIGS. 63, 64 and 65. The antenna can be used with, for example, the IC 2000 with the self tuning impedance matching engine. These antennas have been optimized for sensing moisture in, for example, a stack of wood veneers stacked on top of each other, usually referred to as a pallet.

An example pallet consists of 8'×8' wood veneers stacked 2 meters high. An example placement of RFID sensors is in the center of the stack. One ore more tags are inserted into the stack at various positions. These positions can vary in both the X, Y and Z directions. That is, placed between different layers at different depths from the edges. For this embodiment, three such tags are inserted about 1 m from the top and approximately 20-30 cm from the edge.

Moisture sensing can be achieved with a single tag. In another embodiment, the results from multiple sensors may be averaged to produce a single sensor code for the pallet. In yet another embodiment, the multiple sensors readings may be weighted in order to provide more weight to a sensor that is embedded deeper in the pallet or alternatively to provide more weight to a sensor that is at the edge. Such weighting is dependent, for example, on location of where the pallet is to be stored and/or environmental conditions around it. Additionally, such weighting maybe dynamically coprogrammable by the user in order to change such weighting from one pallet to another. Such computation can be easily programmed in the reader or any other device eventually receiving the code.

While various moisture levels can be measured depending on the design of the tag, for this particular embodiment moisture content levels from 2-10% are to be measured. The system measures the moisture content in absolute terms with +/−2% accuracy with a read range target that is greater than 1 m using both fixed and handheld readers.

FIG. 64 shows a conventional compact dipole with T-match optimized to be embedded in wood with dielectric constants ranging from 2 to 5. Conventional design using meandered dipole with T-match and capacitive pad loading at the ends. The dimensions may be optimized to achieve best performance when completely buried in moist wood with composite dielectric constants ranging from 2 to 5. Dry wood has a dielectric constant a little over 2, while wood with moisture content of 10% by weight has a dielectric constant near 5. Performance is defined as maximum movement in antenna inductance as the capacitance changes from 2 to 5 while maintaining antenna gain within dB of the ideal dipole gain of 2.2 dBi. Maximum movement in antenna inductance means that the self tuning engine will achieve maximum sensor code movement for detecting changes in moisture content of the wood. The changing moisture content of the wood changes the capacitance of the RFID tag, that the self tuning engine reacts to.

FIG. 63 shows a modification of the antenna of FIG. 64 to add excess capacitance in the meander routing to increase coupling to the wood for slightly improved sensitivity to moisture level. The design here is modified to increase the trace width at the bends. Performance definition and optimization goals are identical to those used for FIG. 64. Since current crowds to the inside of the bends, the extra width has the electrical effect of adding capacitance at each bend. Extra capacitance increases coupling to the wood and increases the change in antenna inductance as the dielectric constant of the moist wood changes with changes in moisture content. The antenna width and length and end pad size are adjusted to maximize performance and antenna gain.

FIG. 65 shows a conventional folded dipole with T-match but without meander routing to potentially reduce sensitivity to knots and other wood imperfections. This is a conventional dipole design with T-match and end capacitive pads using folds at the ends instead of meander routing to achieve a more compact design. Performance definition and optimization goals are identical to those used for the antenna of FIG. 64. Using the folds instead of meander routing may enable the tag to be less sensitive to tag placement and knots. Testing shows that the tag is actually more sensitive to tag placement and knots.

Figure 66:
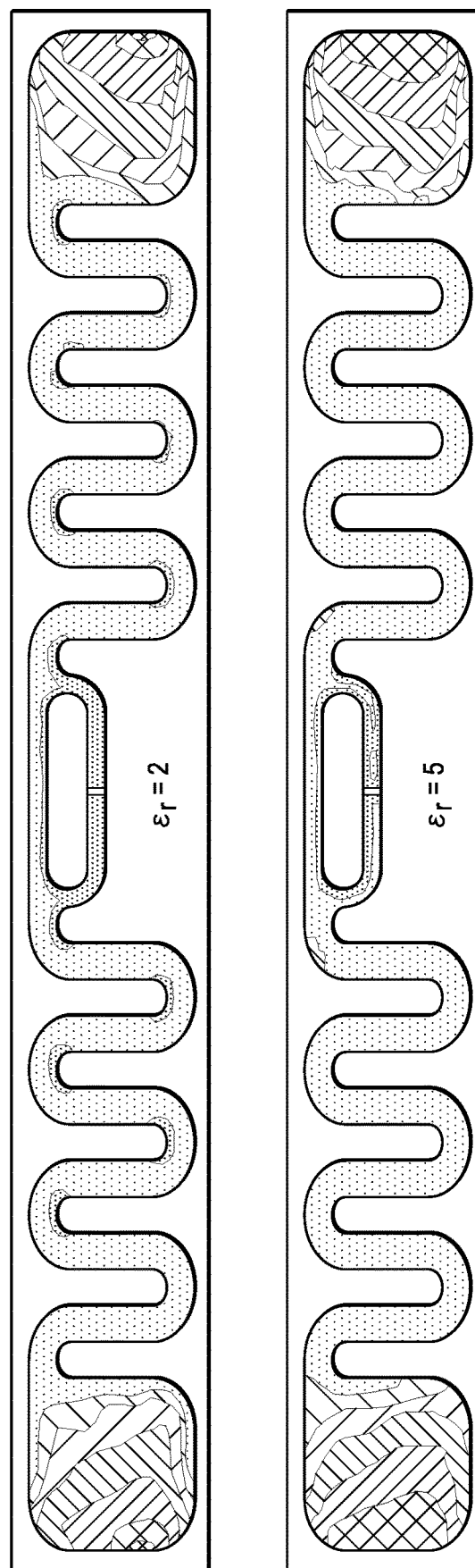
FIGS. 66, 67 and 68 show the current distribution for FIGS. 64, 63 and 65, respectively.
Figure 67:
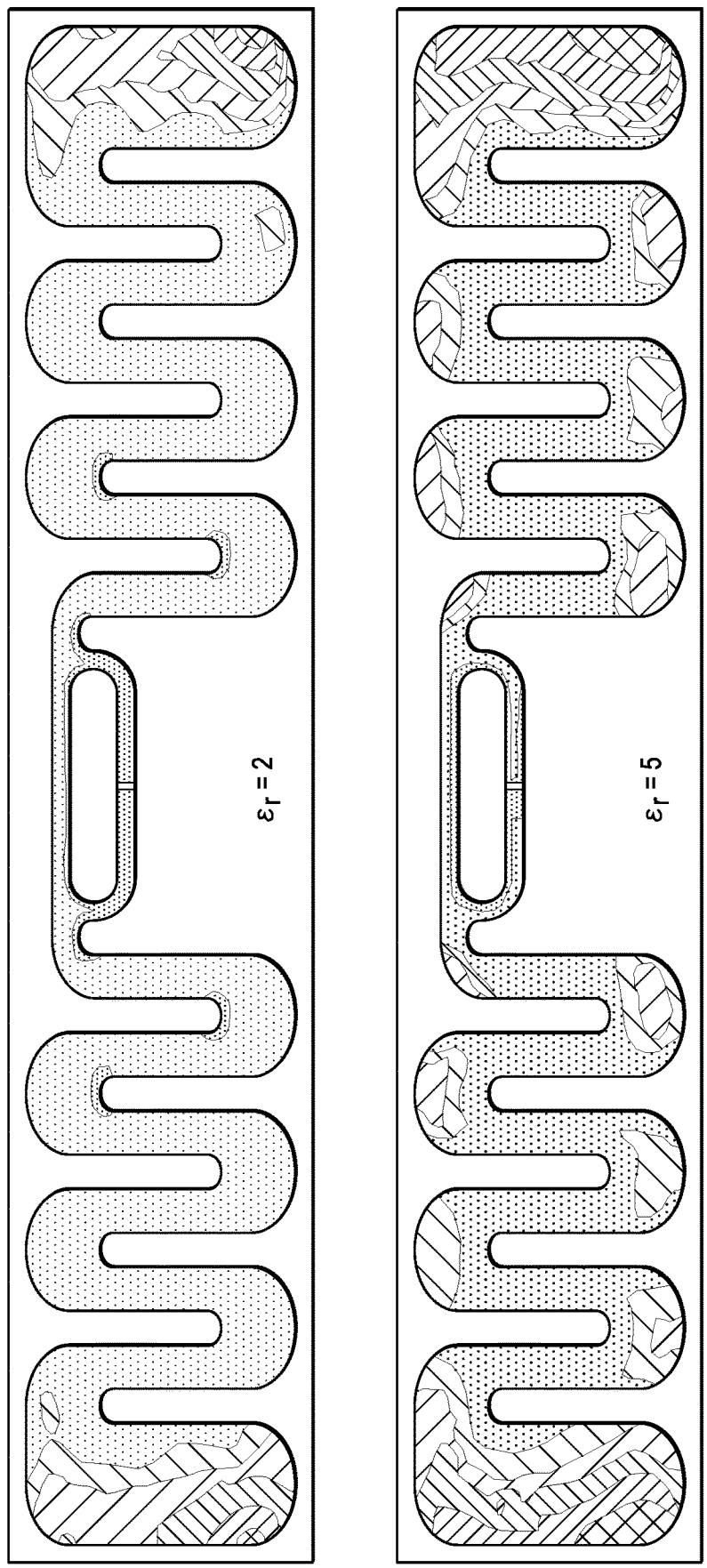
Figure 68:
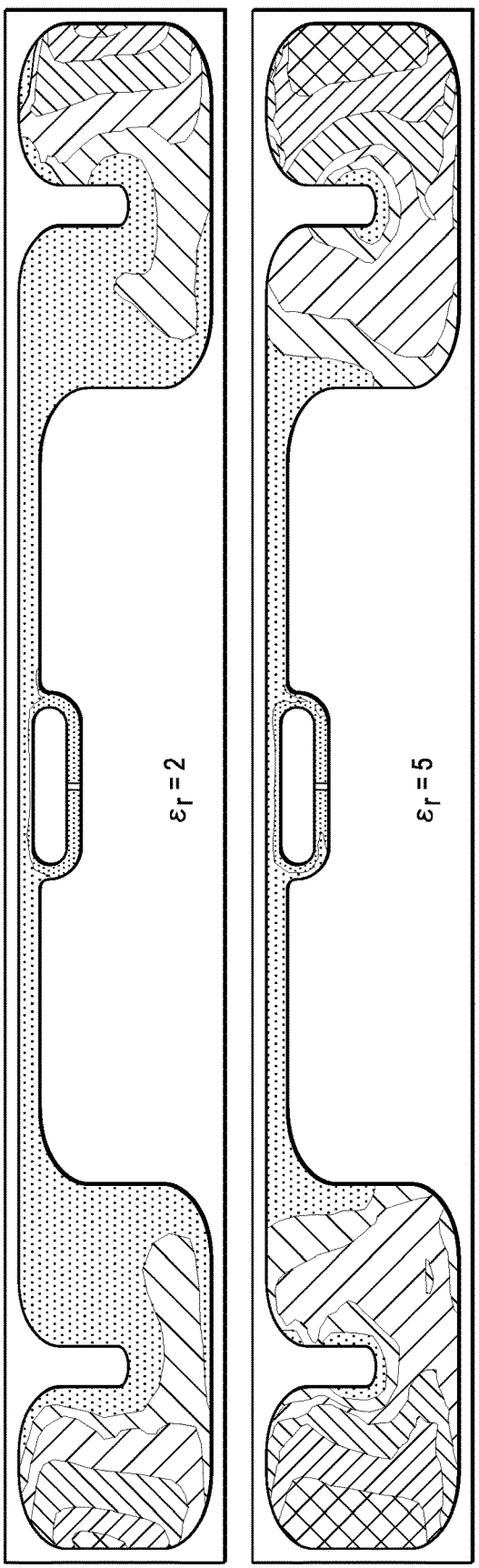

FIGS. 66, 67 and 68 show the current distribution for FIGS. 64, 63 and 65, respectively, at moisture levels of 2% (dielectric constant of 2) and moisture levels of 10% (dielectric constant of 5). The highest current density is shown in red and the lowest current density in dark blue. FIG. 66 shows no change in current density on the bends. FIG. 67 clearly shows a change in the current density on the widened bends which indicates that they are providing a contribution to the Self tuning engine code change due to the capacitance change that results from the change in the current density. FIG. 68 on the other hand, does not have a meandering trace to reduce antenna length and as a result has a larger dimension. It is more optimized for dealing with wood that have knots. Knots have different dielectric constants than clear wood, so placing an antenna on a knot can skew the sensor code more towards a value for the knot rather than the desired value for clear wood. Low sensitivity to knots is a desirable feature. The meander routing on FIG. 67 and FIG. 66 increase sensitivity to knots by concentrating a substantial length of the antenna in a relatively small area. FIG. 68 reduces the sensitivity to knots by avoiding meander routing, although that does force larger pads at the ends of the antenna plus folded routing to achieve some level of compaction.

The above three tags will be compared in the upcoming sections to the following moisture tags described in earlier sections of this disclosure.

Figure 69:
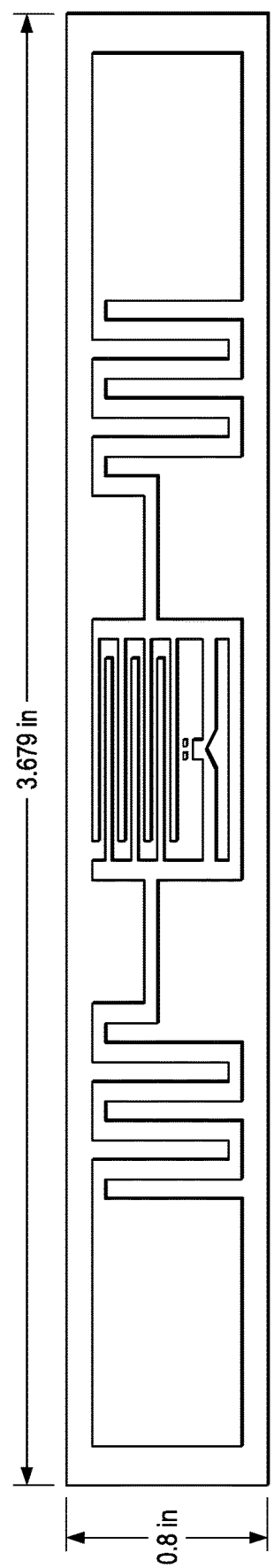
FIG. 69 shows a Moisture Tag which is a conventional compact dipole with added interdigitated capacitor in accordance with embodiments of the present disclosure.

FIG. 69 shows a moisture tag which is a conventional compact dipole with added interdigitated capacitor. This tag is shows very high sensitivity to moisture content and to wood imperfections.

The moisture tag of FIG. 59 which is a general-purpose dipole for mounting on arbitrary surfaces and exhibits low sensitivity to moisture. The moisture tag of FIG. 61 is a modification of the moisture tag of FIG. 59 with an added interdigitated capacitor. Similar to the Moisture Tag, this tag shows high sensitivity to moisture content and to wood imperfections.

The RFID industry has settled on a particular material set and construction as most suitable for low-cost high-volume production. This material set consists of approximately 9 um thick aluminum on a 50-250 um (2-5 mils) PET substrate with a thinner PET layer adhesively adhered covering the aluminum and die attached to the aluminum. All three designs can utilize this material set and construction to achieve the benefits of very low cost and high volume manufacturing.

FIG. 67 and FIG. 66 are shown to perform best for the pallet application while Moisture Tag and Moisture tag of FIG. 61 are overly sensitive to moisture content. FIG. 68 is about ⅔ as sensitive to moisture content as FIG. 67 and FIG. 66 but might provide a better solution for some applications.

A typical dielectric constant for wood at 2% moisture content is about 2.5 while for 10% moisture content the dielectric constant is about 51. Simulations of FIG. 67 and FIG. 66 indicate code movement over the dielectric constant range 2-10% moisture content of about 16 code ticks (16 binary count).

The disclosure includes moisture RFID sensors that are optimized for sensing moisture on wood by providing detectable code movement in the Self tuning engine in response to different moisture levels. Simulated results show that at least FIG. 67 and FIG. 66 show about 16 code tick movement over 2-10% moisture content range and about a 5 code tick movement over the 10%+/−2% range. The read range for the sensors is greater than 1 m and closer to 2 m.

Embodiments further disclose the concept of extending or displacing the environmental disturbance closer to the tag. This enables the placement of the RFID chip at a distance from the source of the environmental conditions to be detected and/or measured and then moving or extending any disturbance, via for example, a tail, closer to the sensing chip for the sensing to take place. The limitation on the distance that a tail can detect the disturbance is a function of the environmental variable that is to be sensed and its properties, in particular its ability to be transferred without disappearing or being diminished, as well as the properties of the tail and its material and construction. These properties, as well as the placement of the tag and tail (e.g. to take into effect gravity effects) also determine the time allowed for the complete transfer of the disturbance to the tag.

In an embodiment, in order to detect moisture at a remote location, a wicking material, referred to as a tail, is used to draw the moisture (e.g. water) to the tag where it can be detected by the IC 2000. One advantage of using such a wick is that the moisture can contact the tail at any or all points and that the tail can be any reasonable length and thus expands the sensing coverage area of the tag. In the current moisture embodiment where the moisture is water, the length of the tail is limited by the evaporation rate from the tail. The wick is essentially guaranteed to work as long as the pool of water is not exhausted and given sufficient time to travel up the tail to the tag.

Another advantage of the invention is the ability to place the tag itself in a more protected or convenient location.

The application, including placement, determines the time allowed for complete wicking of the water up to the tag. For example, placing the tag at a slightly lower vertical position from the end of the tail would utilize gravity to expedite the transfer of the moisture. Additionally, making sure the tail is monotonically descending further helps with such a transfer or displacement.

Additionally, the invention provides for an adaptable application of RFID tags, since, for example, the tail can be any reasonable length and constructed from a wide variety of environmental variable displacing/transferring materials (e.g. water-absorbing materials for a moisture tag).

In yet another aspect of this invention, the total code movement can be controlled by the degree of overlap between the tail and the sensing portion of the tag. For example, in an embodiment, a tag with a moisture sensing area 2 cm long could be fully covered by a tail so that when the tail has wicked moisture across its full length, the 2 cm sensing section is fully covered producing a total code movement of N ticks from dry to wet. Then in a second application, suppose the required code movement is N/2, then the tail could be positioned so that it covers only 1 cm of the sensing section.

In yet another aspect of this invention, the RFID tag and the tail could be affixed to each other from the factory and shipped and installed as a single unit. In another embodiment, an installation for such an RFID tag with a tail is done separately. This allows for a single tag that can be affixed with various types of tails (size, length, materials). The installation can be done by providing the tag and the tail with adhesive backing and then peeling the adhesive backing from the tag and installing on a surface, then peeling adhesive backing from the tail and installing over the tag and installation surface where the sensing is to be initiated.

In yet another embodiment, more than one type of tail can be affixed to the same RFID tag. This would allow the same tag to sense multiple environmental variables.

In yet another embodiment, the more than one type of tail can be affixed to more than one Self tuning engine located on the same integrated circuit. For example, in an embodiment one type of tail that is designed to sense one type of environmental condition can be connected to antenna port #1 (the two connections associated with Antenna Port 2502A of FIG. 25A and FIG. 25B) and a different type of environmental sensing tail/antenna can be connected to antenna port #2 (the two connections associated with Antenna Port 2502AN of FIG. 25A and FIG. 25B). In yet another embodiment, a third type of tail/antenna can be connected to a third Self tuning engine on the die (e.g. Antenna Port 2502B, not shown) or a tail as to sensing ports associated for example with the Reference Block 2520A of FIG. 25B where External element may comprise one or two ports. Additionally, the invention allows for the same type of tail/antenna to be connected to multiple ports in order to provide redundancy and/or additional sensing area coverage. Any combination of the above is part of the current invention.

In yet another embodiment, several of the same type of tail can be affixed to the same tag and extend in several directions to increase the area and direction of the sensing.

In an embodiment where water is to be sensed, the moisture RFID tag uses a tail that is a sheet of wicking material that is 0.1 mm thick and is the width of the tag. The tail completely covers the tag and extends well past the radiating edge.

Simulations as the water approaches the tag and then slowly wicks across the tag highlight very progressive change in sensor code as the water wicks along the length of the tag with negligible effect on tag sensitivity and strong total code movement of approximately 20 ticks. The simulations reflect ideal behavior of the tag. As described in the next section, the actual tags show code sensitivity reduction for sensor codes that are below approximately 10.

In an embodiment, the numerical experiment simulated in the previous section is duplicated in using a saturated paper towel that is the width of the tag and placed with the leading edge a variable distance from the radiating edge. So, the paper towel is used as the wick and it is approximately 0.25 mm thick when saturated with water.

Measured results closely track the simulation results. That is, code movement is progressive with approximately 20 ticks total movement with no impact on tag sensitivity for sensor codes above 10. A tag sensitivity drop is observed for sensor codes below approximately 10. Sensitivity loss for codes below approximately 10 are a known behavior of the model of RFID integrated circuit used for this experiment, and the behavior is independent of antenna design.

Therefore, embodiments enable a single tag to fulfill many roles such as asset tag, moisture tag and extended moisture tag (displaced/transferred disturbance). As a product, this allows for a single SKU product with multiple applications. Additionally, the invention provides for an adaptable application, since, for example, the tail can be any reasonable length and constructed from a wide variety of water-absorbing materials. In yet another embodiment, the total code movement can be limited by not fully covering the tag with the tail. In this embodiment, the apparatus is installed by peeling an adhesive backing from the tag and installing, then peeling an adhesive backing from the tail and install over the tag and installation surface to the water pooling location.

Figure 70:
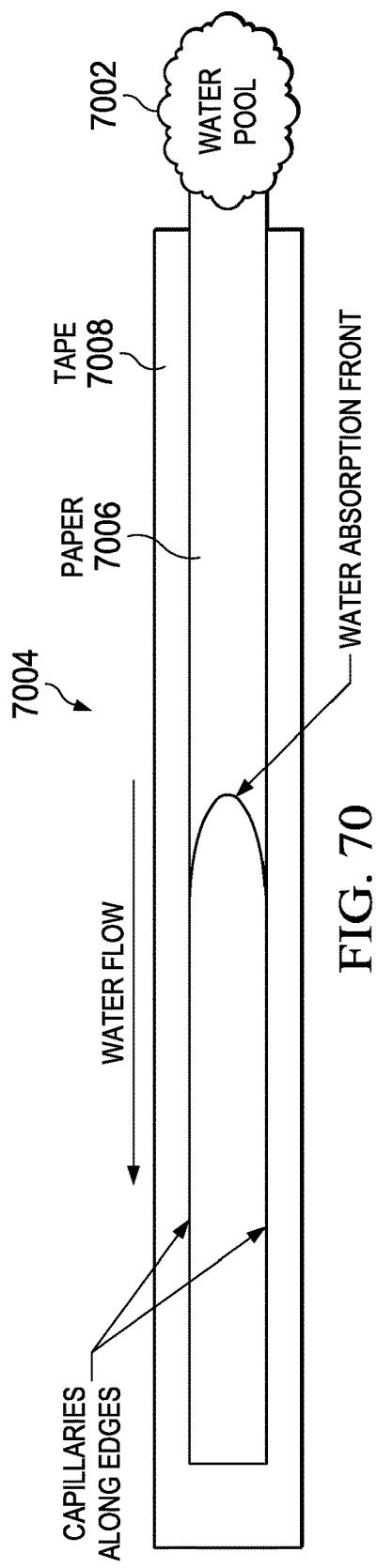
FIGS. 70 and 71 are diagrams of yet another embodiment of the wicking tails in accordance with embodiments of the present disclosure.
Figure 71:

In yet another embodiment of the wicking tails such as the ones described in the previous section is explained in the current section and description of FIG. 70. This embodiment transmits a variable to be sensed (e.g. moisture in the form of water 7002) from a remote location to the sensing tag 7004. The basic structure as shown is paper 7006 covered with tape 7008 and adhered to a surface (e.g. metal). While the adhesion can be at various points along the tail or along the entire tail, the current embodiment shows the adhesion to the surface only around the boundary of the paper. The current embodiment shows the wicking of the moisture (the variable to be sensed) via capillaries (also can be referred to as arteries) through the transmitting material (in this case paper). The capillary effect is much faster at drawing water along the tail than the water absorption in the paper. The capillary action is set up by placing tape 7008 over the paper 7006 and adhering the paper 7006 to the surface only around the boundary of the paper 7006. The capillary is formed between the tape and the surface. The paper 7006 forms a spacer with thickness that varies between the edge and center, so the water can find the optimal gap for the fastest capillary action. The water is drawn along the capillary on each edge, and then wets the paper from the sides, resulting in a U-shaped water front. FIG. 71 is an end view of wicking tail showing capillary embodiment.

While the embodiments do not limit the thickness or type of material to be used to wick the moisture to the tag, the thickness of the paper had an effect on the flow rate of the moisture (e.g. water) up the tail. It was found that the thinner paper had a better flow rate than thicker paper. Additionally, papers with ridges aligned in the direction of water flow had better flow rates, where the ridges provide variable spacing enabling the water to find the optimal gap for capillary action.

In another embodiment, a water (or moisture) soluble adhesive on the tape would be advantageous in some cases because it dissolves and enables the water to naturally find the optimal spacing for capillary action. Such a structure would be advantageous when the tags are to be disposed of after the moisture is detected rather than being reused. Such a soluble adhesive makes the tag easier to un-install when the tag is removed. Applications include placing these tags (with the extended tails) inside various parts of vehicle chassis to detect exposure to unwanted moisture and where these tags are optionally removed when the vehicle is being repaired due to the moisture exposure. New dry tags with the adhesive still intact can be then installed.

The capillary tail described above is ideal for wider flat surfaces. If the capillary action does not form due to non-optimal installation, then the water transport occurs at the absorption rate of the paper itself, and there is a tradeoff between tail length and absorption time. In yet another embodiment, holes are periodically punched or drilled into the tape along the center axis or alternatively at other parts of the tape. This would enable the detection of moisture along the tail rather than only at the end. If the tape by itself is providing significant capillary action, then it could simply wick the water to the paper tail and the operation would then proceed as described above.

Experiments were also run using four additional different embodiments. The four embodiments were the same structure as above but with: different width of paper towel for two of the embodiments, and two different wicking materials from EMI Specialty Material (10 mm of 7618 and 10 mm of 20535) for the other two embodiments. For these experiments, every sample tested took less than 90 second to exhibit 28 cm of wicking.

An application of such tags described above is for the measurement of moisture in various parts of vehicle chassis. For example, in the trunk area of a car and in particular the gutter areas in the trunk.

| | | EMI Specialty Materials | | Paper towel | |
|---|---|---|---|---|---|
| Experiment 4 Capillary Effect | Experiment run # | 7618 10 mm | 20535 10 mm | 15 mm Width | 12 mm Width |
| Seconds to travel Horizontal 28 cm | $1^{st}$ run $2^{nd}$ run | 89.1 61.2 | 46.7 50.1 | 37.9 38.2 | 37.9 38.2 |

Table 1 shows results of capillary effect wicking for the four embodiments

Figure 72:
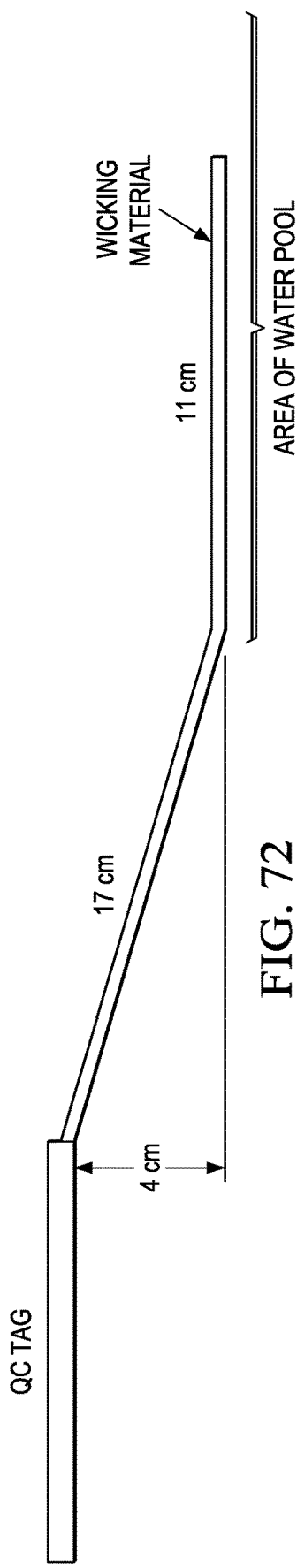
FIG. 72 is a diagram used to describe further experimentation on wicking materials within a car trunk (gutter of a vehicle body) involving an incline in accordance with embodiments of the present disclosure.

FIG. 72 is used to describe further experimentation on wicking materials within a car trunk (gutter of a vehicle body) involving an incline. Data shows the various wicking materials (three embodiments with three different wicking material as shown in the Table 2) is capable of providing wicking for 14 cm (horizontally 11 cm+3 cm incline) in less than a minute illustrating sensing water in the "trunk gutter", with the tag is placed in the gutter and the tail centered across the tag.

| Length of absorption | Experiment run # | EMI Specialty Materials | | Smartrac Wick Matl |
|---|---|---|---|---|
| | | 7618 | 20535 | |
| 14 cm total | $1^{st}$ run | 23 sec | 40 sec | 30 sec |
| 11 cm horizontal | $2^{nd}$ run | 50 sec | 52 sec | |
| 3 cm 13 degree | $3^{rd}$ run | 40 sec | 52 sec | |
| 21 cm total | $1^{st}$ run | 3 min 5 sec | 4 min 50 sec | 2 min 50 sec |
| 11 cm horizontal | $2^{nd}$ run | 3 min 45 sec | 3 min 52 sec | |
| 10 cm 13 degree | $3^{rd}$ run | 3 min 5 sec | 3 min 28 sec | |
| 25 cm total | $1^{st}$ run | 6 min 25 sec | 9 min 30 sec | 6 min 30 sec |
| 11 cm horizontal | $2^{nd}$ run | 7 min 10 sec | 7 min 40 sec | |
| 14 cm 13 degree | $3^{rd}$ run | 7 min 15 sec | 6 min 50 sec | |

Table 2 showing wicking experiments results with 13 degree incline

|  |  | EMI Specialty Paper Models | | |
| --- | --- | --- | --- | --- |
| Distance | Angle | 7618 | 15026 | 20535 |
| 7 cm | 25 degrees | 43 secs | 45 secs | 47 secs |
| 7 cm | vertical | 105 sec | 115 sec | 105 sec |
| 14 cm | 25 degrees | 5 min 15 sec | 5 min 45 sec | 6 min 15 sec |
| 14 cm | vertical | 11 min 20 sec | 11 min 10 sec | 10 min 45 sec |
| 21 cm | 25 degrees | 5 min 15 sec | 5 min 45 sec | 6 min 15 sec |
| 21 cm | vertical | 43 min 30 sec | 35 min 20 sec | 33 min |
| 25.5 cm | 25 degrees | 18 min 25 sec | 18 min 45 sec | 18 min |
| 25.5 cm | vertical | >1 hr 30 mins | 1 hr 13 min | 1 hr 3 min |

Table 3 showing wicking experiments results for vertical and 25 degree incline

In yet other embodiments, experiments were conducted with a 25 degree incline and a vertical incline. The results are shown in Table 3. In yet another embodiment, another experiment was conducted with a wick stuck to a metal plate with double sided tape and the wick loose. The data was similar to the 25 degrees data above.

For all of the above embodiments, the RFID tag/sensor can be read in multiple states, the calibrated neutral state (i.e. its unique impedance) and the one or more states after exposure to an event. In contrast to prior art where the RFID tag can be read in one state and the absence of a reading is an assumption of exposure (a second state). Such prior art results in an inability to distinguish between exposure to the desired event, removal (dislodging) of tag, or tag failure. The current disclosure does not suffer from this drawback and a reading would clearly indicate the exposure to the event and, in some embodiments, the level of exposure.

For all of the above embodiments in this section a self-tuned passive radio frequency identification (RFID) sensor is used (see also FIGS. 3, 4, 5, 6, 8, 11, 15, 20 and their associated discussions). In another embodiment, a conductor or transmission line couples the antenna to the processing module allowing the antenna to be positioned remotely or offset from the processing module. In yet another embodiment, a sensor having the sensor impedance that varies with the environment may be coupled to the processing module wherein the sensor impedance may be sensed via a sensor tuning module in much the same way that the antenna impedance is sensed and since a reactive component impedance is determined and a value representative of the impedance is produced which may again be transmitted to an RFID reader for external processing.

In one embodiment, the sensor is offset from the processing module via a conductor or transmission line. In one particular embodiment, the sensor is positioned within a cavity offset from the processing module wherein the cavity is impervious to radio frequency signals. This sensor may be an open circuited transmission line where the open circuited transmission line only introduces a capacitance when liquids are present proximate to the open circuit transmission line. The capacitance changes in such an example may change with the volume of liquid proximate to the open circuited transmission line. This is extremely useful when placing liquid or water sensors within cavities such as those contained within a vehicle chassis or when the cavities are prone to fluid incursion. This allows the sensor to be offset from the processing module where the environment to be sensed is hostile to the processing module.

In another embodiment, the sensor may be an interdigitated capacitor wherein the capacitor's impedance changes in response to moisture, i.e. humidity proximate to the interdigitated capacitor. In the case of the interdigitated capacitor, the impedance may change in response to an environmental dialectic constant change in the environment proximate to the interdigitated capacitor. This may occur when different gasses or fluids proximate to the sensor involve a change in dielectric constant at the sensor as may be caused by changing gas. Thus, in one embodiment the passive RFID sensor may be used to detect an environment toxin such as CO, $CO_2$, arsenic, hydrogen sulfide or other hazardous chemicals.

A change in an effective dielectric constant may involve applications involving moisture, including water vapor detection, sensing of wet material stock when wetness causes product loss or deterioration, sensing of wetness in applications sensitive to mold or corrosion, and detection of leaks in hard-to-access locations. Solid state films, having an effective dielectric constant, react to a variety of gases with a change in resistance or effective dielectric constant, and enable the construction of sensor tags that respond to industrially significant gases such as CO, $CO_2$, NOx, H2S, O2, and Cl2. Thin films deposited onto an interdigitated capacitor can produce sufficient change in circuit Q to build wireless passive sensors readable through the sensor code.

In one embodiment, a non-powering event would result in a change in the characteristics of the antenna. An example is the fingers of the antenna getting closer to each other thus changing the impedance characteristics of the antenna and thus the tuning frequency that a Self-tuning engine optimizes power at. So fundamentally resulting in a code, when the RFID tag/sensor is queried by a RFID reader or powered up by a CW signal (or powered up in any way, e.g. via a DC or AC voltage applied to the IC) that is different than a unique calibrated code in the RFID tag that was stored before the occurrence of the event, (e.g. at the factory, at the warehouse, prior to including the RFID tag sensor on/in an object that experiences the event, when stacking object on a shelf, when object is loaded on a transporter, etc.).

Physical distortion of the antenna itself causes a change in resonant frequency of the antenna, and the self-tuning engine can adjust a sensor code to accommodate the change. Applications are possible for alarms, stress detection, such as for bridge integrity monitoring and inflation of flexible objects. An example of such an event is the dropping of a box that has the RFID tag/sensor affixed to or within the box.

In yet another embodiment, for sensing level of wetness, in for example a diaper, several tags can be used to detect water level/levels of wetness. However, using the DC ports a single tag with a long tail can be used whose impedance will incrementally change as the level of wetness in, for example, the diaper rises.

In another embodiment, tuning loops, antennas and/or interdigitated capacitors are covered with strips of adhesive material that change color and thus impedance with exposure to temperature, light or the like.

Embodiments of the present disclosure allow for combining multiple sensing applications in a single die thus expanding the application space of passive RFID sensors. Additional applications include altitude sensing (via pressure sensing), external accurate temperature sensing, dew point and differentials (temperature, moisture, etc.).

The passive RFID sensor may also include an RFID power harvesting module operable to receive energy from the RFID reader and power the passive RFID sensor with the received power. The processing module may determine how much of this energy is to be consumed by the passive RFID sensor and divert any remaining energy to a reservoir power harvesting element. Additionally, the memory module may store identification information for the passive RFID sensor wherein the identification information may be provided with the impedance values associated with the antenna or a separate sensor and be provided to the RFID sensor for further processing. Additionally, a time stamp may be applied to this information. This may allow the RFID reader to generate an alarm signal based on certain measured environmental conditions.

In summary, embodiments of the present invention provide a passive RFID moisture tag/sensor. This moisture sensor includes one or more antenna structures having a tail. The tail is operable to transport a disturbance such as, but not limited to fluid or moisture from a monitored location wherein the antenna has an impedance and varies with proximity to the disturbance. An integrated circuit couples to the antenna structure. This IC includes a power harvesting module operable to energize the integrated circuit, an impedance-matching engine coupled to the antenna, a memory module, and a wireless communication module. The impedance-matching engine may vary a reactive component to reduce a mismatch between the antenna impedance and the IC and produce an impedance value (sensor code) representative of the reactive component impedance. The memory module stores the impedance value (sensor code) until the wireless communication module communicates with an RFID reader and sends the impedance value/sensor code to the RFID reader. The RFID reader may then determine an environmental condition such as the presence of moisture or fluids at the tail of the RFID sensor. This sensor may deploy several antenna and/or tails sensitive to unique disturbances. These tails may be used to monitor different locations as well as different types of fluids. In one particular embodiment, the disturbance is a fluid or moisture within the gutter of a vehicle body.

Thus, it is apparent that embodiments of the present disclosure have provided an effective and efficient method and apparatus for sensing changes to an environment to which the RFID tag is exposed.

Those skilled in the art will recognize that modifications and variations can be made without departing from the spirit of the present disclosure. Therefore, we intend that embodiments of the present disclosure encompass all such variations and modifications as fall within the scope of the appended claims. The system controllers or processors may comprise a microprocessor may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. Memory may couple to the microprocessor in the form of a single memory device or a plurality of memory devices. Such a memory device may be a read-only memory, random access memory, volatile memory, non-volatile memory, static memory, dynamic memory, flash memory, cache memory, and/or any device that stores digital information. Note that when the microprocessor implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory stores, and the processing module executes, operational instructions corresponding to at least some of the steps and/or functions illustrated in the FIGs.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A radio frequency identification (RFID) tag comprises:
a power harvesting circuit of the RFID tag operable to generate power for the RFID tag from a continuous wave of an inbound radio frequency (RF) signal received by the RFID tag;
an RF front-end of the RFID tag operable to receive the inbound RF signal and to transmit an outbound RF signal, wherein the RF front-end includes a tuning circuit that is tuned based on a capacitance setting, wherein tuning of the tuning circuit effects a characteristic of the RF front-end, and wherein the capacitance setting is indicative of a power level of the power; and a processing module of the RFID tag operably coupled to the RF front-end and the power harvesting circuit, wherein the processing module is operable to:
generate the capacitance setting to adjust the characteristic of the RF front-end to a desired characteristic to obtain a desired power level for the power.

2. The RFID tag of claim 1, wherein the tuning circuit comprises:
an inductance associated with an antenna; and
a variable capacitor operably coupled with the inductance to form a tank circuit, wherein capacitance of the variable capacitor is set based on the capacitance setting to change a resonant frequency of the tank circuit as the effect on the characteristic of the RF front-end.

3. The RFID tag of claim 2, wherein the inductance associated with the antenna comprises one or more of:
an inductor; and
the antenna.

4. The RFID tag of claim 1 further comprises:
an environment sensor proximally positioned to the RF front-end, wherein, when the environmental sensor is exposed to an environmental condition, the characteristic of the RF front-end is affected and wherein the processing module generates a second capacitance setting to substantial mitigate the effect on the characteristic of the RF front-end due to the environmental condition.

5. The RFID tag of claim 4, wherein the environmental sensor comprises:
a collecting section; and
a transporting section, wherein, when the RFID tag is positioned proximal to an object, at least a portion of the collecting section is within a remote area of the object, wherein, when the collecting section is subjected to moisture as the environmental condition, the collecting section collects the moisture, which is transported to the RF front-end via the transporting section to affect the characteristic of the RF front-end.

6. The RFID tag of claim 1, wherein the RF-front end comprises:
an antenna;
a receiver section coupled to the antenna; and
a transmitter section coupled to the antenna.

7. The RFID tag of claim 1 further comprises:
the processing module generating the capacitance setting to adjust the characteristic of the RF front-end such that the power of the RFID tag is adjusted to a desired power level.

8. The RFID tag of claim 1, wherein the processing module is further operable to:
generate a value representative of the capacitance setting; and
transmit, via the RF front-end, the value within the outbound RF signal.

* * * * *